United States Patent
Joseph et al.

(10) Patent No.: US 9,502,656 B2
(45) Date of Patent: Nov. 22, 2016

(54) ORGANIC ELECTROLUMINESCENT MATERIALS AND DEVICES

(71) Applicant: Universal Display Corporation, Ewing, NJ (US)

(72) Inventors: Scott Joseph, Ewing, NJ (US); Pierre-Luc T. Boudreault, Pennington, NJ (US); Alexey Borisovich Dyatkin, Ambler, PA (US); David Zenan Li, Princeton, NJ (US); Chuanjun Xia, Lawrenceville, NJ (US); Hitoshi Yamamoto, Pennington, NJ (US)

(73) Assignee: Universal Display Corporation, Ewing, NJ (US)

( * ) Notice: Subject to any disclaimer, the term of this patent is extended or adjusted under 35 U.S.C. 154(b) by 504 days.

(21) Appl. No.: 14/188,025

(22) Filed: Feb. 24, 2014

(65) Prior Publication Data

US 2015/0243893 A1 Aug. 27, 2015

(51) Int. Cl.
| | | |
|---|---|---|
| *H01L 51/00* | (2006.01) | |
| *C07D 491/04* | (2006.01) | |
| *C07D 495/04* | (2006.01) | |
| *H01L 51/50* | (2006.01) | |

(52) U.S. Cl.
CPC ......... *H01L 51/0032* (2013.01); *C07D 491/04* (2013.01); *C07D 495/04* (2013.01); *H01L 51/5016* (2013.01); *H01L 51/5024* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Lee, Chil Won et al., "Highly electron deficient pyrido[3',2':4,5]furo[2,3-b]pyridine as a core structure of a triplet host material for high efficiency green phosphorescent organic light-emitting diodes" Chem. Commun., 2013, vol. 49, No. 55, pp. 6185-6187.

(Continued)

*Primary Examiner* — Nathan T Leong
(74) *Attorney, Agent, or Firm* — Duane Morris LLP

(57) ABSTRACT

The present disclosure provides novel compounds based on azadibenzothiophenes, azadibenzofurans and azadibenzoselenophenes with at least two nitrogen atoms in the aza rings. The compounds can be used in green, red, yellow and white emitting devices as electron-transporting hosts.

21 Claims, 2 Drawing Sheets

(56) References Cited

U.S. PATENT DOCUMENTS

| | | |
|---|---|---|
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1* | 5/2008 | Mizuki .................. C07C 211/54 428/690 |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0187984 A1* | 7/2010 | Lin ...................... C07D 491/04 313/504 |
| 2011/0260138 A1 | 10/2011 | Xia et al. |
| 2012/0217485 A1 | 8/2012 | Lee et al. |

FOREIGN PATENT DOCUMENTS

| | | |
|---|---|---|
| EP | 2034538 | 3/2009 |
| EP | 2826781 | 1/2015 |
| JP | 200511610 | 1/2005 |
| JP | 2007123392 | 5/2007 |
| JP | 2007254297 | 10/2007 |
| JP | 2008074939 | 4/2008 |
| JP | 2011071163 | 4/2011 |
| JP | 2011084531 | 4/2011 |
| KR | 20120072787 | 7/2012 |
| KR | 20120092908 | 8/2012 |
| KR | 20140000611 | 1/2014 |
| KR | 20140013351 | 2/2014 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2012102967 | 8/2012 |
| WO | 2013102992 | 7/2013 |
| WO | 2013183851 | 12/2013 |
| WO | 2014/065073 | 5/2014 |
| WO | 2014/157599 | 10/2014 |
| WO | 2015/037675 | 3/2015 |

OTHER PUBLICATIONS

Office Action issued Jun. 23, 2016 for corresponding European Patent Application No. 15156258.4.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett, vol. 75, No. 3, 4-6 (1999).

(56) References Cited

OTHER PUBLICATIONS

Gao, Zhiciiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter, " Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).
Huang, Wei-Sheng et al., "Highly Phosphorescent Bis-Cyclometalated Iridium Complexes Containing Benzoimidazole-Based Ligands," Chem. Mater, 16(12):2480-2488 (2004).
Hung, L.S. et al., "Anode Modification in Organic Light-Emitting Diodes by Low-Frequency Plasma Polymerization of CHF3," Appl. Phys. Lett, 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives And Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergard et al., "Langmuir-Blodgett Light-Emitting Diodes Of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett, 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

ORGANIC ELECTROLUMINESCENT MATERIALS AND DEVICES

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and to organic materials used in such devices. More specifically, the present invention relates to novel host compounds based on azadibenzothiophenes, azadibenzofurans and azadibenzoselenophenes with at least two nitrogen atoms in the aza rings useful for phosphorescent OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

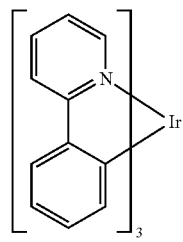

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

The present disclosure provides novel compounds based on azadibenzothiophenes, azadibenzofurans and azadibenzoselenophenes with at least two nitrogen atoms in the aza rings. The new compounds are useful as electron-transporting hosts for phosphorescent emitters in green, red, yellow and white phosphorescent OLEDs to provide low-voltage, high-efficiency and high-stability devices. These materials can be vapor-evaporated or solution processed.

According to an embodiment of the present disclosure, a novel compound having a formula, $G^1$—L—$G^2$, Formula I is disclosed. In Formula I, $G^1$ has the structure:

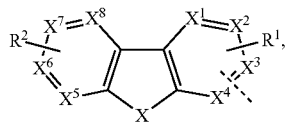

and $G^2$ has the structure:

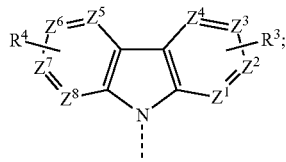

wherein L is selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein X is selected from the group consisting of O, S, and Se;

wherein each of $X^1$, $X^2$, $X^3$, $X^4$, $X^5$, $X^6$, $X^7$, $X^8$, $Z^1$, $Z^2$, $Z^3$, $Z^4$, $Z^5$, $Z^6$, $Z^7$, and $Z^8$ is carbon or nitrogen;

wherein at least two of $X^1$, $X^2$, $X^3$, $X^4$, $X^5$, $X^6$, $X^7$, and $X^8$ are nitrogen;

wherein at least one of $X^1$, $X^2$, $X^3$, and $X^4$ is carbon and bonded to L;

wherein $G^2$ bonds to L at N;

wherein each $R^2$, $R^3$, and $R^4$ represent mono, di, tri, tetra substitutions or no substitution;

wherein $R^1$ represents mono, di, tri substitutions or no substitution;

wherein $R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein the substitution is optionally fused to $G^1$ or $G^2$; and wherein when $R^3$ or $R^4$ is carbazole or substituted carbazole, the carbazole or substituted carbazole is connected to $G^2$ at 9-N.

According to an aspect of the present disclosure, a device comprising a phosphorescent organic light-emitting device incorporating the novel compound is also disclosed. The phosphorescent organic light-emitting device comprises an anode, a cathode, and an organic layer disposed between the anode and the cathode. The organic layer comprises the novel compound having the formula, $G^1$—L—$G^2$, Formula I, disclosed herein.

A formulation comprising the novel compound of the present disclosure is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
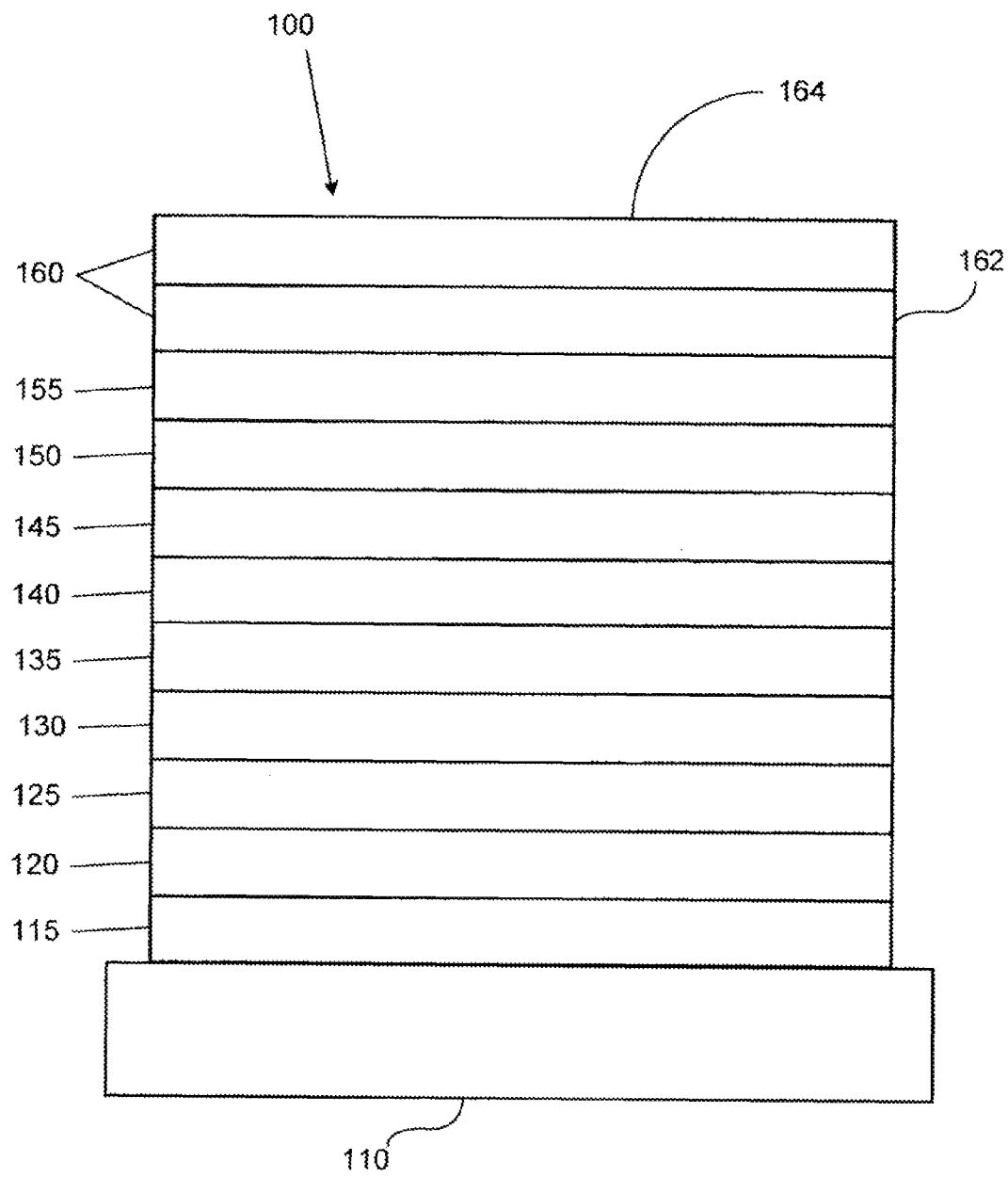
FIG. 1 shows an organic light emitting device that can incorporate the inventive compound disclosed herein.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
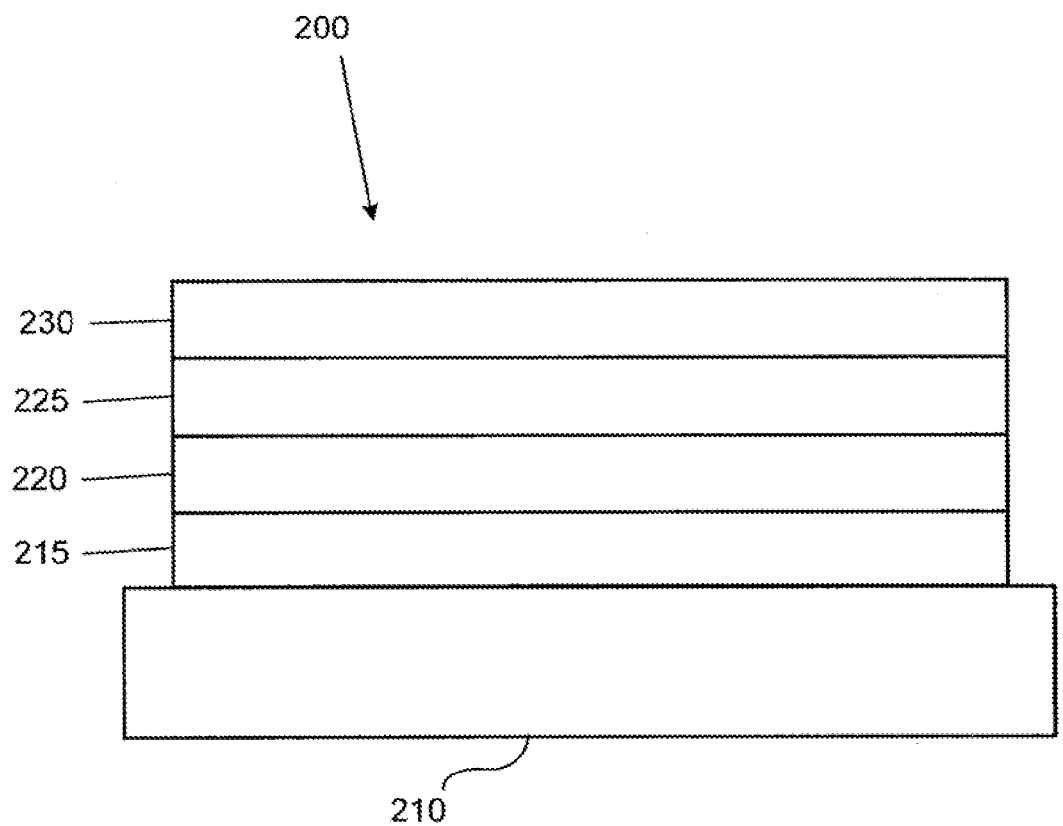
FIG. 2 shows an inverted organic light emitting device that can incorporate the inventive compound disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran). As used herein, these different ways of designating a substituent or attached fragment are considered to be equivalent.

According to an aspect of the present disclosure, a novel compound having a formula: $G^1$—L—$G^2$, Formula I, is disclosed. In Formula I, $G^1$ has the structure:

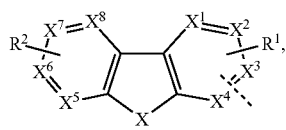

and $G^2$ has the structure:

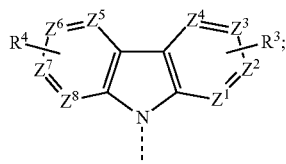

wherein L is selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein X is selected from the group consisting of O, S, and Se;

wherein each of $X^1$, $X^2$, $X^3$, $X^4$, $X^5$, $X^6$, $X^7$, $X^8$, $Z^1$, $Z^2$, $Z^3$, $Z^4$, $Z^5$, $Z^6$, $Z^7$, and $Z^8$ is carbon or nitrogen;

wherein at least two of $X^1$, $X^2$, $X^3$, $X^4$, $X^5$, $X^6$, $X^7$, and $X^8$ are nitrogen;

wherein at least one of $X^1$, $X^2$, $X^3$, and $X^4$ is carbon and bonded to L;

wherein the dashed lines represent the bonds between $G^1$ and L and between $G^2$ and L;

wherein each $R^2$, $R^3$, and $R^4$ represent mono, di, tri, tetra substitutions or no substitution;

wherein $R^1$ represents mono, di, tri substitutions or no substitution;

wherein $R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein the substitution is optionally fused to $G^1$ or $G^2$; and wherein when $R^3$ or $R^4$ is carbazole or substituted carbazole, the carbazole or substituted carbazole is connected to $G^2$ by N.

In one embodiment, when $R^1$ or $R^2$ is carbazole or substituted carbazole, the carbazole or substituted carbazole is connected to $G^1$ by N.

In one embodiment, X is O or S. In one embodiment, only two of $X^1$, $X^2$, $X^3$, $X^4$, $X^5$, $X^6$, $X^7$, and $X^8$ are nitrogen. In one embodiment, only two of $X^1$, $X^2$, $X^3$, $X^4$, $X^5$, $X^6$, $X^7$, and $X^8$ are nitrogen and on the same ring. In one embodiment, only two of $X^1$, $X^2$, $X^3$, $X^4$, $X^5$, $X^6$, $X^7$, and $X^8$ are nitrogen and on the same ring that is bonded to L.

In one embodiment, each $Z^1$, $Z^2$, $Z^3$, $Z^4$, $Z^5$, $Z^6$, $Z^7$, and $Z^8$ is carbon. In one embodiment, $R^1$, and $R^2$ are each independently selected from the group consisting of hydrogen, deuterium, halide, alkyl, phenyl, pyridyl, carbazolyl, and combinations thereof. In one embodiment, $R^3$, and $R^4$ are each independently selected from the group consisting of hydrogen, deuterium, phenyl, pyridyl, 9-carbazolyl, and combinations thereof.

In another embodiment, $G^1$ is selected from the group consisting of:

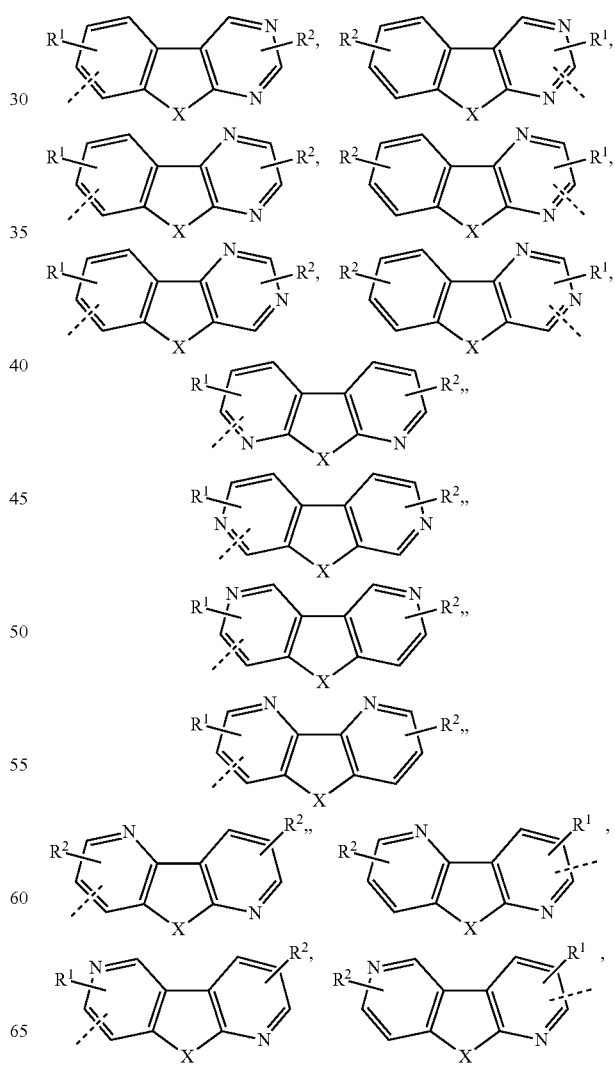

-continued
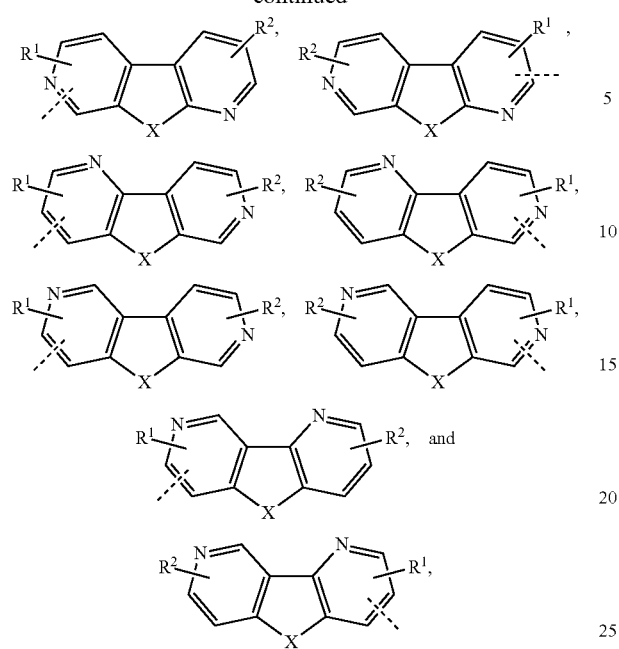
wherein X is selected from the group consisting of O, S, and Se.
In another embodiment, L is selected from the group consisting of:
a direct bond,
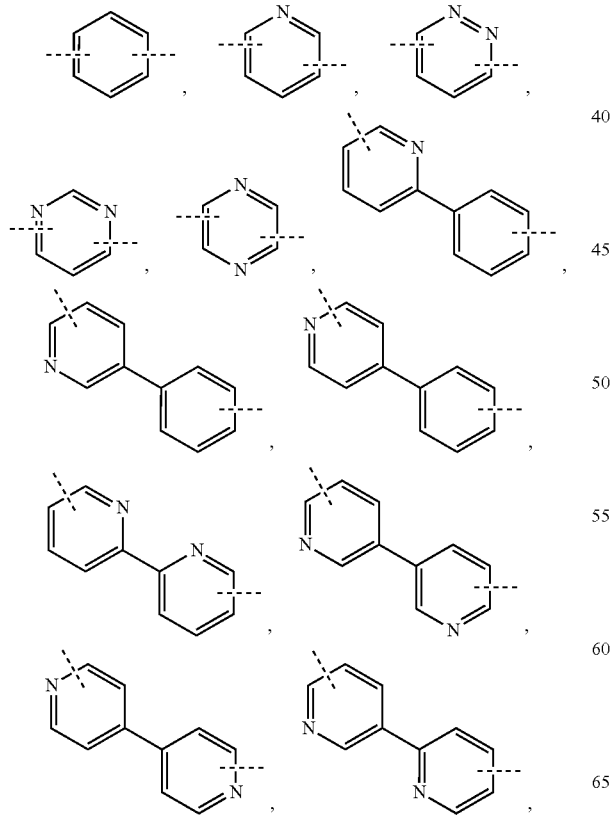
-continued
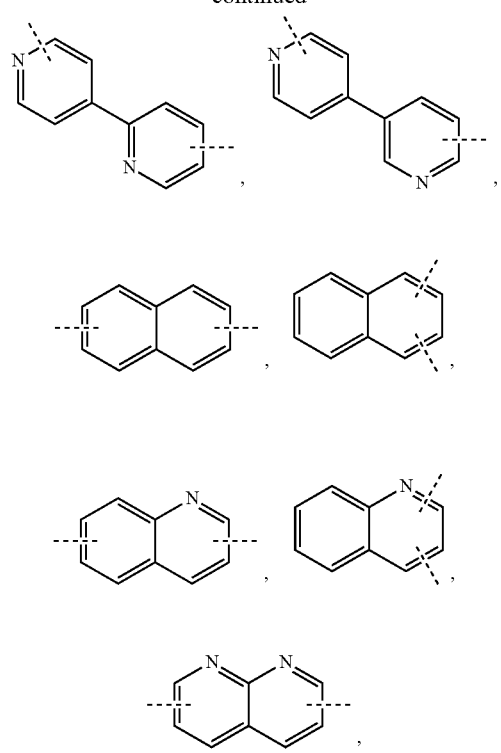
and combinations thereof.
In another embodiment, $G^1$ is selected from the group consisting of:
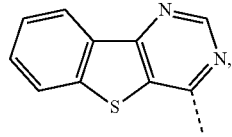
D1
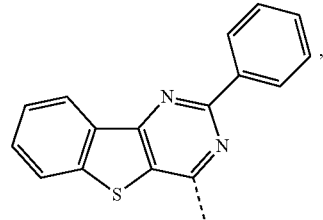
D2
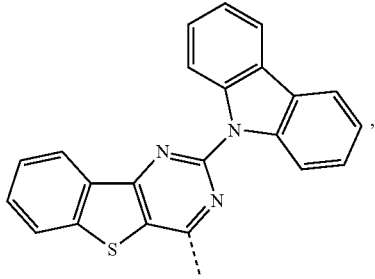
D3

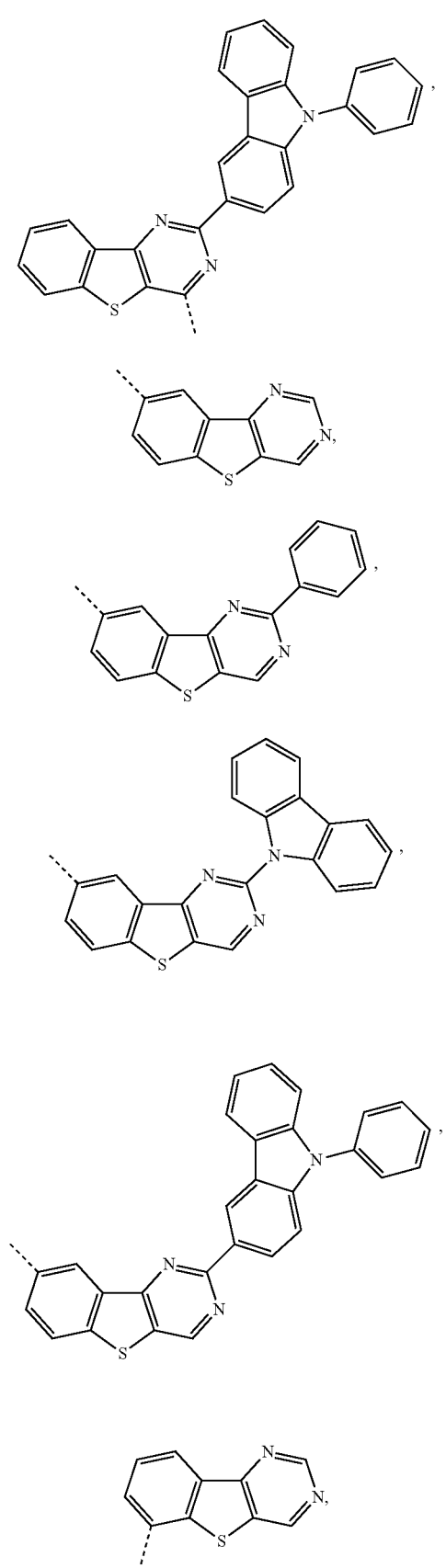
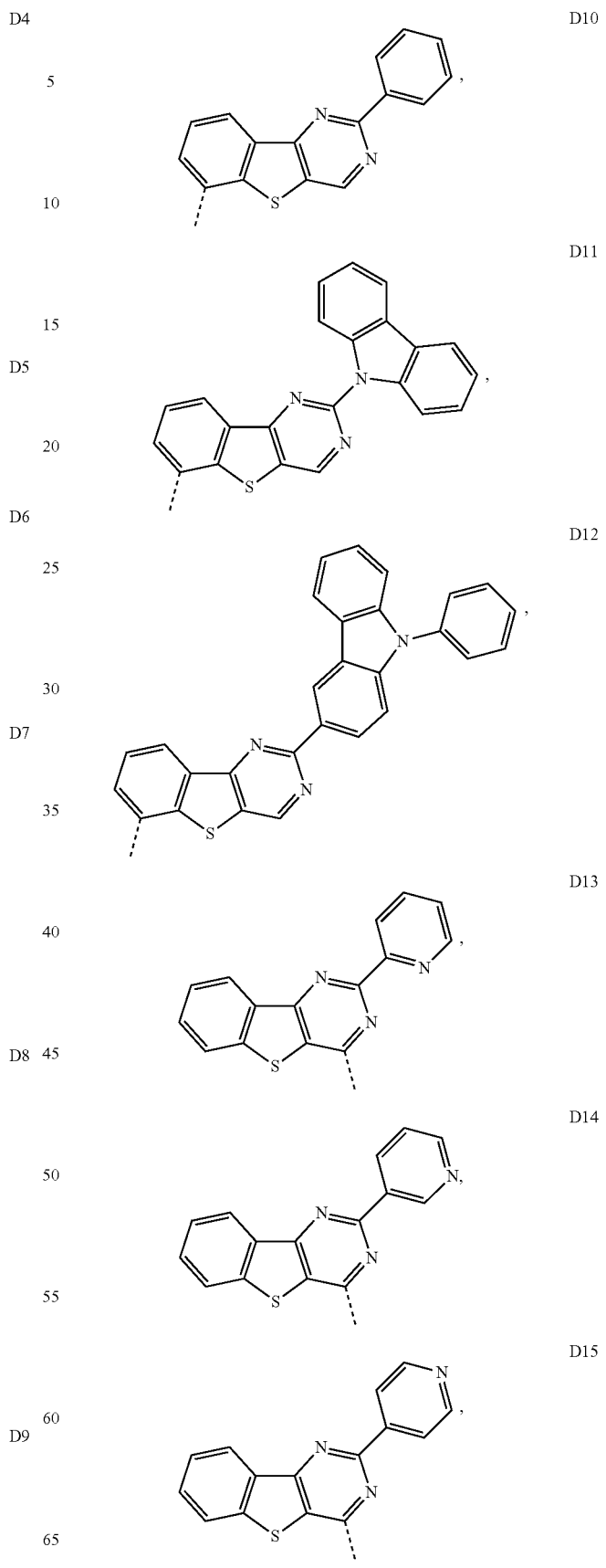

-continued
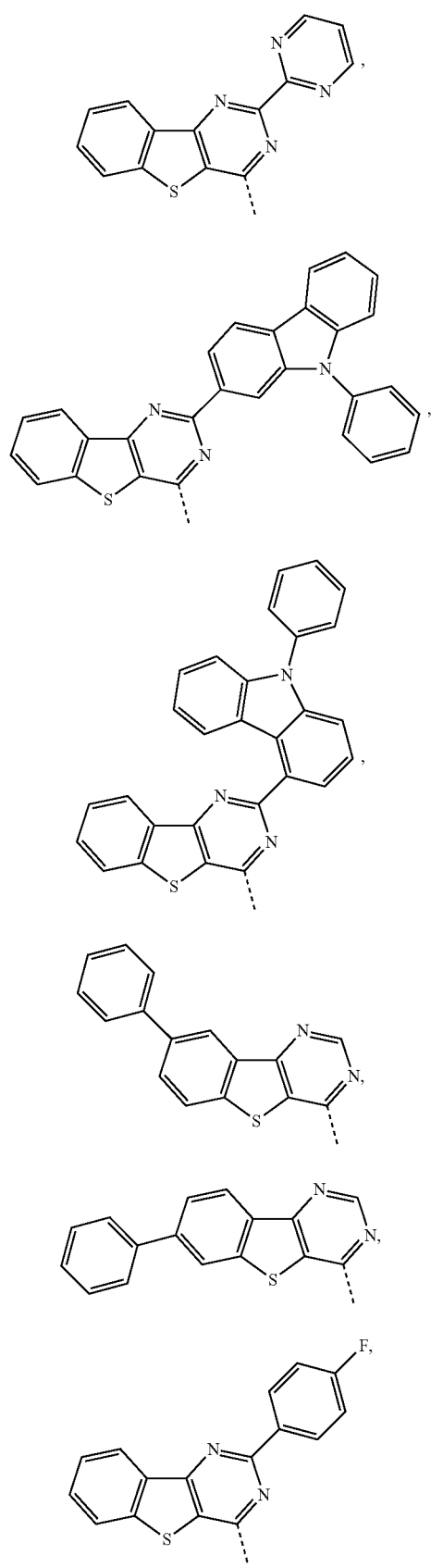
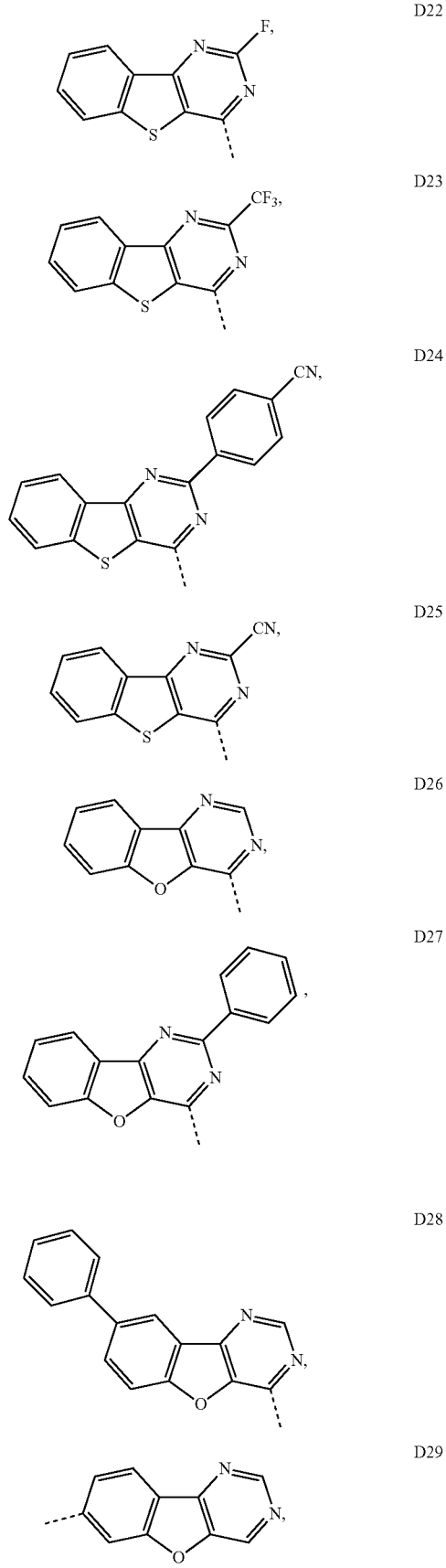

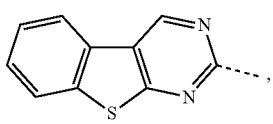 D30
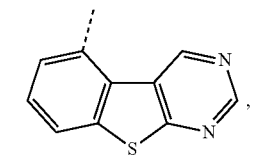 D31
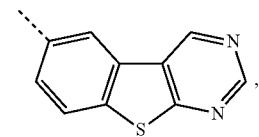 D32
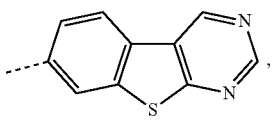 D33
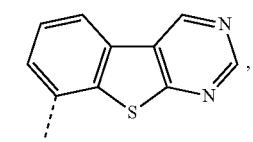 D34
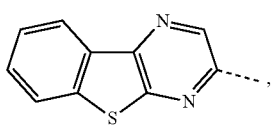 D35
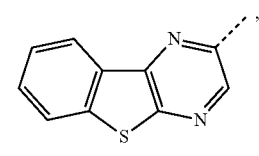 D36
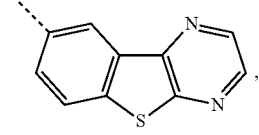 D37
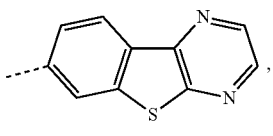 D38
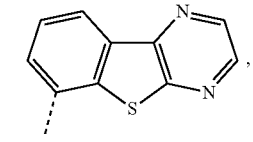 D39
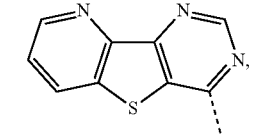 D40
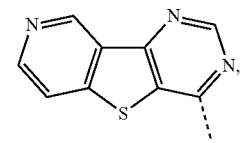 D41
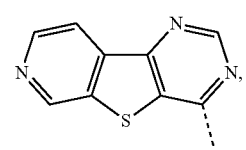 D42
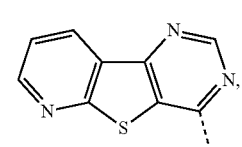 D43
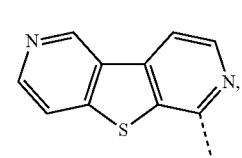 D44
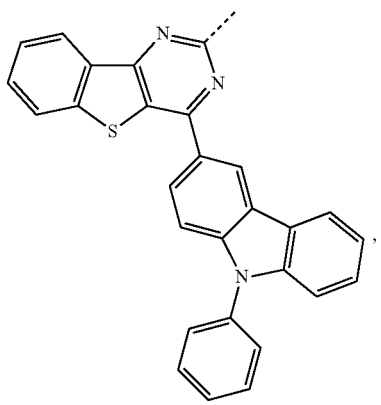 D45
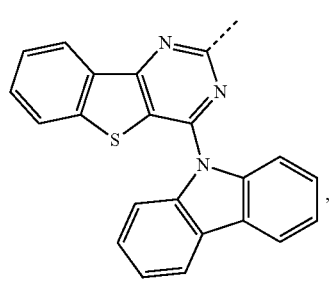 D46
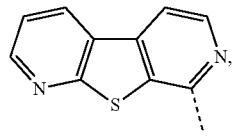 D47
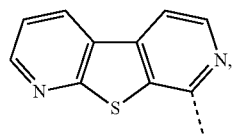 D48

-continued
D49 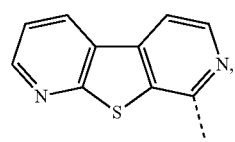
D50 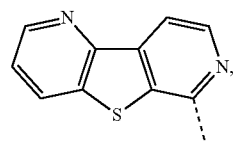
D51 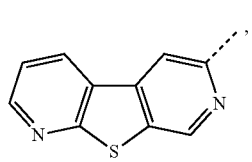
D52 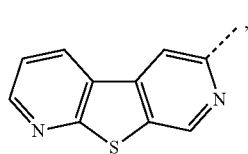
D53 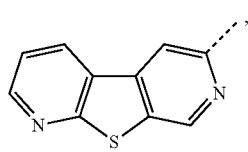
D54 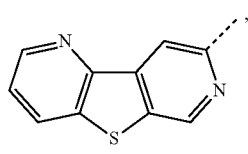
D55 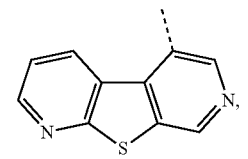
D56 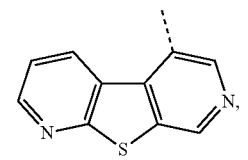
D57 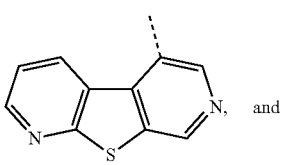 and
D58 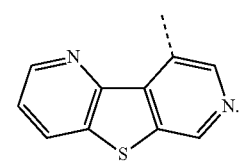
In another embodiment, L is selected from the group consisting of:
a direct bond (L1),
L2 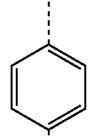
L3 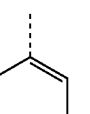
L4 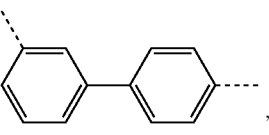
L5 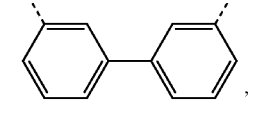
L6 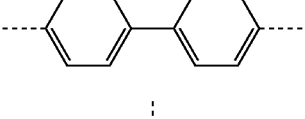
L7 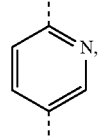
L8 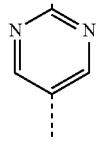
L9 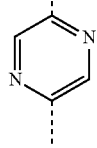
L10 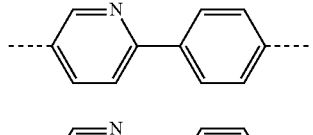
L11 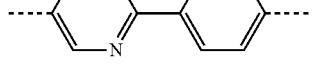

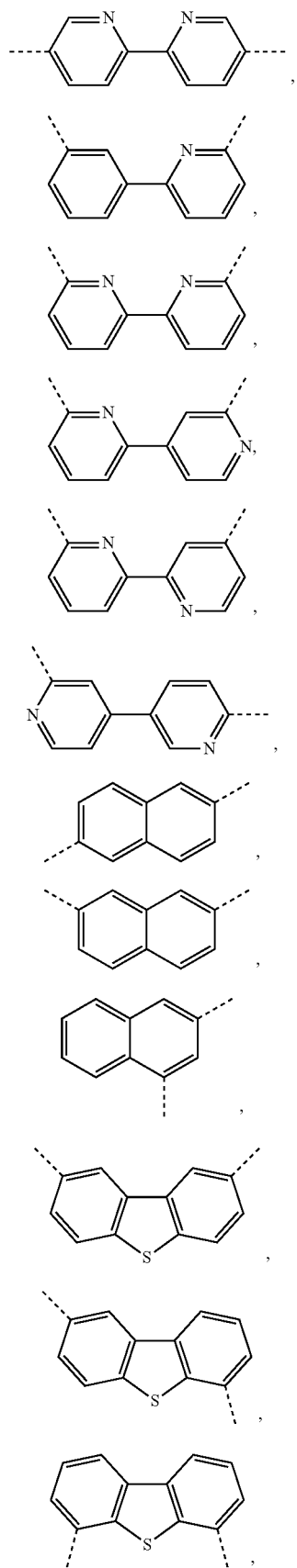
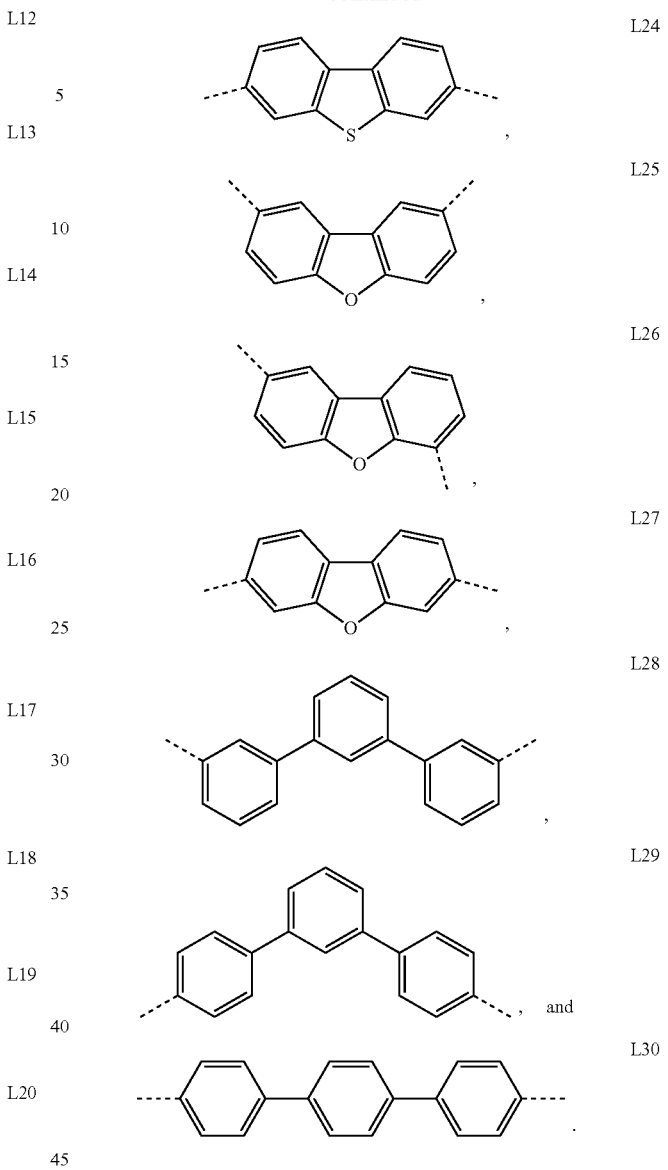
In another embodiment, $G^2$ is selected from the group consisting of:
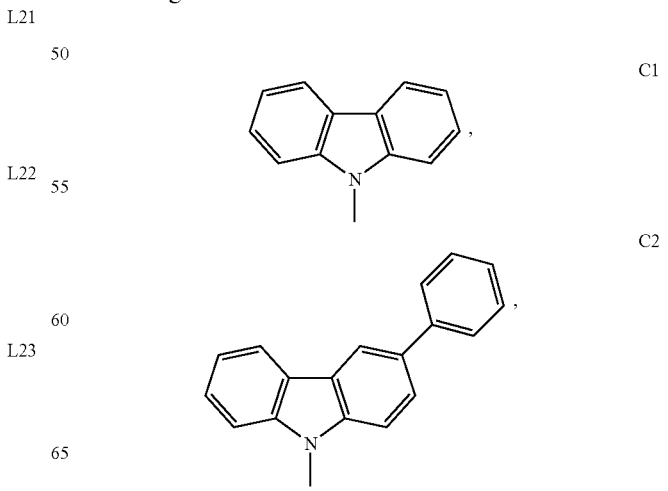

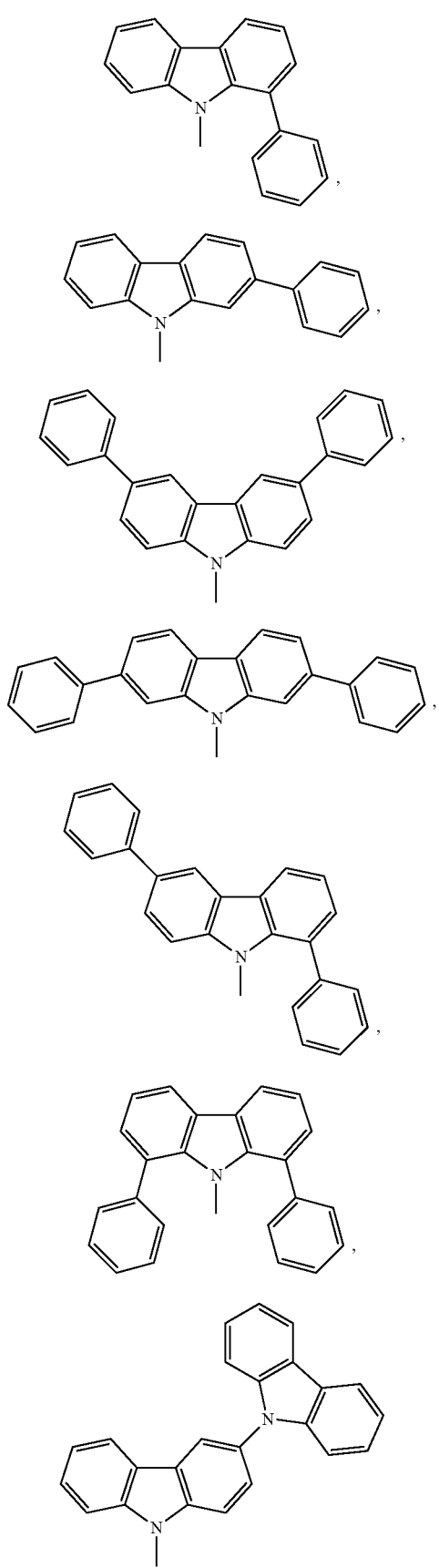
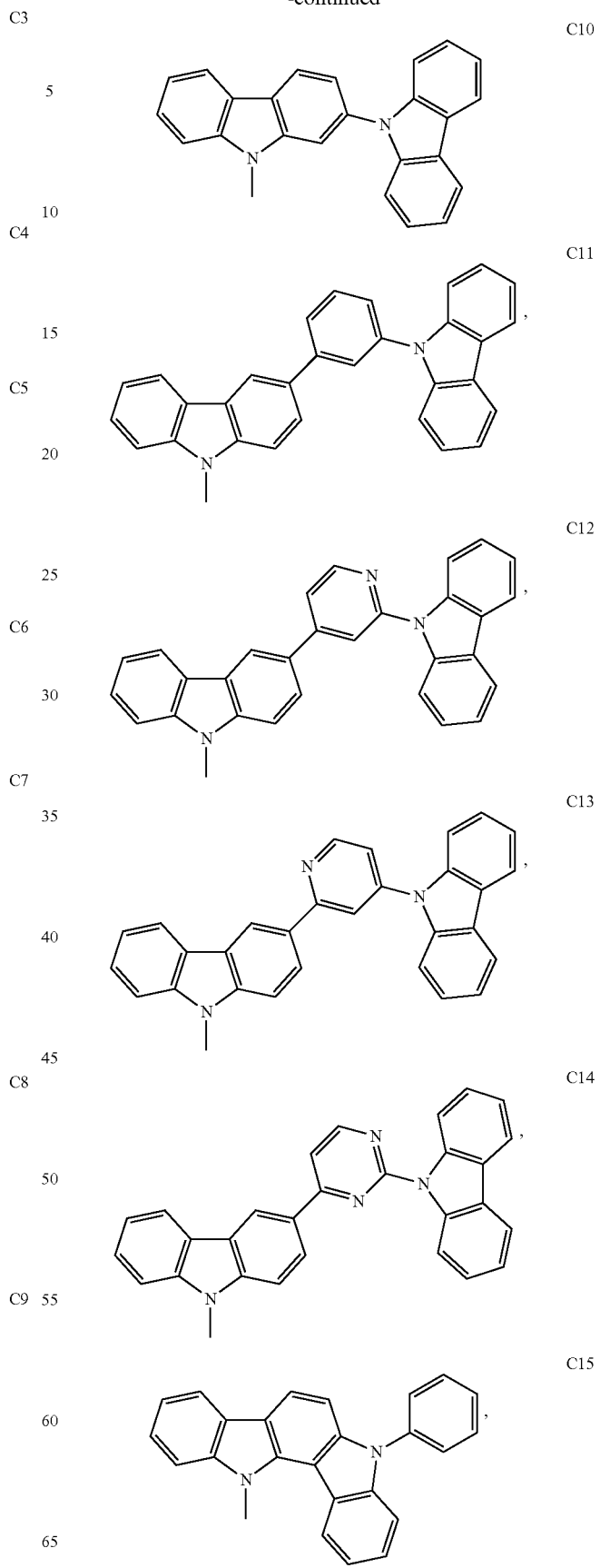

C16 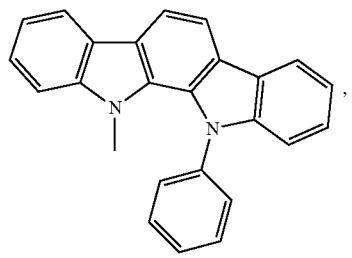

C17 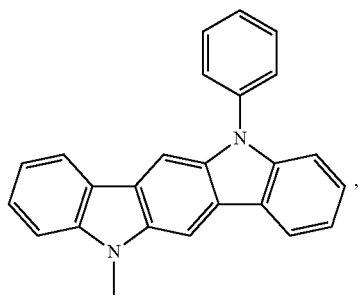

C18 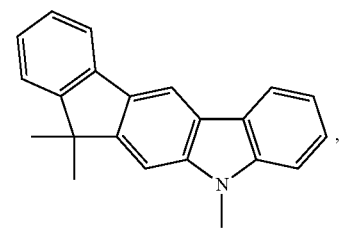

C19 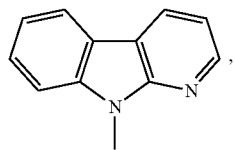

C20 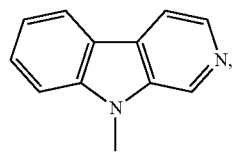

C21 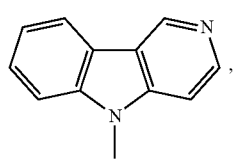

C22 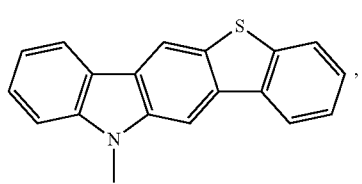

C23 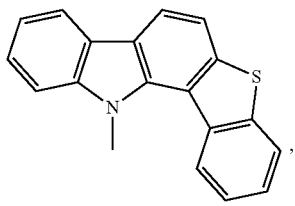

C24 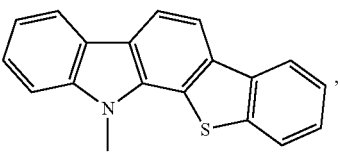

C25 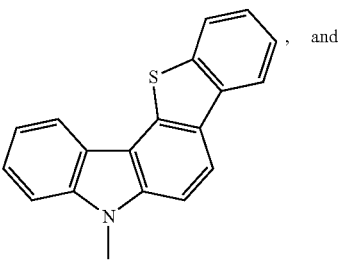

and

C26 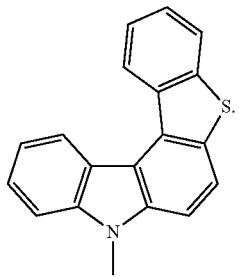

According to another embodiment, the novel compound having the formula: $G^1$—L—$G^2$ Formula I, is selected from the group of compounds Compound x defined by the formula Di-Lj-Ck;

wherein x=1740k+58j+i−1798, wherein i is an integer from 1 to 58, j is an integer from 1 to 30, and k is an integer from 1 to 26; and wherein D1 to D58, L1 to L30, and C1 to C26 have the chemical structures as defined herein.

According to another embodiment, the novel compound having a formula: $G^1$—L—$G^2$, Formula I, is selected from the group of compounds consisting of:

Compound 3

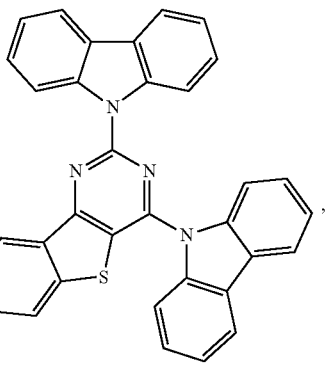

Compound 45
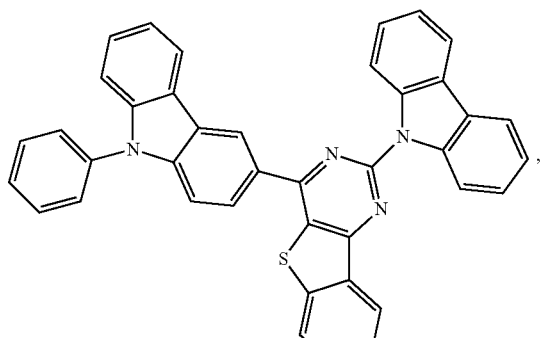
Compound 61
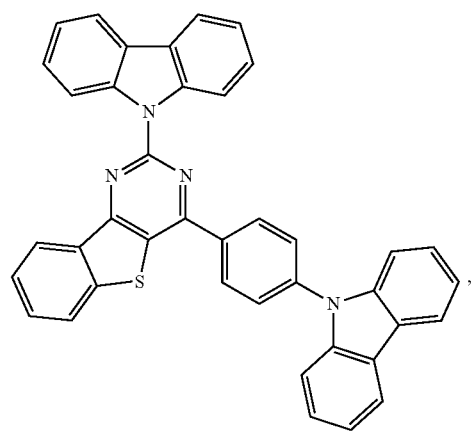
Compound 62
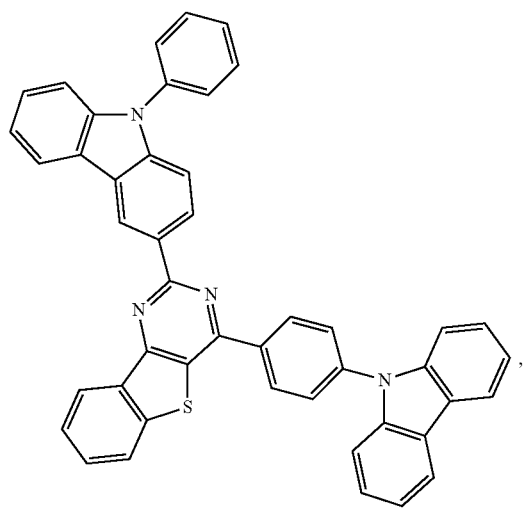
Compound 103
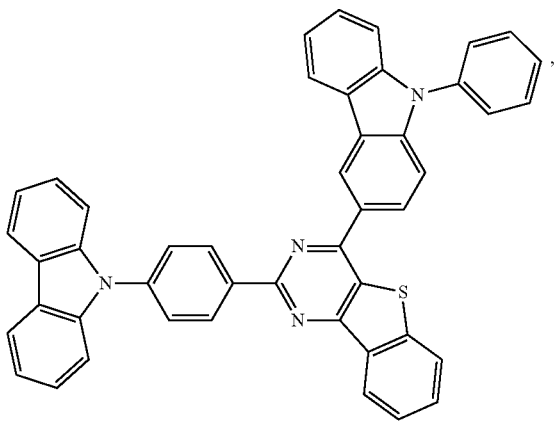
Compound 121
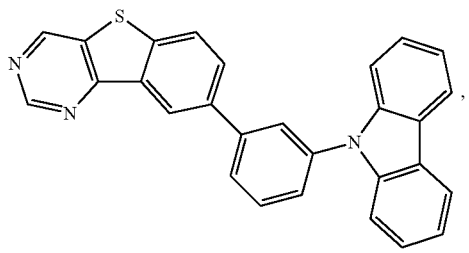
Compound 161
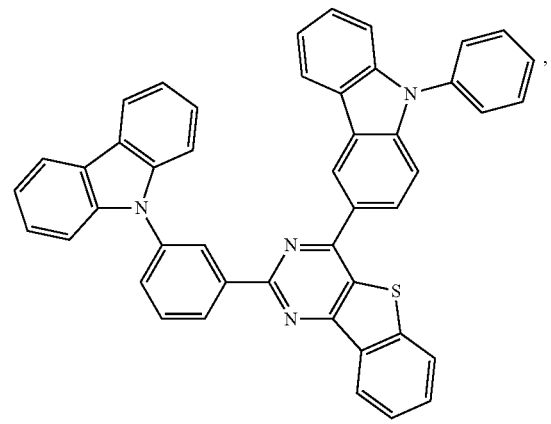

Compound 236
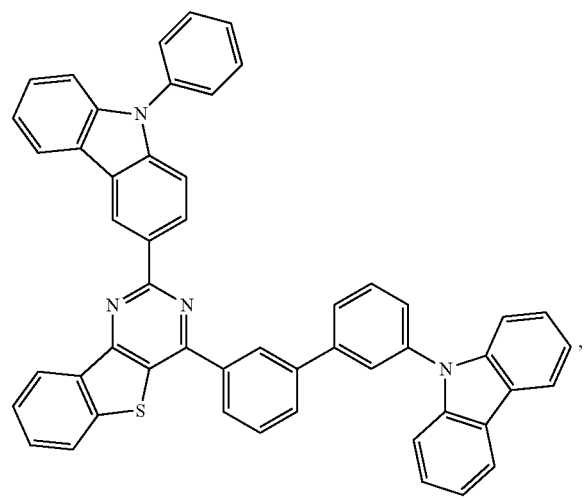
Compound 1742
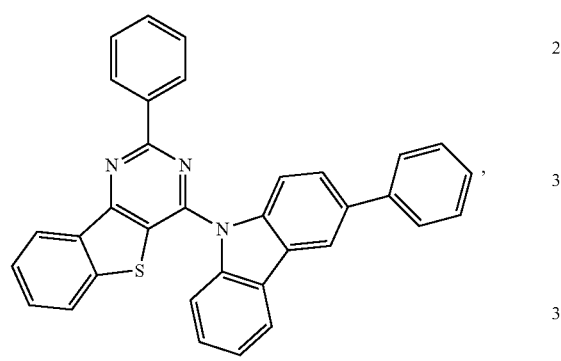
Compound 3481
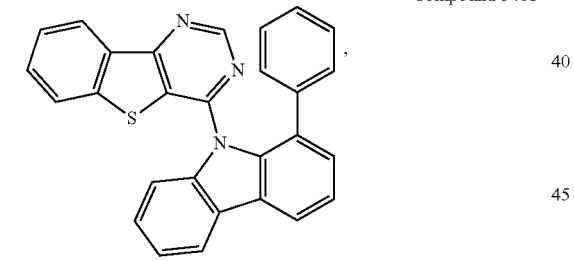
Compound 3484
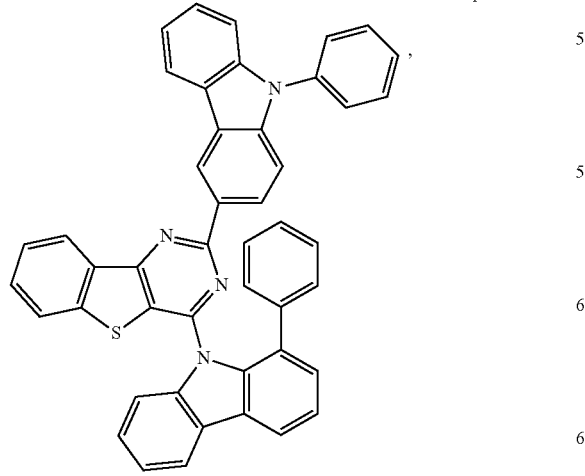
Compound 3539
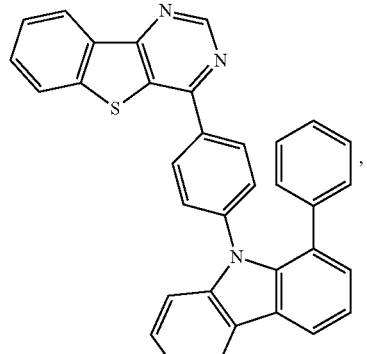
Compound 6961
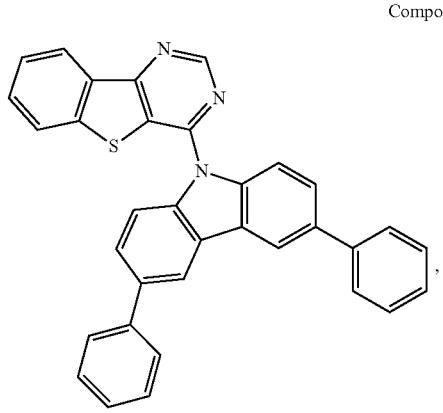
Compound 6962
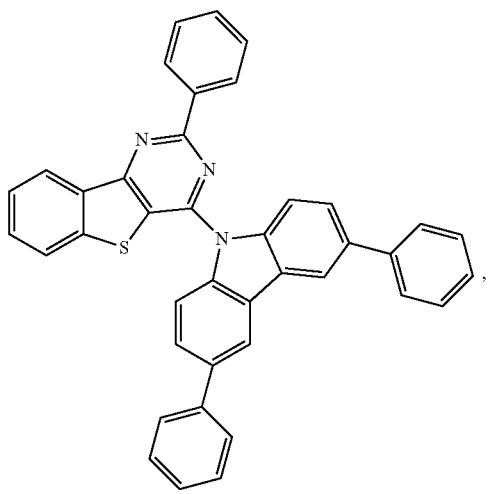

Compound 6987
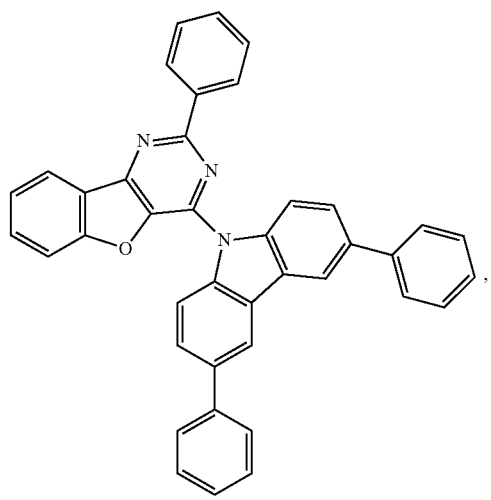
Compound 7063
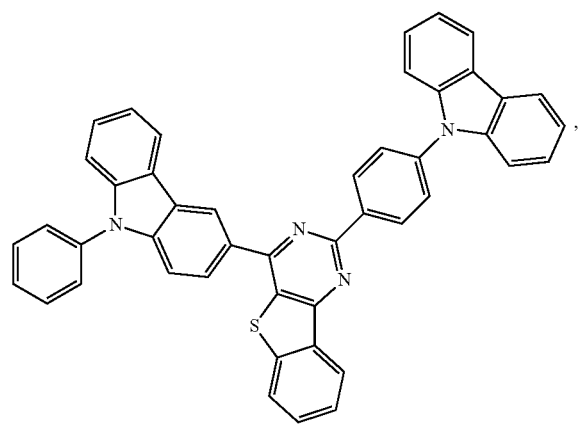
Compound 7121
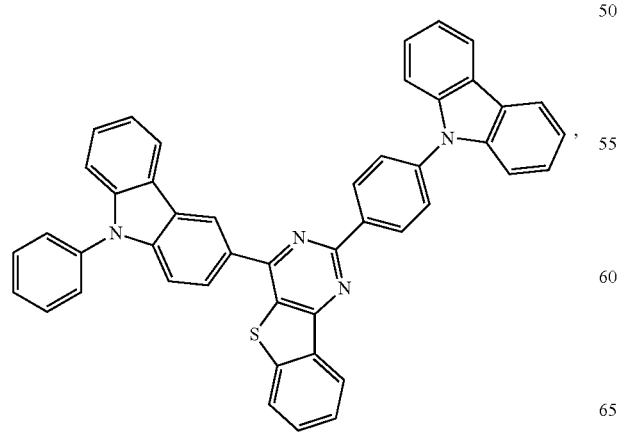
Compound 13921
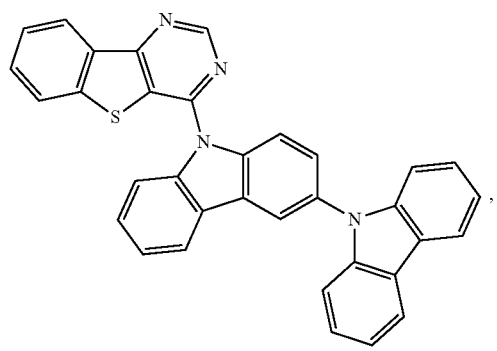
Compound 13922
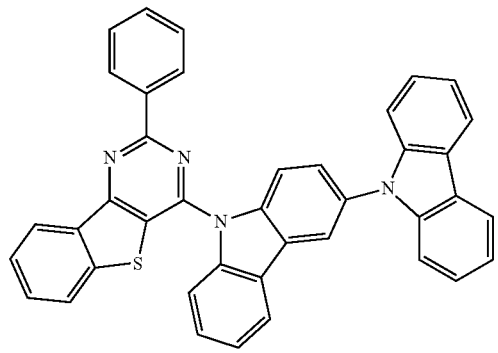
Compound 13923
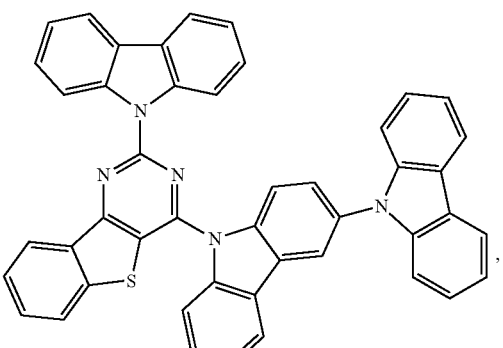

Compound 13924
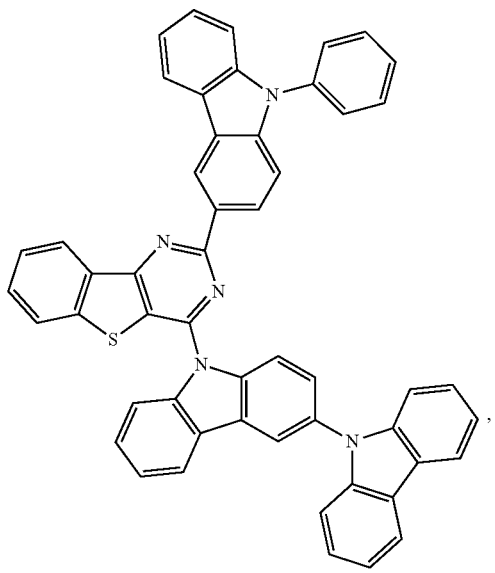
Compound 13929
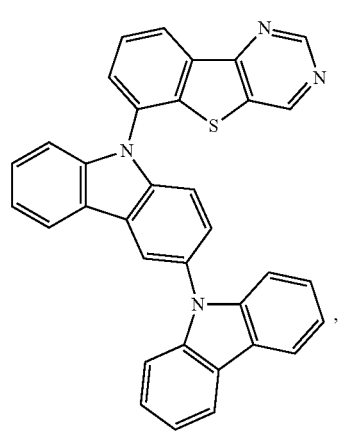
Compound 13935
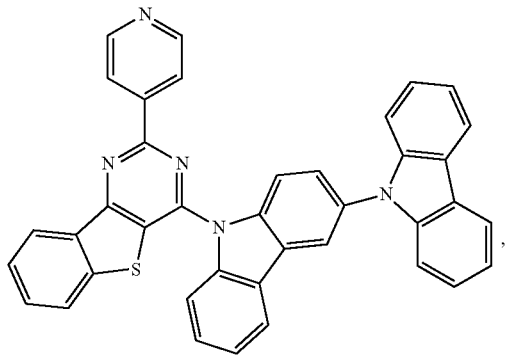
Compound 13936
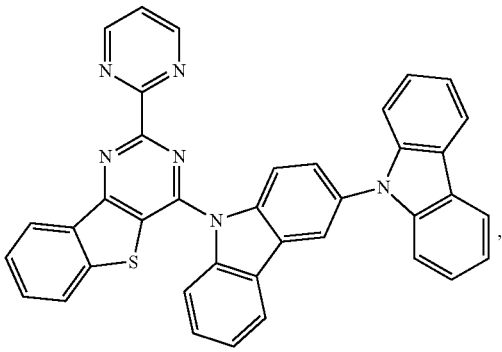
Compound 13979
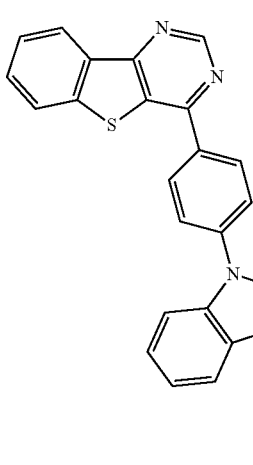
Compound 13981
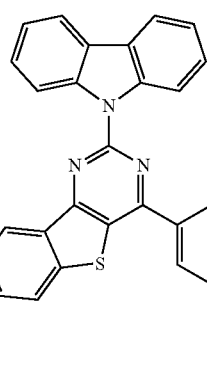
Compound 14037
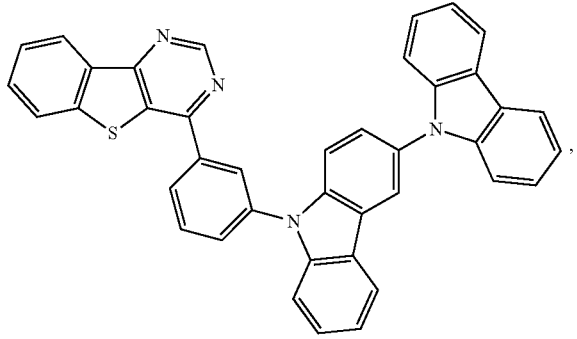

Compound 14038
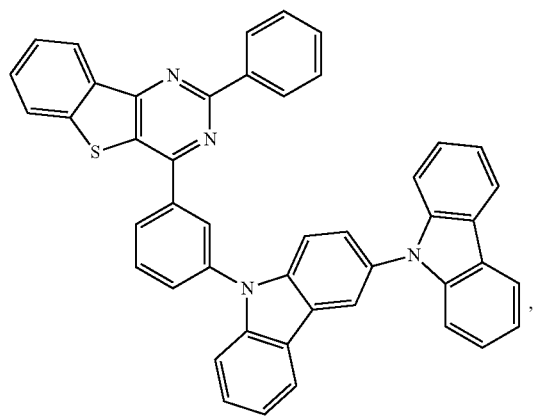
Compound 15661
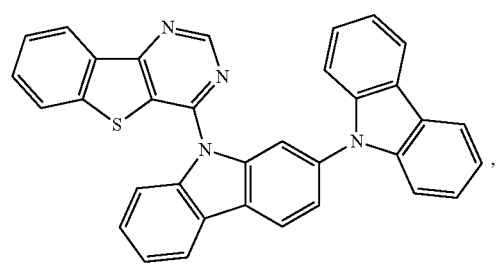
Compound 15662
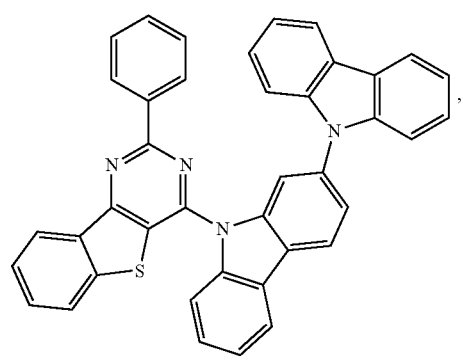
Compound 15663
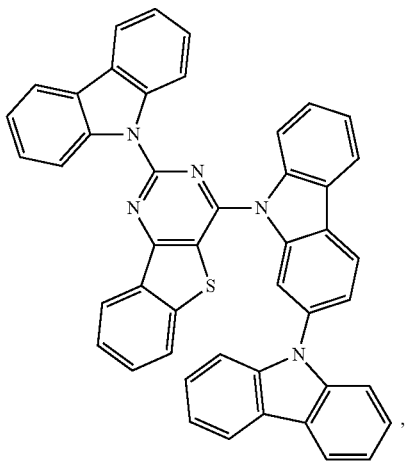
Compound 15665
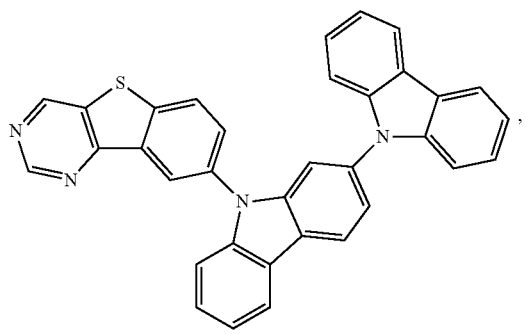
Compound 15669
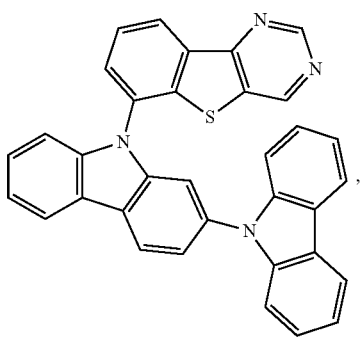
Compound 15719
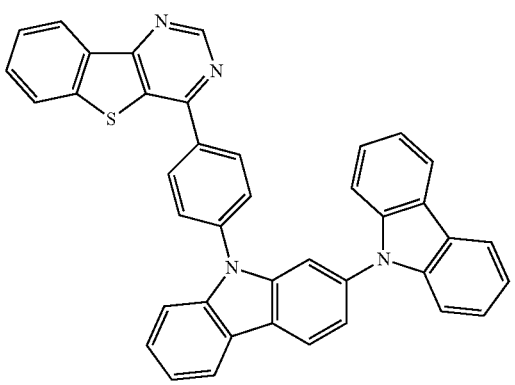
Compound 15777
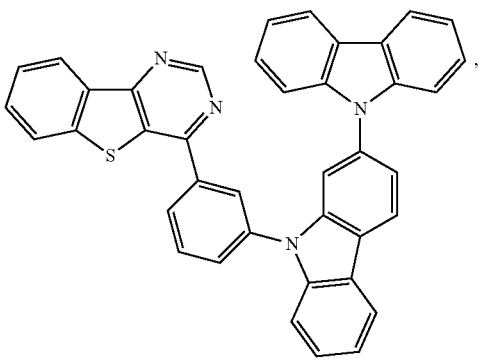

Compound 17401
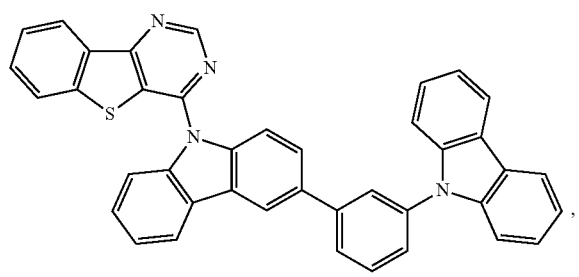
Compound 17459
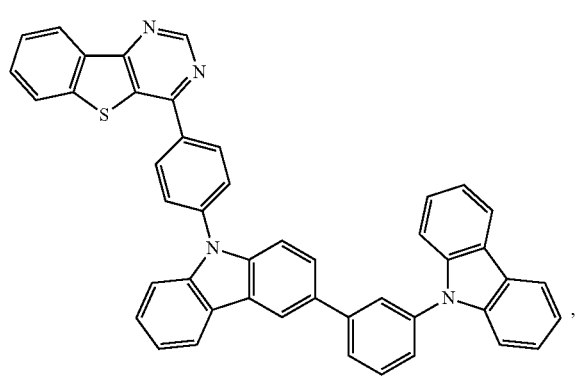
Compound 17517
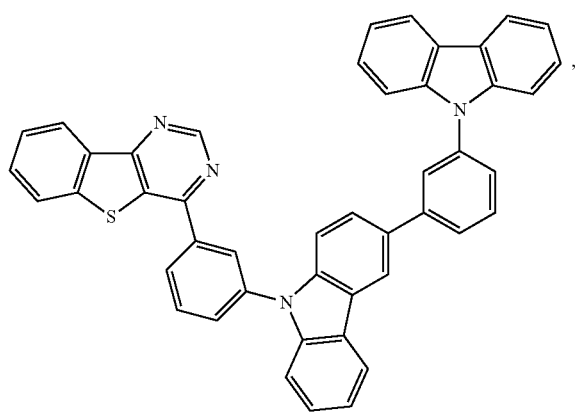
Compound 19141
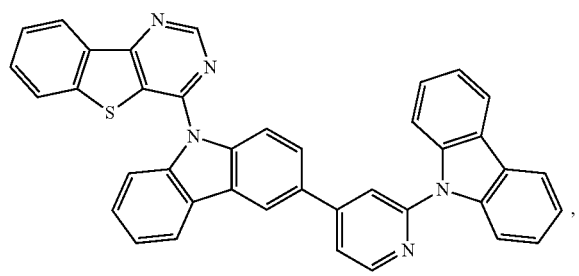
Compound 20881
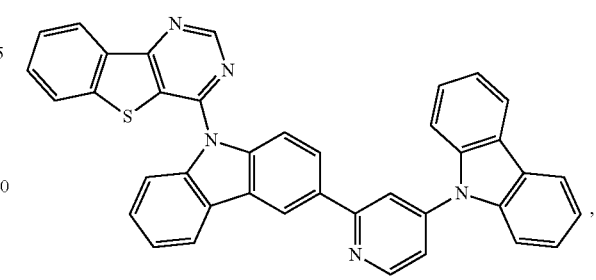
Compound 22621
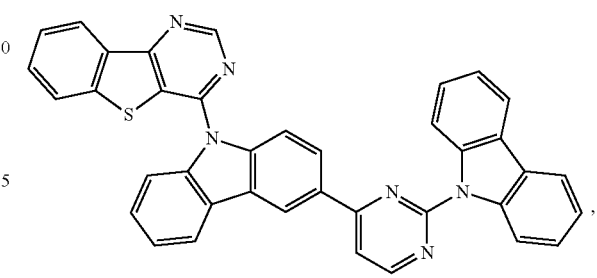
Compound 24361
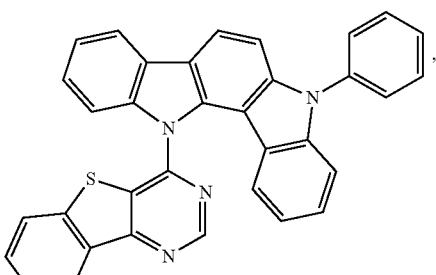
Compound 24362
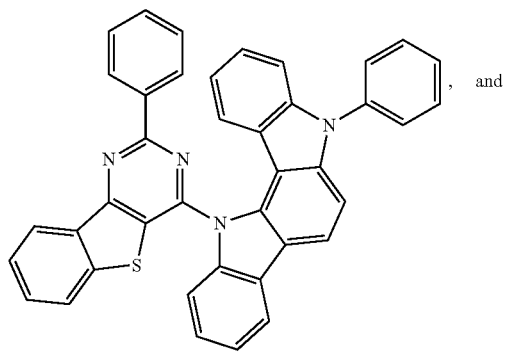
, and Compound 24477

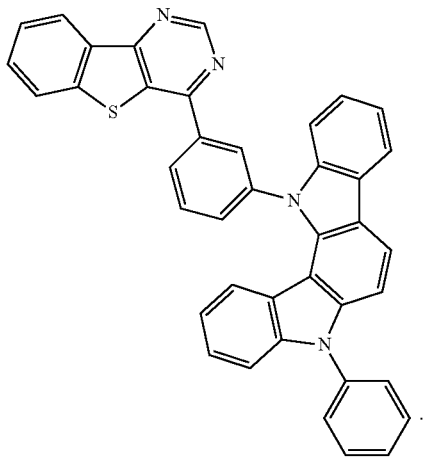

According to another aspect of the present disclosure, a first device comprising a first phosphorescent organic light-emitting device is disclosed. The phosphorescent organic light-emitting device comprises an anode, a cathode, and an organic layer disposed between the anode and the cathode. The organic layer comprises a compound having the formula $G^1$—L—$G^2$, Formula I;
wherein $G^1$ has the structure:

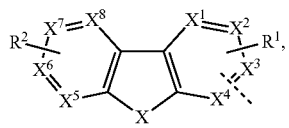

and
$G^2$ has the structure:

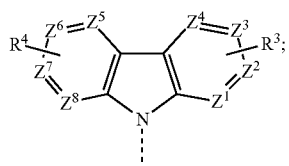

wherein L is selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein X is selected from the group consisting of O, S, and Se;
wherein each of $X^1$, $X^2$, $X^3$, $X^4$, $X^5$, $X^6$, $X^7$, $X^8$, $Z^1$, $Z^2$, $Z^3$, $Z^4$, $Z^5$, $Z^6$, $Z^7$, and $Z^8$ is carbon or nitrogen;
wherein at least two of $X^1$, $X^2$, $X^3$, $X^4$, $X^5$, $X^6$, $X^7$, and $X^8$ are nitrogen;
wherein at least one of $X^1$, $X^2$, $X^3$, and $X^4$ is carbon and bonded to L;
wherein the dashed lines represent the bonds between $G^1$ and L and between $G^2$ and L;
wherein each $R^2$, $R^3$, and $R^4$ represent mono, di, tri, tetra substitutions or no substitution;
wherein $R^1$ represents mono, di, tri substitutions or no substitution;
wherein $R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein the substitution is optionally fused to $G^1$ or $G^2$; and
wherein when $R^3$ or $R^4$ is carbazole or substituted carbazole, the carbazole or substituted carbazole is connected to $G^2$ by N.

In one embodiment of the first device, the organic layer is an emissive layer and the compound of Formula I is a host. In an embodiment, the organic layer further comprises a phosphorescent emissive dopant. In an embodiment, the phosphorescent emissive dopant is a transition metal complex having at least one ligand selected from the group consisting of:

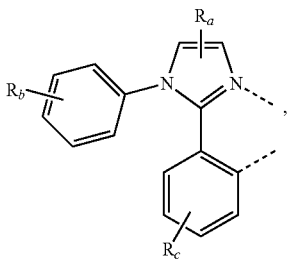

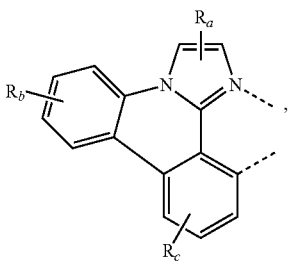

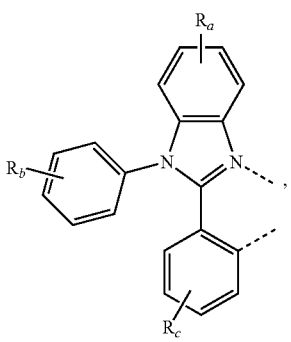

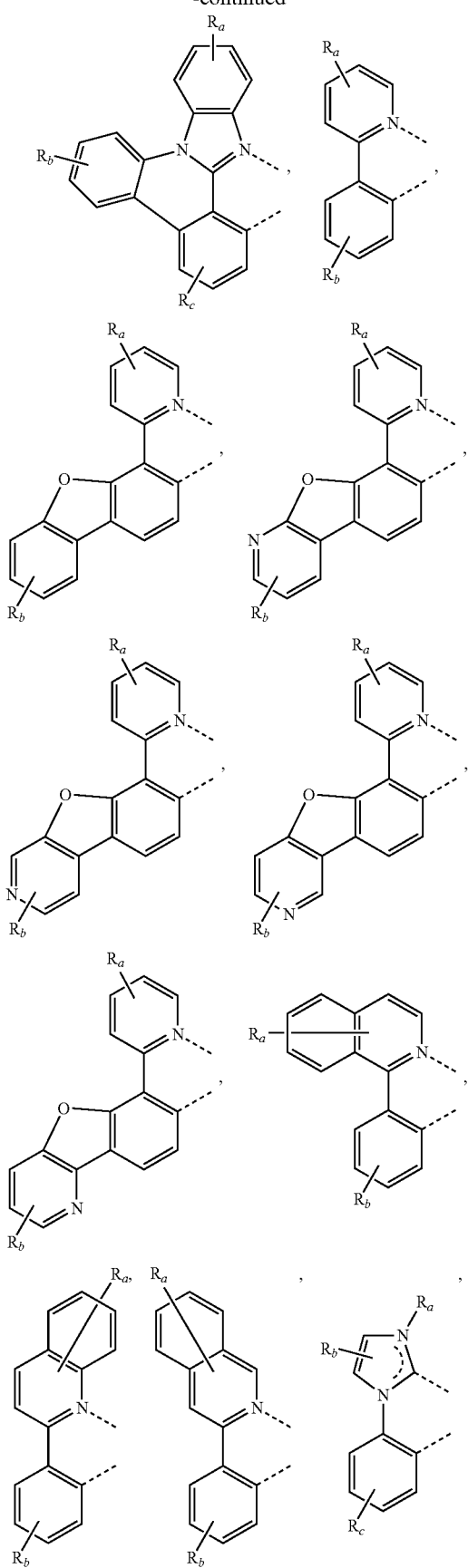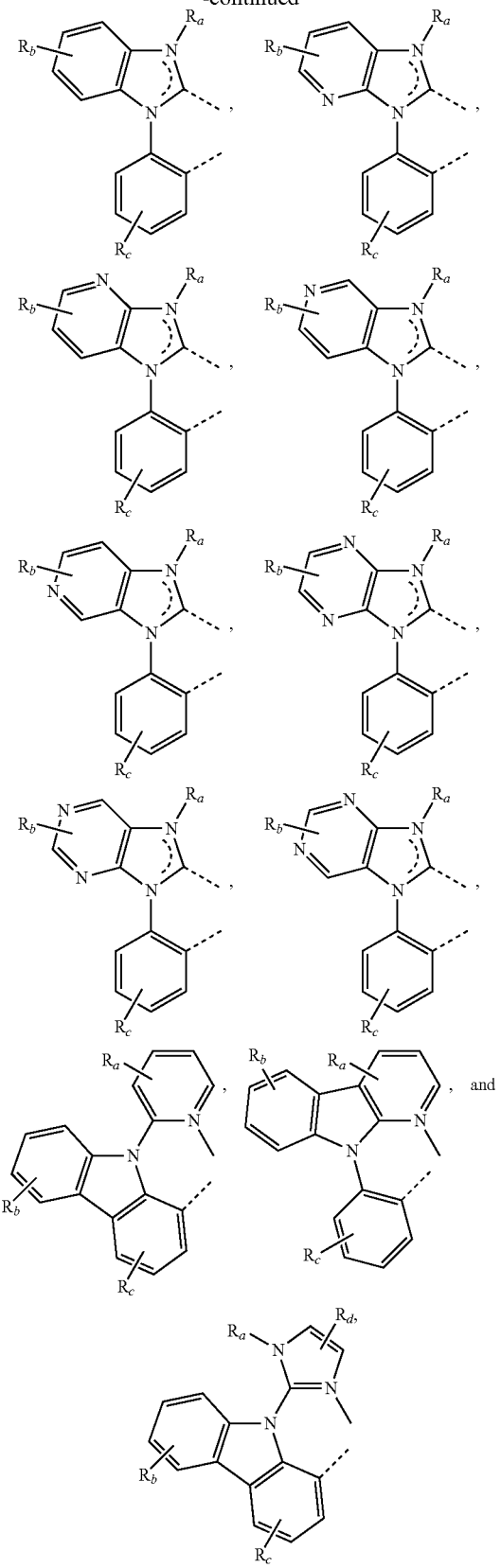
wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In one embodiment of the first device, the organic layer is a blocking layer and the compound is a blocking material in the organic layer. In another embodiment, the organic layer is an electron transporting layer and the compound is an electron transporting material in the organic layer.

In one embodiment of the first device, the first device is a consumer product. In another embodiment, the first device is an organic light-emitting device. In another embodiment, the first device can comprise a lighting panel.

According to another aspect of the present disclosure, a formulation comprising the compound having the formula $G^1$—L—$G^2$, Formula I, is disclosed, wherein $G^1$, L, and $G^2$ are as defined above.

The novel compounds described in this disclosure were used as electron-transporting hosts in the emissive layer of an organic light-emitting device. The molecules of the compounds have two parts: an electron rich part (the substituted or non-substituted carbazole) and an electron poor part (benzothienopyrimidines or benzofuropyrimidine). Such dual, bipolar, character of the novel compound improves their electron-conducting properties and, thus, the compounds are useful as electron-conducting hosts in red, green, yellow, and white OLED devices. Aza-debenzothiophenes and aza-dibenzofurans have been used as host materials in phosphorescent OLED devices, however, analogs with two N atoms in one cycle is not known. It is believed that two nitrogen atoms will further lower the LUMO level and provide better stabilized LUMO; as a result such molecules may be more stable to electrons and may have better electron-carrier properties than the analogs with one nitrogen atom. Synthetic approaches to such compounds were widely studied in organic chemistry for preparation of drugs and pesticides. Thus, one can synthesize a variety of diazadibenzothiophenes and diazadibenzofurans with different substituents. Such substituents allow tuning of electronic properties of the material (HOMO, LUMO, etc.) and their physicochemical properties such as $T_D$, $T_G$, etc.

Experimental Results

The inventors have verified the benefits of the inventive compounds disclosed herein by fabricating experimental OLED devices. Example devices were made using the inventive compounds Compound 3, Compound 45, Compound 6961, and Compound 24361 disclosed herein as the host material in the emissive layer. A comparative device was made using Comparison Compound 1 shown below:

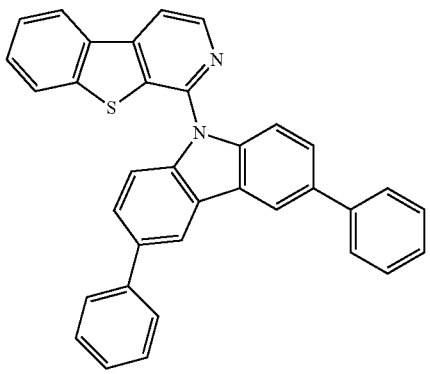

Comparison Compound 1

HAT-CN was used for hole injection layer ("HIL"). NPD was used for hole transporting layer ("HTL"). Alq$_3$ was used for electron transporting layer ("ETL").

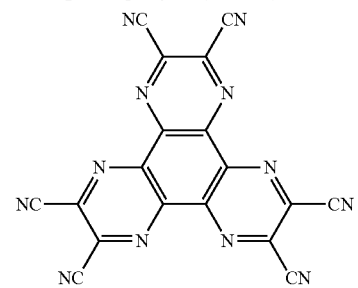

HIL(HAT-CN)

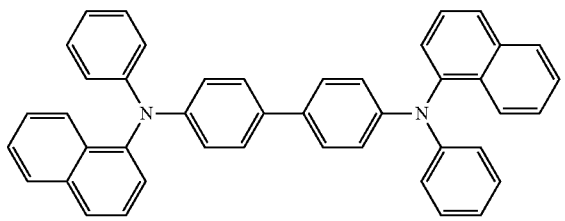

HTL (NPD)

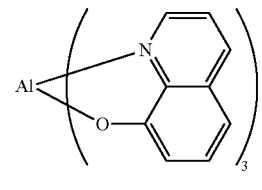

ETL (Alq$_3$)

The compounds used for the hole transporting co-host and red emitter in the emissive layer are shown below.

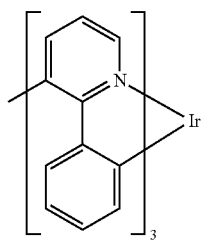

Compound H

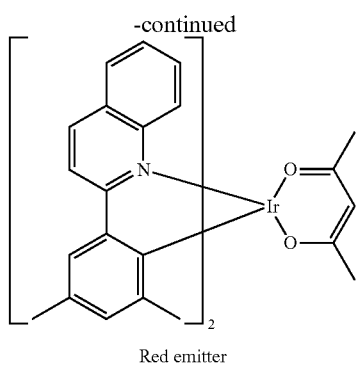

Red emitter

The organic stack of the Example devices and the Comparative device were fabricated with the following structure: from the ITO surface, 100 Å of HAT-CN as the hole injection layer (HIL), 400 Å of NPD as the hole transporting layer (HTL), 300 Å of the emissive layer (EML) which contains the Host (79%), Compound H (18%), and Red emitter (3%), 100 Å host compound as blocking layer, 550 Å of $Alq_3$ as the electron transporting layer (ETL) and 10 Å of LiF as the electron injection layer (EIL). The experimental device performance data is presented in Table 1 below.

TABLE 1

Device performances of the novel host compounds vs. Comparison Compound 1

| | | | 1931 CIE | | At 1,000 nits | | | At 80 mA/cm² | |
|---|---|---|---|---|---|---|---|---|---|
| | Host | BL | CIE x | CIE y | Voltage % | LE % | EQE % | $L_0$ % | LT95% % |
| Example Device 1 | Compound 3 | Compound 3 | 0.661 | 0.338 | 90 | 122 | 123 | 117 | 288 |
| Example Device 2 | Compound 45 | Compound 45 | 0.659 | 0.340 | 78 | 110 | 112 | 111 | 489 |
| Example Device 3 | Compound 6961 | Compound 6961 | 0.660 | 0.339 | 71 | 139 | 136 | 132 | 455 |
| Example Device 4 | Compound 24361 | Compound 24361 | 0.655 | 0.343 | 66 | 127 | 121 | 124 | 111 |
| Comparison Device | Comparison Compound 1 | Comparison Compound 1 | 0.654 | 0.343 | 100 | 100 | 100 | 100 | 100 |

Except for the 1931 CIE coordinates, Table 1 presents relative values using the Comparison Device as the reference, whose relative performance represents 100%. As one can see, all Example Devices 1-4 exhibited superior voltage, luminous efficiency (LE), and external quantum efficiency (EQE) at 1,000 nits. The device operation lifetime measurements were performed at a constant dc current of 80 mA/cm² at room temperature with light output monitored as a function of time. $L_0$ is the initial luminance of the operational lifetime measurement. The operational lifetimes defined at 95% of the initial luminance (LT95%) were shown in the table 1. All Example Devices 1-4 exhibited superior $L_0$ and LT95 compared to the comparison device.

Synthesis of the Comparison Compound 6961

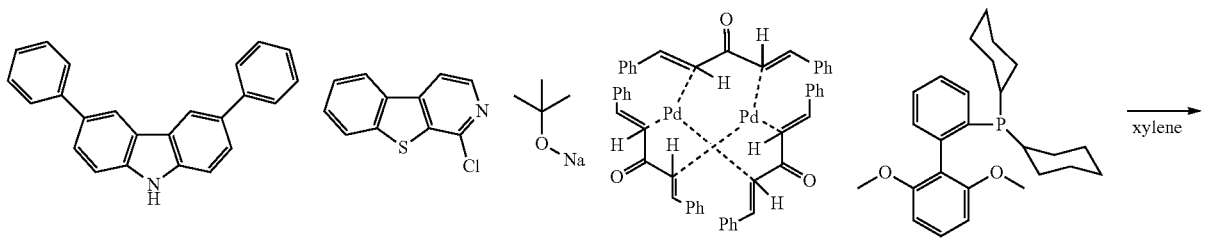

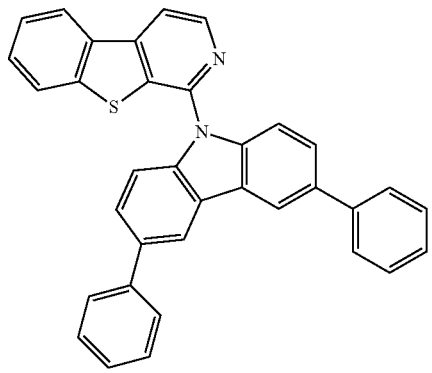

3,6-Diphenyl-9H-carbazole (2.000 g, 6.26 mmol) and 1-chlorobenzo[4,5]thieno[2,3-c]pyridine (1.376 g, 6.26 mmol) were dissolved in xylene (150 ml), then sodium 2-methylpropan-2-olate (1.204 g, 12.52 mmol), Pd$_2$(dba)$_3$ (120 mg) and dicyclohexyl(2',6'-dimethoxy-[1,1'-biphenyl]-2-yl)phosphine (0.129 g, 0.313 mmol) were added to the reaction solution. The reaction solution was degassed and heated to reflux under N$_2$ atm. overnight. Then it was cooled down to room temperature, filtered through celite pad and evaporated. The residue was subjected to column chromatography on silica gel, eluted with hexane/DCM 9/1 to 1/1 (v/v) gradient mixture, providing white solid, which was crystallized from hexane/DCM. 1-(3,6-Diphenyl-9H-carbazol-9-yl)benzo[4,5]thieno[2,3-c]pyridine to form white crystals of the Comparison Compound 6961 (2.7 g, 5.37 mmol, 86% yield).

Synthesis of the Novel Compound 3

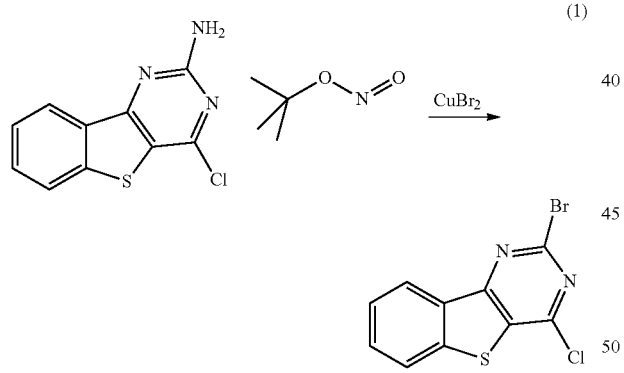

(1) Copper(II) bromide (11.30 g, 50.6 mmol) and tert-butyl nitrite (8.36 ml, 63.3 mmol) were suspended in 170 mL of acetonitrile and heated to 65° C. 4-Chlorobenzo[4,5]thieno[3,2-d]pyrimidin-2-amine (9.9 g, 42.2 mmol) was added in portions to the reaction solution over the course of 5 minutes and stirred for 30 minutes at 70° C. The reaction solution was cooled to room temperature, quenched with 1M HCl, then filtered and washed with water. The resulting solids were basified with 10% NaOH, extracted 5× with DCM. Acidic aqueous extracted 3× with DCM and combined with other organics. The organic layer was dried over sodium sulfate, filtered and concentrated. The concentrate was redissolved in CHCl$_3$, washed with 10% NaOH, dried filtered and concentrated to 9.4 g yellow solids. The yellow solids were purified by passing through a plug of Celite/silica with hot toluene then concentrated to 8.7 g (69%) of the 2-bromo-4-chlorobenzo[4,5]thieno[3,2-d]pyrimidine as yellow solid.

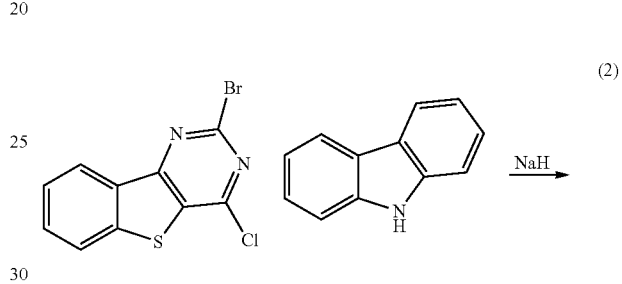

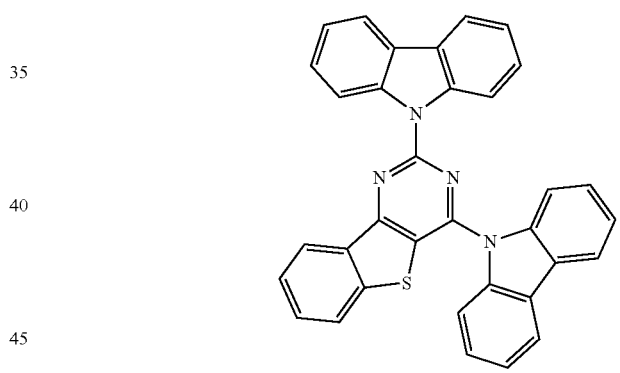

(2) A 250 mL RBF was dried under vacuum and charged with 9H-carbazole (2.79 g, 16.69 mmol) and anhydrous DMF (33 mL). Sodium hydride (0.801 g, 20.03 mmol) was added cautiously to the reaction solution, and stirred until the evolution of hydrogen had stopped. 2-bromo-4-chlorobenzo[4,5]thieno[3,2-d]pyrimidine (2.0 g, 6.68 mmol) was added in one portion to the reaction solution causing an immediate color change from yellow to red. After stirring for ~5 minutes the reaction solution became an unstirrable orange suspension then 15 mL of DMF was added to make a thick, stirrable suspension. After ~1 hr, the suspension was quenched with water, filtered and washed with water and EtOH, providing 3.25 g of the 2,4-di(9H-carbazol-9-yl)benzo[4,5]thieno[3,2-d]pyrimidine as off-white solids. The solids were recrystallized twice from toluene and dried in vacuo overnight at 50° C. provided 2.15 g (62% yield) of Compound 3.

Synthesis of the Novel Compound 45

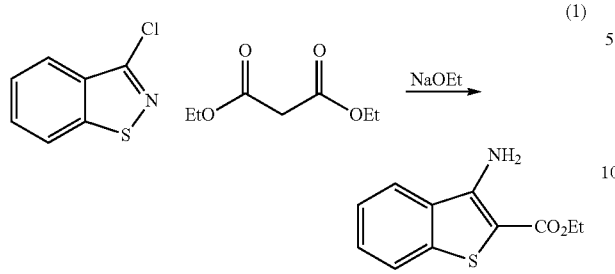

(1) A dry 2-neck 500 mL RBF was charged with 21% sodium ethanolate (46.2 ml, 124 mmol), diluted with 151 mL absolute EtOH, cooled in an ice bath and treated dropwise with diethyl malonate (18 mL, 118 mmol) under an atmosphere of nitrogen. After stirring for 20 minutes, the ice bath was removed and 3-chlorobenzo[d]isothiazole (20.0 g, 118 mmol) was added in one portion and stirred for 24 hours. The reaction solution was quenched with water, extracted with ether and treated with excess 4M HCl/dioxane. The resulting pinkish-white precipitate was filtered off, suspended in water, basified with $Na_2CO_3$, extracted with ether, washed with water and brine, dried over sodium sulfate, filtered and concentrated to yellow solids (~20 g) which were recrystallized from ethanol/water and dried in a vacuum oven at 60° C. for 3 hrs affording 19.9 g (76% yield) of the ethyl 3-aminobenzo[b]thiophene-2-carboxylate.

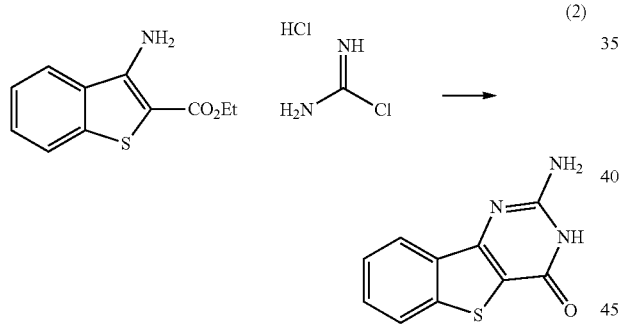

(2) Ethyl 3-aminobenzo[b]thiophene-2-carboxylate (10 g, 45.2 mmol), and carbamimidic chloride hydrochloride (7.27 g, 63.3 mmol) in diglyme (90 mL) were heated to 160° C. for 12 hrs. The reaction solution was cooled to room temperature, filtered, washed with ether and hexanes and dried in vacuo for 3 hrs yielding 10.56 g (108% yield) of crude grey solids of the 2-aminobenzo[4,5]thieno[3,2-d]pyrimidin-4(3H)-one. Used as is without further purification.

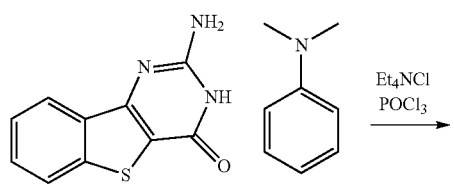

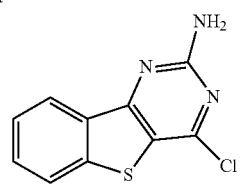

(3) In a 100 mL 3-neck RBF 2-aminobenzo[4,5]thieno[3,2-d]pyrimidin-4(3H)-one (15.30 g, 70.4 mmol) and tetraethylammonium chloride (23.34 g, 141 mmol) were dried under vacuum at 100° C. overnight. Cooled to room temperature and treated with acetonitrile (141 ml) followed by N,N-dimethylaniline (8.9 ml, 70.4 mmol) and phosphoryl trichloride (39.4 ml, 423 mmol). The reaction solution was heated to 110° C. for 15 minutes then cooled to room temperature, transferred to a 500 mL RBF and concentrated on the rotovap. Quenched with addition of ice, and pH adjusted to 7-8 with $NaHCO_3$ and filtered. Solids washed with water and ether, mascerated with water and filtered, washed with ether and dried in oven overnight yielding 9.4 g (57% yield) of the 4-chlorobenzo[4,5]thieno[3,2-d]pyrimidin-2-amine.

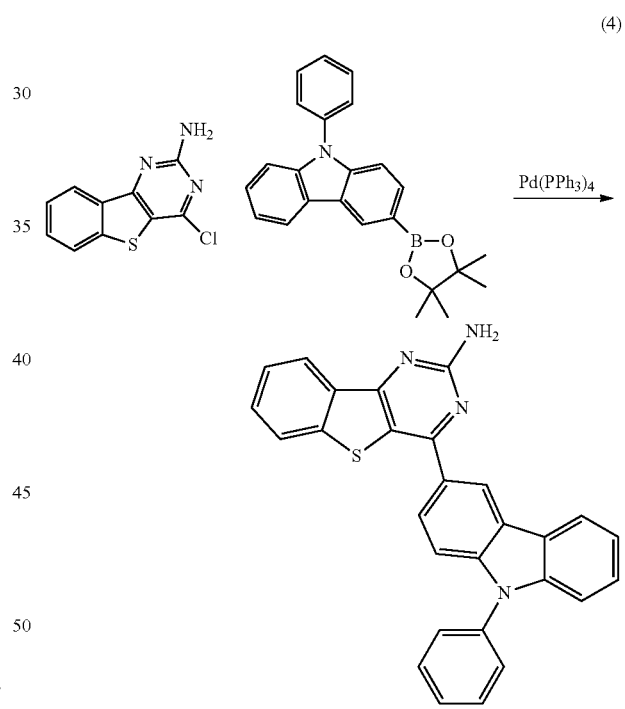

(4) 4-Chlorobenzo[4,5]thieno[3,2-d]pyrimidin-2-amine (2.0 g, 8.49 mmol), 9-phenyl-3-(4,4,5,5-tetramethyl-1,3,2-dioxaborolan-2-yl)-9H-carbazole (3.45 g, 9.33 mmol), Pd(PPh3)4 (0.588 g, 0.509 mmol) in THF (22.63 ml), and 2M $Na_2CO_3$ (11.3 ml) were degassed with nitrogen and heated to reflux at 75° C. overnight. The reaction solution was quenched with water, extracted 5× with $CHCl_3$, dried over sodium sulfate, and filtered and concentrated to yield orange solids. The orange solids were triturated in ~150 mL boiling EtOH and toluene at room temperature afforded 2.65 g (71% yield) of the 4-(9-phenyl-9H-carbazol-3-yl)benzo[4,5]thieno[3,2-d]pyrimidin-2-amine.

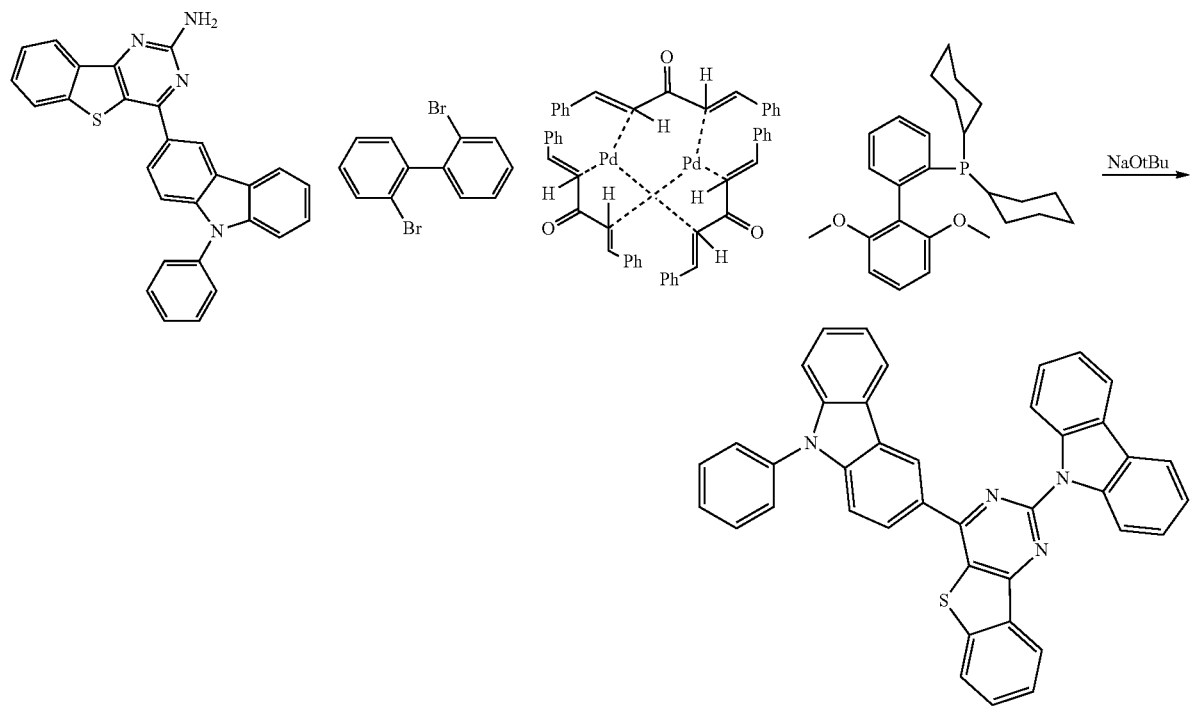

(5) 4-(9-Phenyl-9H-carbazol-3-yl)benzo[4,5]thieno[3,2-d]pyrimidin-2-amine (1.0 g, 2.260 mmol), 2,2'-dibromo-1,1'-biphenyl (0.705 g, 2.260 mmol), Pd(0)2dba3 (0.103 g, 0.113 mmol), dicyclohexyl(2',6'-dimethoxy-[1,1'-biphenyl]-2-yl)phosphine (0.186 g, 0.452 mmol), and sodium 2-methylpropan-2-olate (0.543 g, 5.65 mmol) were suspended in xylene (50 mL), degassed with nitrogen and heated to reflux overnight. Then the reaction solution was cooled down to room temperature and filtered through a plug of Celite, then washed with hot THF and CHCl₃, and the combined organic solutions were concentrated to orange/brown solids. The solids were dissolved in hot toluene, and filtered through a plug of deactivated alumina yielding a red clear filtrate. The filtrate was concentrated to solids and recrystallized from toluene/ethanol affording 1.8 g of the 2-(9H-carbazol-9-yl)-4-(9-phenyl-9H-carbazol-3-yl)benzo[4,5]thieno[3,2-d]pyrimidine as yellow solids, the Compound 45.

Synthesis of the Novel Compound 1588

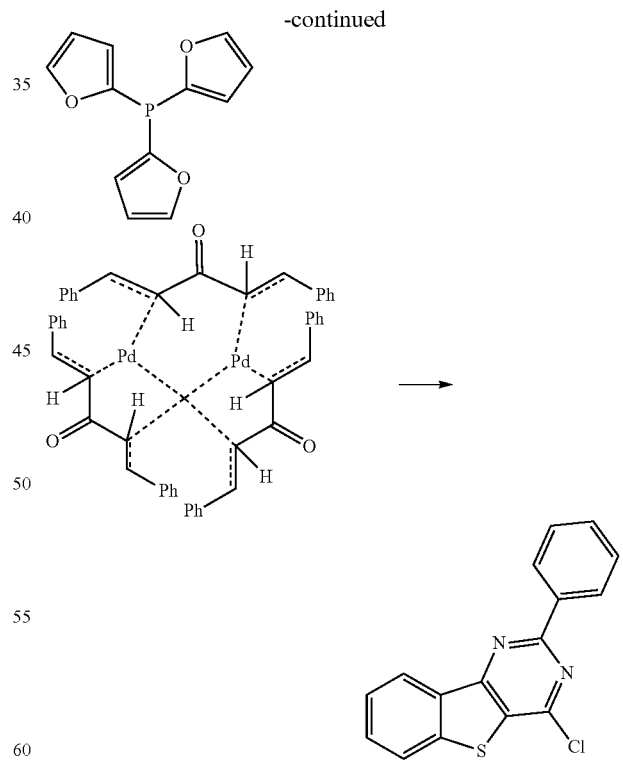

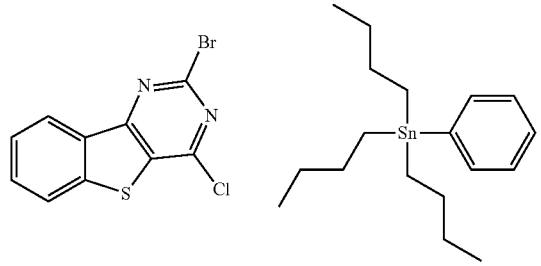

(1) 2-Bromo-4-chlorobenzo[4,5]thieno[3,2-d]pyrimidine (15 g, 50.1 mmol), tri(furan-2-yl)phosphine (2.325 g, 10.01 mmol), Pd2dba3 (1.146 g, 1.252 mmol) were dissolved in DMF (295 ml) and degassed by swing purging with nitrogen. Tributyl(phenyl)stannane (17.98 ml, 55.1 mmol) was added in one portion and the reaction was heated to 60° C. After 24 hrs the reaction solution was cooled in an ice bath, filtered and washed with ethanol and heptanes. Gray solids were dissolved in hot DCM and filtered through a plug of Celite/deactivated alumina with DCM to remove color. The filtrate was concentrated to provide 11 g (74%) of 4-chloro-2-phenylbenzo[4,5]thieno[3,2-d]pyrimidine as white solid.

(2)

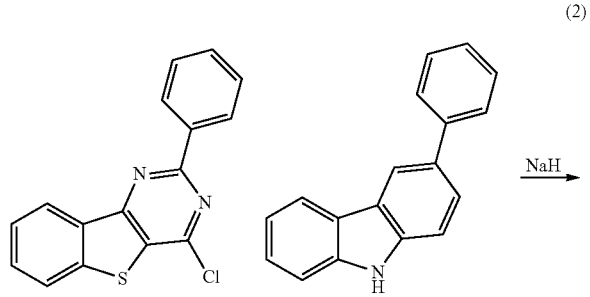

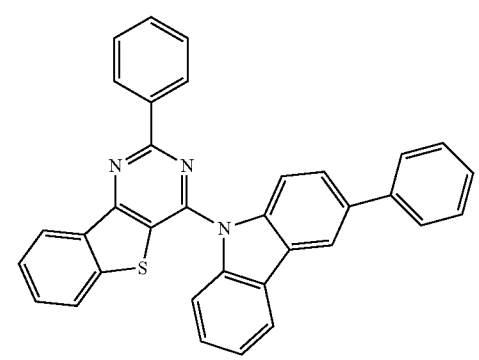

(2) A 100 mL RBF was dried under vacuum and charged with 3-phenyl-9H-carbazole (2.306 g, 9.48 mmol) and DMF (40 mL). Sodium hydride (0.531 g, 13.27 mmol) (60% in oil) was added to the reaction solution, and stirred until the evolution of hydrogen had stopped. 4-Chloro-2-phenyl-benzo[4,5]thieno[3,2-d]pyrimidine (2.25 g, 7.58 mmol) was added in one portion to the reaction solution and stirred overnight at room temperature. The reaction solution was quenched with water, filtered and solid precipitate was washed with water and EtOH. Solids were triturated twice in EtOH, then recrystallized from hot toluene providing 2.9 g (76% yield) of Compound 1742.

Synthesis of the Novel Compound 6961

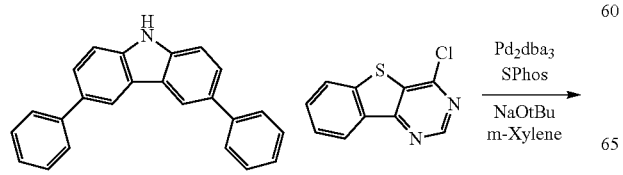

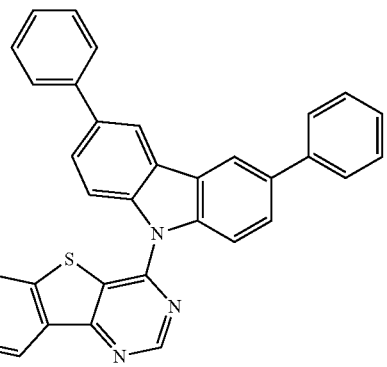

3,6-Diphenyl-9H-carbazole (3.0 g, 9.39 mmol), 4-chlorobenzo[4,5]thieno[3,2-d]pyrimidine (2.280 g, 10.33 mmol), sodium 2-methylpropan-2-olate (2.257 g, 23.48 mmol), Pd$_2$dba$_3$ (0.430 g, 0.470 mmol), and dicyclohexyl (2',6'-dimethoxy-[1,1'-biphenyl]-2-yl)phosphine (SPhos) (0.386 g, 0.939 mmol) were charged into a 250-mL round-bottom-flask (RBF), diluted in m-xylene (94 ml), degassed and heated to reflux overnight. Then the mixture was cooled down to room temperature and was diluted by DCM, filtered through a pad of Celite and washed with DCM. The solvent was evaporated and the crude solid was purified by column chromatography on silica, eluted with 30-50% DCM in heptanes gradient mixture, then by 50/45/5 (v/v/v) DCM/heptanes/ethyl acetate mixture. After evaporation of the solvent, the yellow solid is triturated in methanol, then the solid was crystallized from heptanes/toluene mixture to provide 1.4 g of the pure Compound 1 (4-(3,6-diphenyl-9H-carbazol-9-yl)benzo[4,5]thieno[3,2-d]pyrimidine).

Synthesis of the Novel Compound 6962

(1)

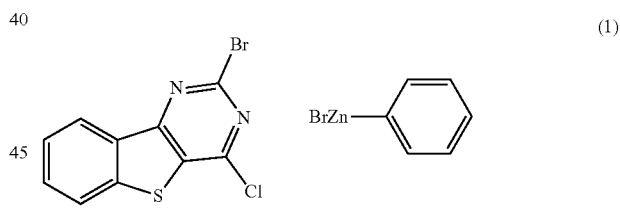

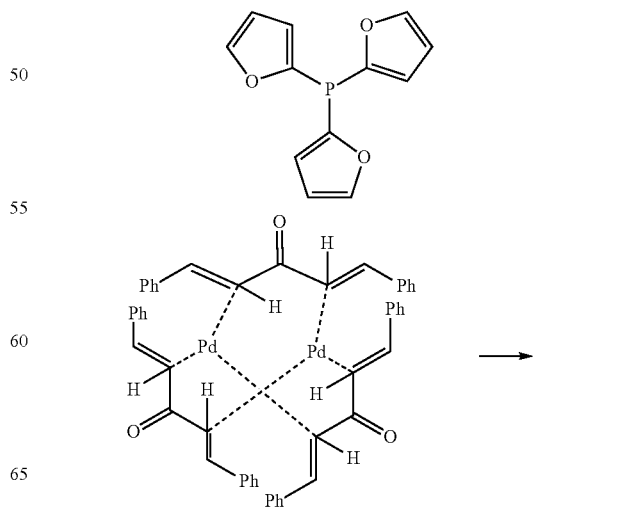

-continued

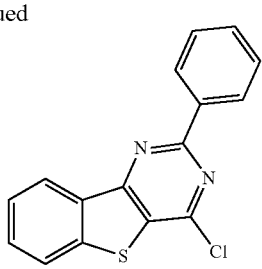

(1) 2-Bromo-4-chlorobenzo[4,5]thieno[3,2-d]pyrimidine (2.5 g, 8.35 mmol), tri(furan-2-yl)phosphine (0.194 g, 0.835 mmol), Pd2dba3 (0.191 g, 0.209 mmol) were dissolved in THF (50 mL) and degassed with nitrogen. The reaction solution was heated to 60° C. for 15 minutes, and then phenylzinc(II) bromide (25 mL, 12.52 mmol) was added dropwise. The reaction solution was heated at 60° C. for 2 hrs. An aliquot analyzed by GCMS indicated 13% starting material and 87% of the desired product. 3.8 mL phenylzinc (II) bromide added dropwise to the reaction solution and heating continued overnight. The reaction solution was cooled to room temperature, extracted with DCM, washed with water, dried over sodium sulfate and concentrated in vacuo. The material was purified by column chromatography on silica, eluted with 10-20% DCM/heptanes gradient mixture. The solids were recrystallized from DCM/heptanes affording 0.9 g (36% yield) of the title compound as white needle crystals.

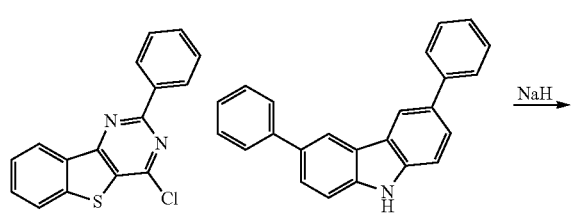

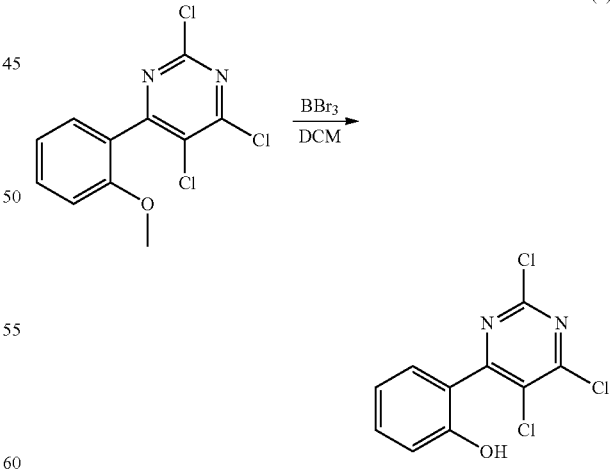

(2) 3,6-Diphenyl-9H-carbazole (1.117 g, 3.50 mmol) was dissolved in DMF (15 mL) and a 60% dispersion of sodium hydride (0.168 g, 4.20 mmol) was added as one portion. The reaction solution was stirred under nitrogen for 30 minutes at room temperature, then 4-chloro-2-phenylbenzo[4,5]thieno[3,2-d]pyrimidine (0.83 g, 2.80 mmol) was added in one portion and stirring continued at room temperature for 2 hrs. The reaction solution was quenched with water, filtered and triturated three times with EtOH. The product was recrystallized from toluene/EtOH yielding 1.1 g (68%) of the title compound 99.9% pure.

Synthesis of the Novel Compound 6987

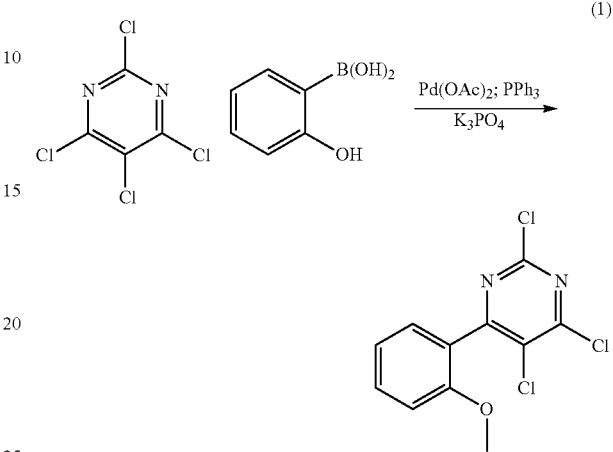

(1) A mixture of perchloropyrimidine (15 g, 65.4 mmol), (2-methoxyphenyl)boronic acid (10.14 g, 65.4 mmol), triphenylphosphine (1.716 g, 6.54 mmol), palladium acetate (0.734 g, 3.27 mmol) and potassium phosphate, H2O (45.2 g, 196 mmol) in acetonitrile (300 ml)/water (90 ml) was degassed at room temperature. The mixture was stirred at room temperature for 1 hr. before heated at 60° C. for 1 hr. Upon completion of the reaction, the reaction was diluted with ethyl acetate, washed with sodium chloride saturated solution, filtered and evaporated. The crude material was purified by silica gel column chromatography using heptanes/AcOEt: 93/7 to 8/2 as eluent to afford a white solid (10.6 g, 56% yield).

(2) Tribromoborane (84 ml, 84 mmol) was added into a 0° C., stirred solution of 2,4,5-trichloro-6-(2-methoxyphenyl) pyrimidine (10.6 g, 36.6 mmol) in CH2Cl2 (330 ml) under N2 over a period of 1 hr. The mixture was warmed up and stirred at 20° C. overnight. The reaction solution was poured slowly into the ice water with stirring. Aqueous mixture was extracted with ethyl acetate (75 mL×2 times). Organic solution was washed with water, aqueous NaHCO₃, water and brine, and then dried over anhydrous Na₂SO₄. The crude material was purified by silica gel column chromatography eluted with heptane/ethyl acetate 92/8 to 8/2 gradient mixture to afford 2-(2,5,6-trichloropyrimidin-4-yl)phenol as yellow solid (7.3 g, 72.4% yield).

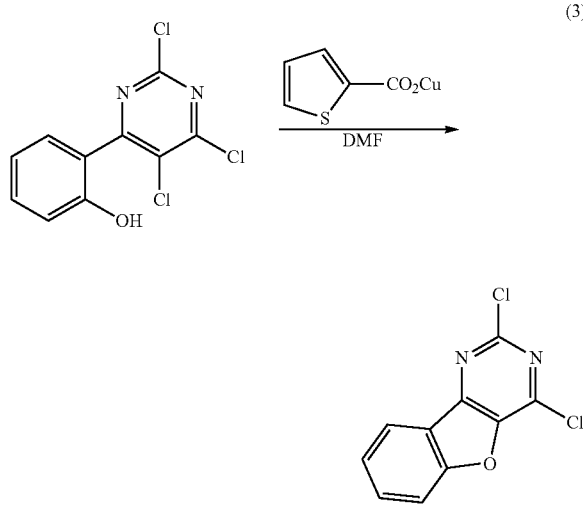

(3) A mixture of 2-(2,5,6-trichloropyrimidin-4-yl)phenol (6.5 g, 23.59 mmol) and ((thiophene-2-carbonyl)oxy)copper silica gel column chromatography eluted with heptane/ethyl acetate 95/5 to 9/1 gradient mixture to afford a yellow sold (1.43 g 25.4% yield).

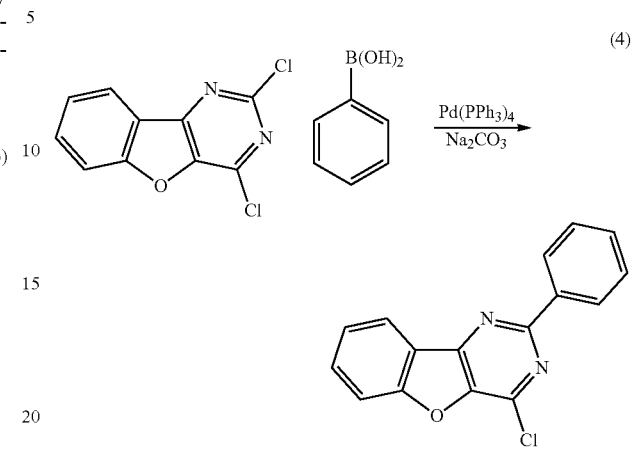

(4) A mixture of phenylboronic acid (1.530 g, 12.55 mmol), 2,4-dichlorobenzofuro[3,2-d]pyrimidine (3.0 g, 12.55 mmol) and sodium carbonate (2.66 g, 25.10 mmol) in THF (120 ml)/water (24 mL) was degassed for 20 min, then Pd(PPh₃)₄ (0.435 g, 0.376 mmol) was added and the mixture was heated at 60° C. under N₂ overnight. Upon completion, organic phase was separated and evaporated. The crude was purified by silica gel column chromatography with heptane/DCM/ethyl acetate 7/3/0.2 to 4/6/0.2 (v/v/v) as eluent to afford a yellow solid (2.0 g, 56.8% yield).

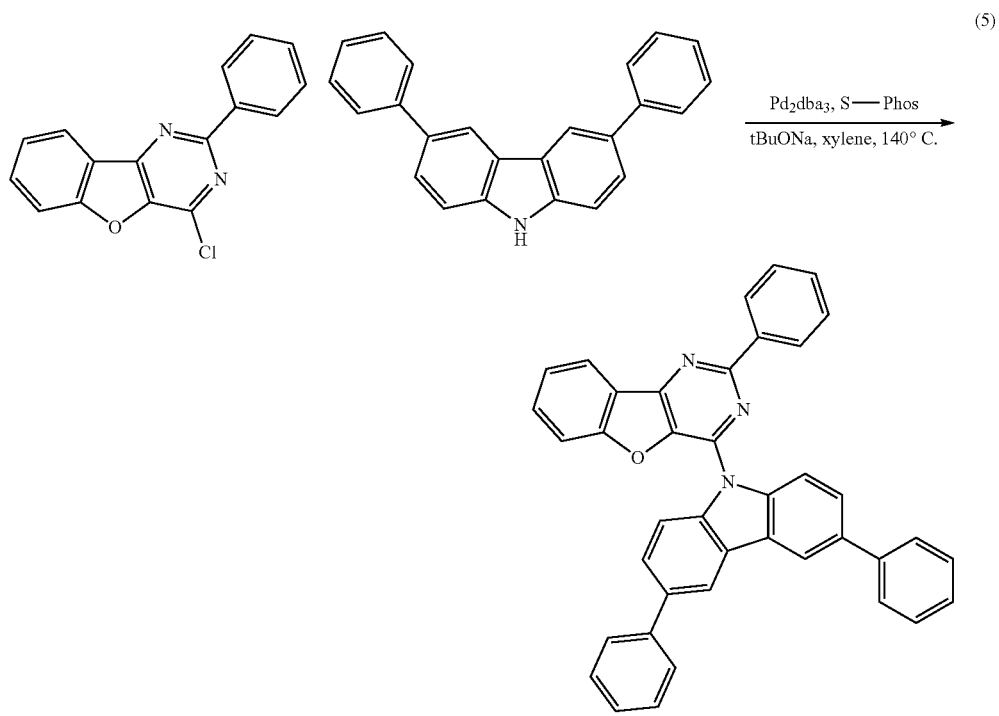

(5.40 g, 28.3 mmol) in DMF (130 ml) was heated at 100° C. for 2.5 hours. The reaction was cooled down and filtered through a bed of Celite. Water was added and the light green solid was filtered off. This crude material was purified by (5) A mixture of 4-chloro-2-phenylbenzofuro[3,2-d]pyrimidine (2 g, 7.12 mmol), 3,6-diphenyl-9H-carbazole (2.276 g, 7.12 mmol) and sodium 2-methylpropan-2-olate (1.369 g, 14.25 mmol) in xylene (120 mL) was degassed, then Pd₂

(dba)₃ (0.130 g, 0.142 mmol) and dicyclohexyl(2',6'-dimethoxy-[1,1'-biphenyl]-2-yl)phosphine (SPhos) (0.234 g, 0.570 mmol) were then added and heated at 140° C. overnight. The reaction solution was purified by silica gel column chromatography using heptane/DCM/ethyl acetate 80/20/2 to 4/6/0.2 (v/v/v) gradient mixture to afford Compound 6987 as a light yellow solid. (1.25 g, 31.1%).

Synthesis of the Novel Compound 15661

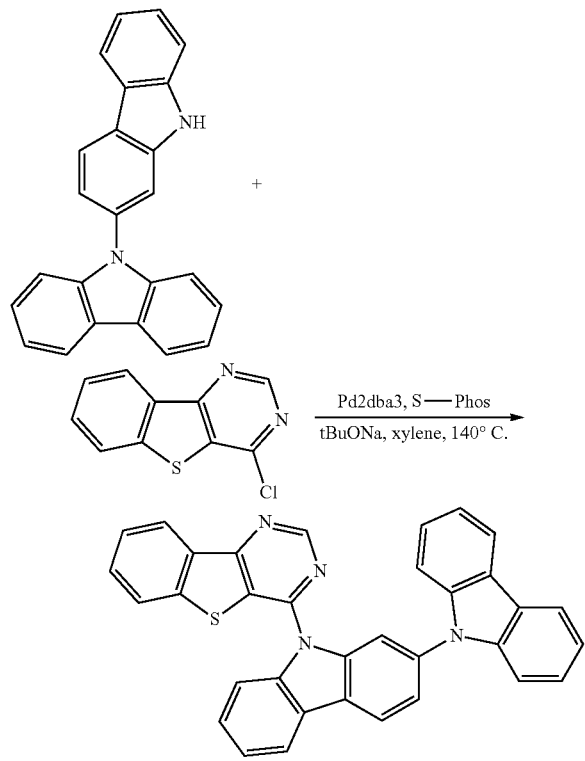

A mixture of 4-chlorobenzo[4,5]thieno[3,2-d]pyrimidine (3.09 g, 13.99 mmol), 9H-2,9'-bicarbazole (3.1 g, 9.33 mmol), sodium 2-methylpropan-2-olate (1.793 g, 18.65 mmol), Pd₂(dba)₃ (0.342 g, 0.373 mmol) and dicyclohexyl (2',6'-dimethoxy-[1,1'-biphenyl]-2-yl)phosphine (S-Phos, 0.613 g, 1.492 mmol) in 140 mL of xylene was degassed for 30 min. and the reaction mixture was heated to reflux under nitrogen atmosphere overnight. Upon completion, the reaction cooled down to room temperature, and solid material was filtered off. Then it was dissolved in hot toluene, filtered and evaporated. The crude material was recrystallized from DCM and DCM/THF to afford a yellow solid (1.8 g, 37.4% yield).

Synthesis of the Novel Compound 24361

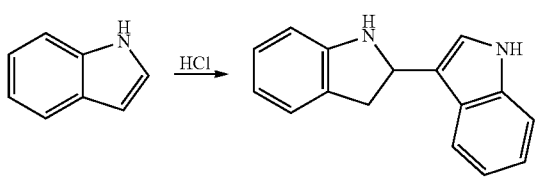

(1) A dry 500 mL RBF was charged with 1H-indole (29.0 g, 248 mmol) and ether (165 ml). The mixture was cooled to −20° C. and treated with 2M HCl in ether (260 ml, 520 mmol) over the course of 30 minutes. The cooling bath was removed and the reaction solution was stirred at room temperature for 24 hours. The reaction solution was filtered to get white powder and washed with ether. The solid was then washed with NaHCO₃ aq. and extracted with EtOAc. The solid was then washed with saturated NaHCO₃ and brine, dried over Na₂SO₄, filtered, and concentrated to afford 30.9 g of the 3-(indolin-2-yl)-1H-indole as clear, pink, viscous oil.

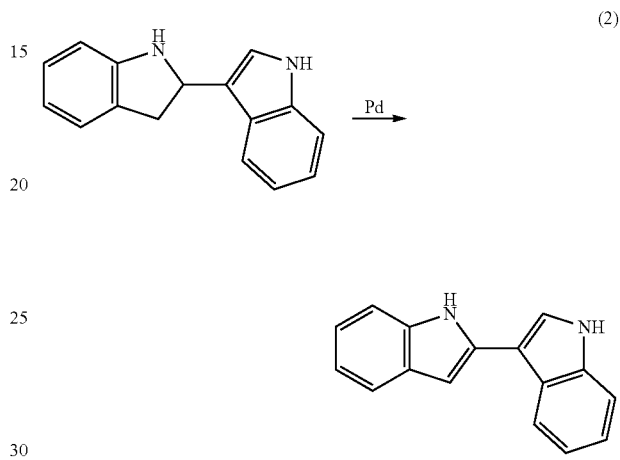

(2) 3-(Indolin-2-yl)-1H-indole (29 g, 124 mmol) in toluene (248 ml) was treated with 10 wt. % palladium (3.29 g, 3.09 mmol) on carbon. The reaction was heated to reflux at 115° C. for 3 hrs. The suspension was filtered hot, through a plug of Celite, which was then extracted 5× with hot toluene. The filtrate was concentrated in vacuo to half volume, cooled to room temperature and filtered to afford pink solids. The pink solids were washed with toluene and hexanes and dried in vacuo at 50° C. yielding 16.4 g (57% yield) of the 1H,1'H-2,3'-biindole as off-white solid.

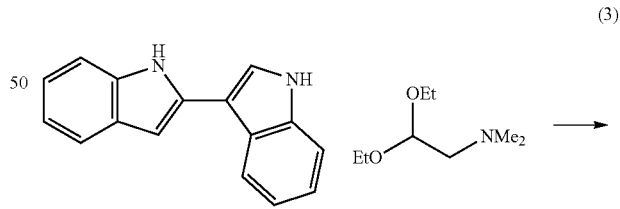

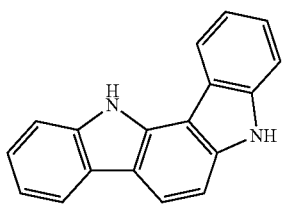

(3) 1H,1'H-2,3'-biindole (16.4 g, 70.6 mmol) and 2,2-diethoxy-N,N-dimethylethanamine (14.18 ml, 78 mmol) in glacial acetic acid (160 mL) were refluxed at 130° C. overnight under nitrogen. The reaction solution was cooled to room temperature and filtered. The filtrate was washed with small amount of acetic acid and excess of water. The filtrate was dried in the oven at 65° C. overnight affording 10.79 g (60%) of the 5,12-dihydroindolo[3,2-a]carbazole as gray solid.

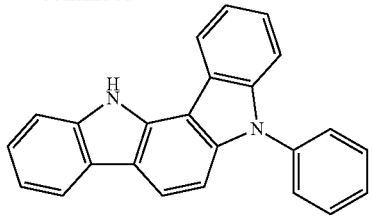

(4) Iodobenzene (2.278 ml, 20.39 mmol) and cyclohexane-1,2-diamine (0.901 ml, 3.71 mmol) were added to a degassed suspension of 5,12-dihydroindolo[3,2-a]carbazole (4.75 g, 18.53 mmol), copper(I) iodide (0.353 g, 1.853 mmol) and $K_3PO_4$ (8.26 g, 38.9 mmol) in m-xylene (93 ml). The reaction solution was refluxed at 155° C. for 48 hours. Based on TLC analysis after 24 hrs the reaction was not complete; the reaction mixture was cooled to room temperature, treated with more CuI (0.35 g) and cyclohexane-1,2-diamine (0.9 mL) and heated to reflux overnight. The suspension was filtered through Celite with THF and DCM. The filtrate was concentrated and purified by column chromatography with hexane: DCM gradient mixture (4:1 to 1:1 v/v). The filtrate was evaporated and dried in vacuo yielding 6.02 g (98% yield) of the 5-phenyl-5,12-dihydroindolo[3,2-a]carbazole as white solid.

(4)

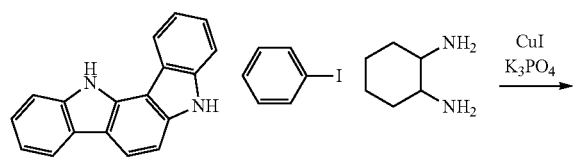

(5)

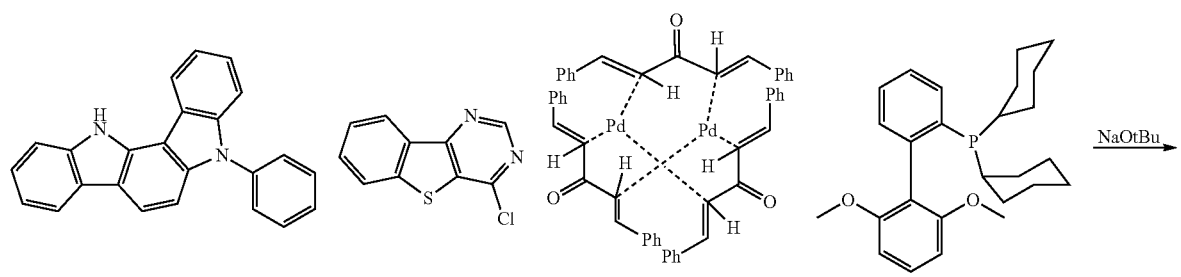

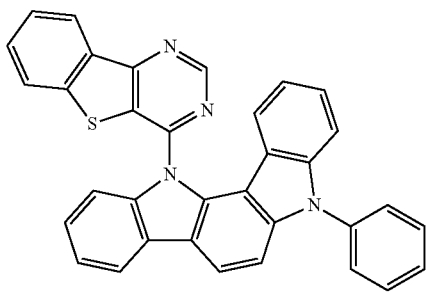

(5) 5-Phenyl-5,12-dihydroindolo[3,2-a]carbazole (2.83 g, 8.51 mmol), 4-chlorobenzo[4,5]thieno[3,2-d]pyrimidine (3.29 g, 14.90 mmol), Pd$_2$dba$_3$ (0.390 g, 0.426 mmol), dicyclohexyl(2',6'-dimethoxy-[1,1'-biphenyl]-2-yl)phosphine (0.699 g, 1.703 mmol), sodium 2-methylpropan-2-olate (2.046 g, 21.28 mmol) were suspended in xylene (120 mL), degassed with nitrogen, then heated to reflux at 155° C. overnight. After 15 hrs, additional 0.2 g of Pd$_2$dba3 and 0.35 g of dicyclohexyl(2',6'-dimethoxy-[1,1'-biphenyl]-2-yl) phosphine were added. The suspension was degassed with nitrogen and heated to reflux at 155° C. for 24 hrs. The reaction was filtered through a plug of Celite and evaporated. The residue was purified by column chromatography eluted with 20% DCM, 5% EtOAc in heptanes. Fractions containing product were further purified by trituration in EtOH and recrystallized from toluene/heptanes to provide 2.5 g of Compound 24361.

Synthesis of the Novel Compound 13361

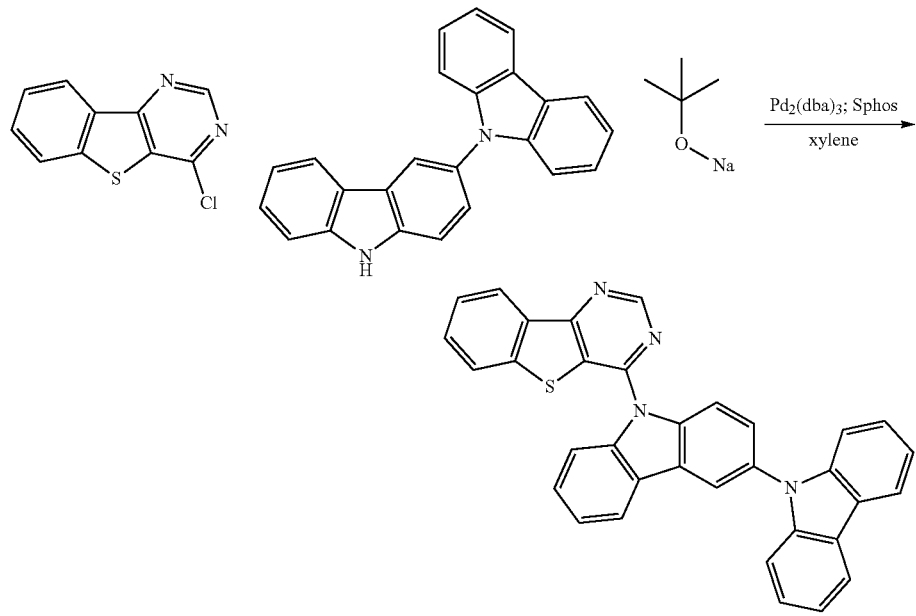

4-Chlorobenzo[4,5]thieno[3,2-d]pyrimidine (1.992 g, 9.03 mmol) and 9H-3,9'-bicarbazole (2.000 g, 6.02 mmol), sodium 2-methylpropan-2-olate (1.156 g, 12.03 mmol), Pd2 (dba)3 (250 mg) and dicyclohexyl(2',6'-dimethoxy-[1,1'-biphenyl]-2-yl)phosphine (SPhOS) (310 mg) were suspended in xylene (100 ml), degassed and heated to reflux for 18 hr. The reaction solution was cooled down, filtered through celite plug and evaporated. Column chromatography on silica gel column, eluted with hexane/DCM 1/1 (v/v), then hexane/EtOAc 4/1 (v/v), followed by crystallization from hexane/DCM provided yellow crystals (2.8 g, 90% yield).

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

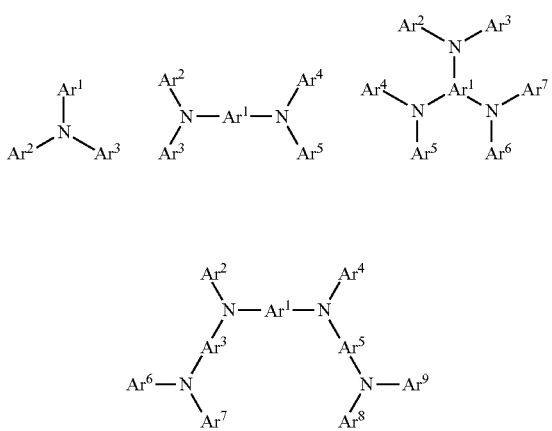

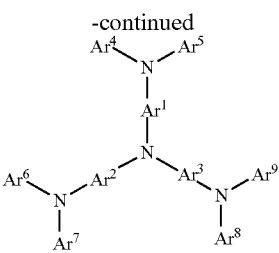

Each of Ar[1] to Ar[9] is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, Ar[1] to Ar[9] is independently selected from the group consisting of:

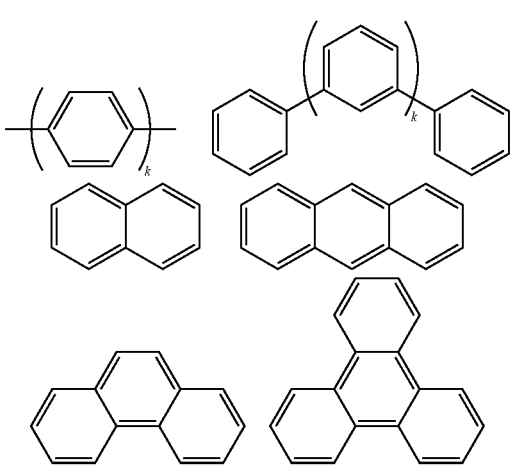

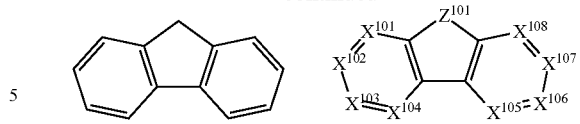

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

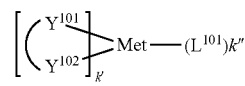

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+$/Fc couple less than about 0.6 V. Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

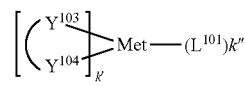

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

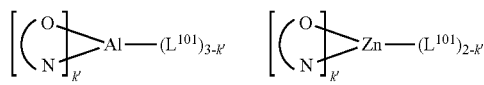

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

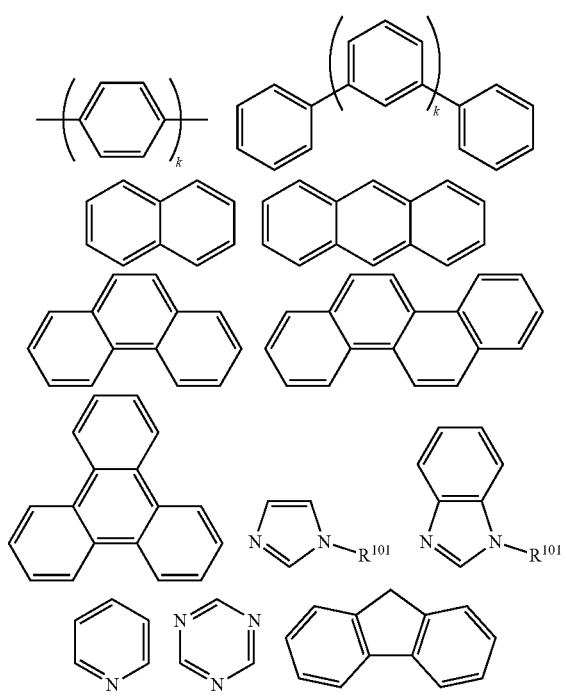

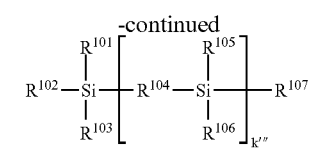

-continued

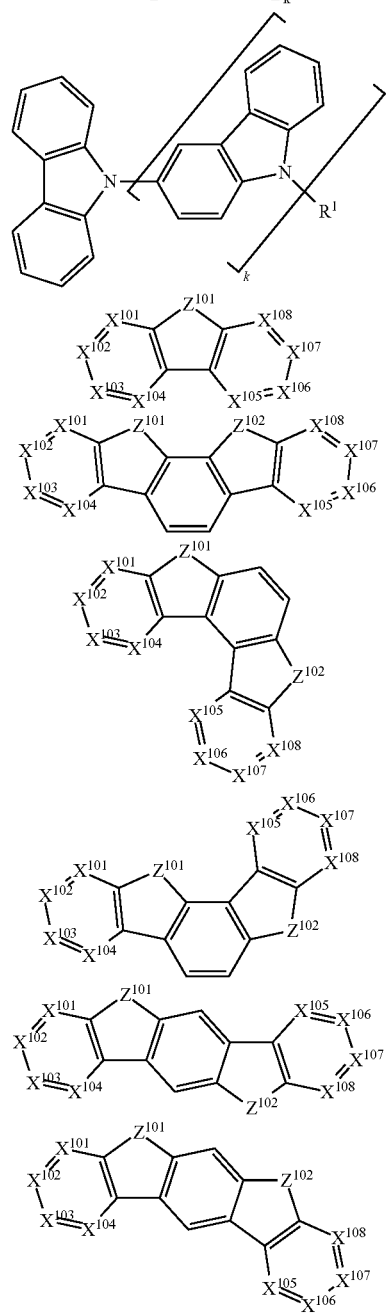

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

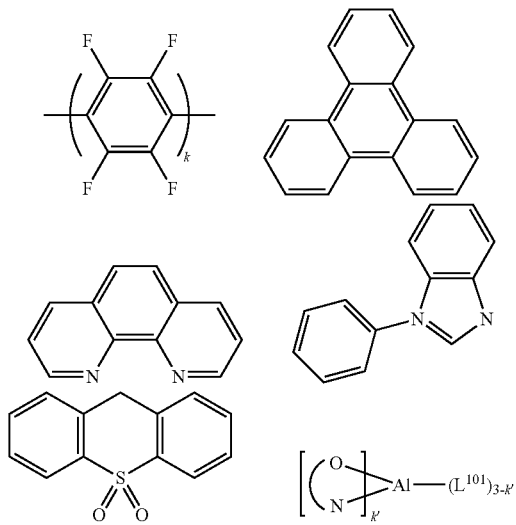

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

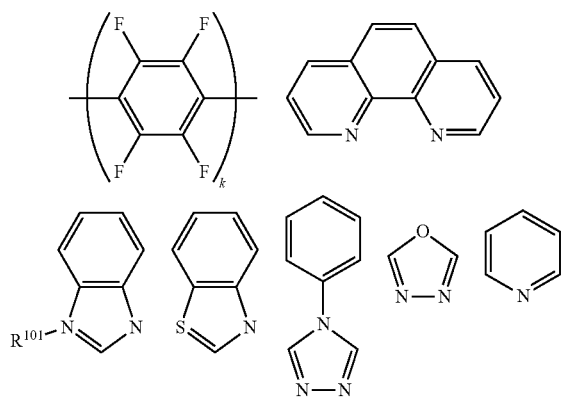

-continued

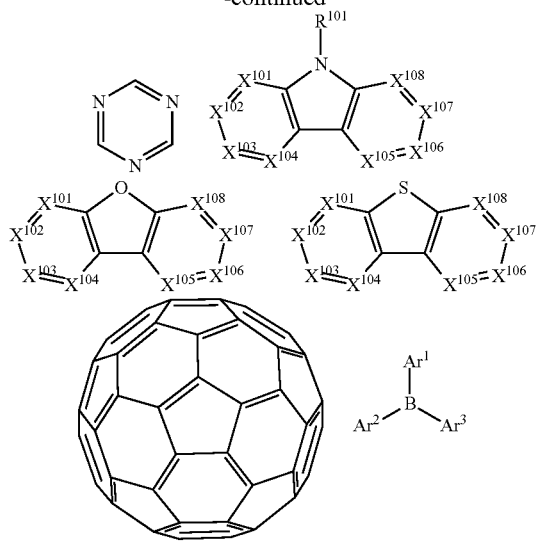

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

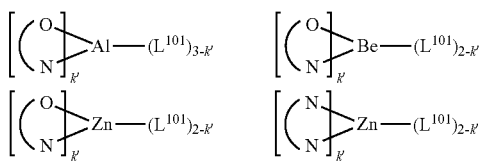

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |
| Phosphonic acid and sliane SAMs | | US20030162053 |

TABLE 2-continued
| MATERIAL | EXAMPLES OF MATERIAL | PUBLICATIONS |
|---|---|---|
| Triarylamine or polythiophene polymers with conductivity dopants | 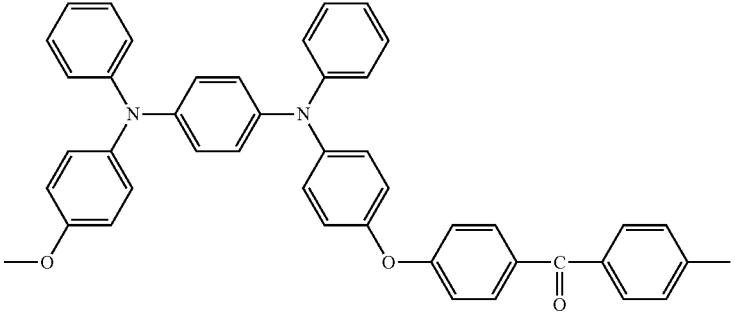 and 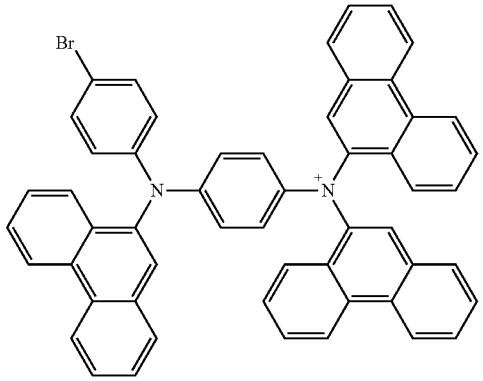 [SMILES: Brc1ccc(N(c2ccc(N(c3cc4ccccc4c4ccccc34)c3cc4ccccc4c4ccccc34)cc2)c2cc3ccccc3c3ccccc23)cc1] 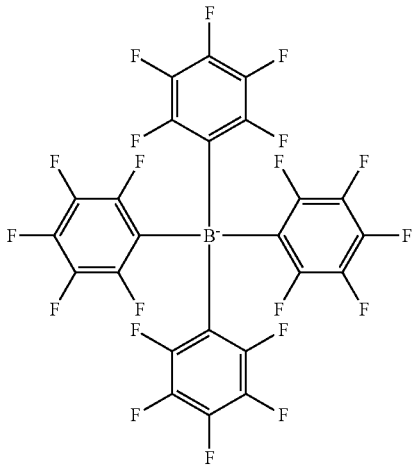 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 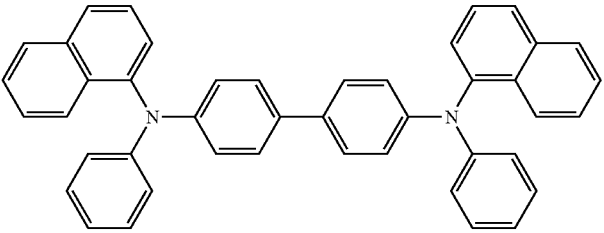 + $MoO_x$ | US20050123751 SID Symposium Digest, 37, 923 (2006) WO2009018009 |

TABLE 2-continued

| MATERIAL | EXAMPLES OF MATERIAL | PUBLICATIONS |
| --- | --- | --- |
| n-type semiconducting organic complexes | | US20020158242 |
| Metal organometallic complexes | | US20060240279 |
| Cross-linkable compounds | | US20080220265 |
| Polythiophene based polymers and copolymers | | WO 2011075644<br>EP2350216 |

TABLE 2-continued
| MATERIAL | EXAMPLES OF MATERIAL | PUBLICATIONS |
|---|---|---|
| Hole transporting materials | | |
| Triarylamines (e.g., TPD, α-NPD) | 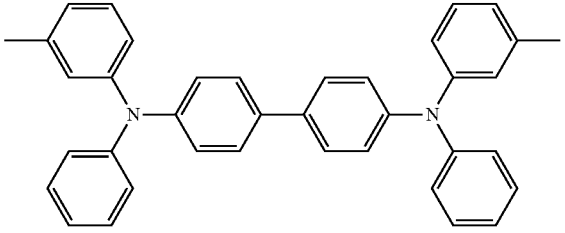 | Appl. Phys. Lett. 51, 913 (1987) |
| | 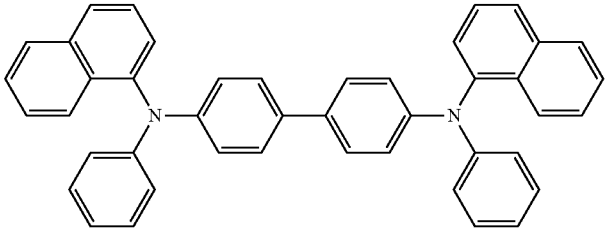 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 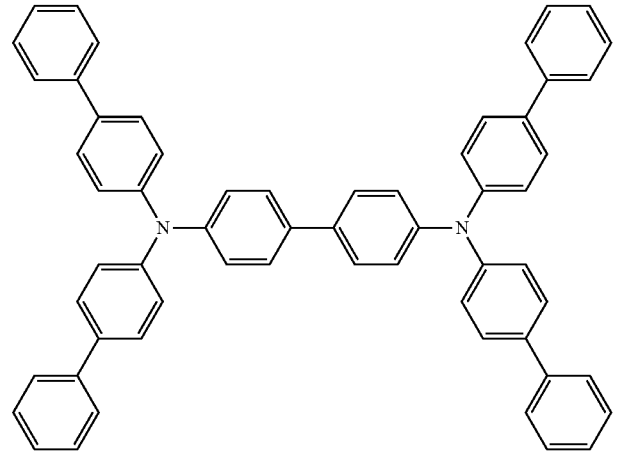 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 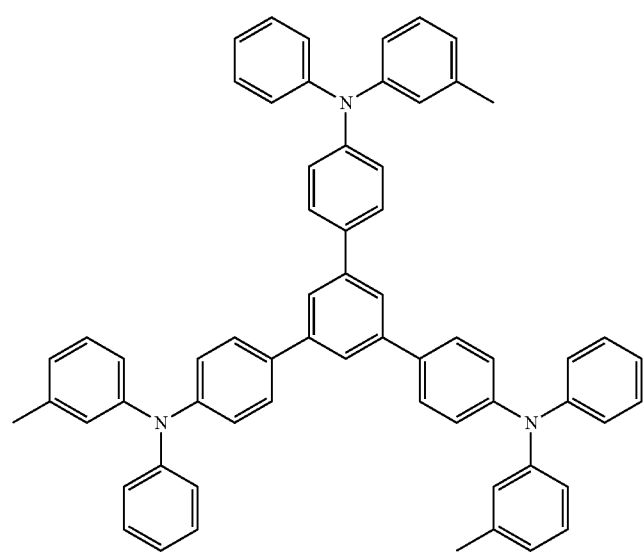 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 2-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |

| MATERIAL | EXAMPLES OF MATERIAL | PUBLICATIONS |
|---|---|---|
| Triarylamine with (di)benzothiophene/ (di)benzofuran | 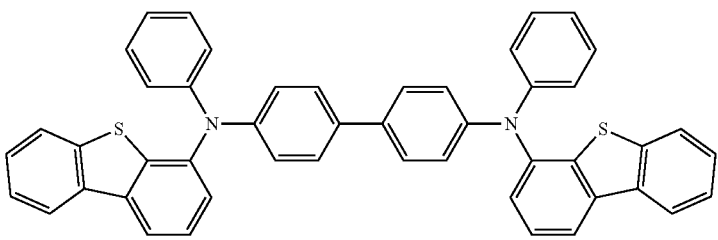 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 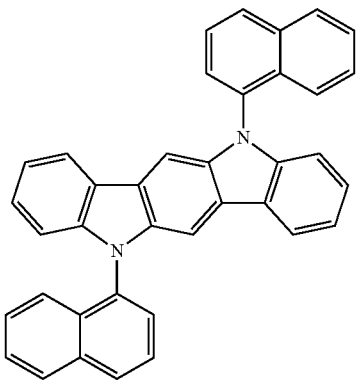 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 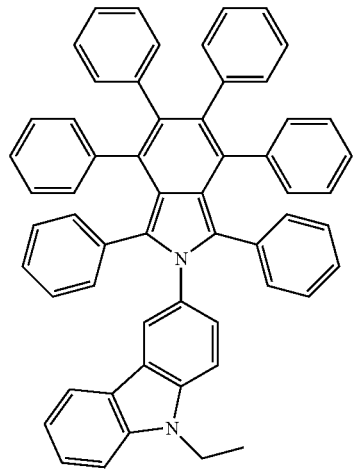 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 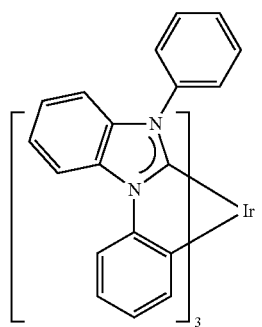 | US20080018221 |

TABLE 2-continued
| MATERIAL | EXAMPLES OF MATERIAL | PUBLICATIONS |
|---|---|---|
| Phosphorescent OLED hosts materials Red hosts | | |
| Arylcarbazoles | 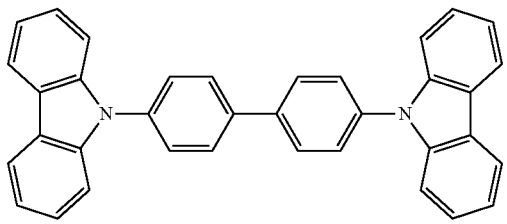 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq$_3$, BAlq) | 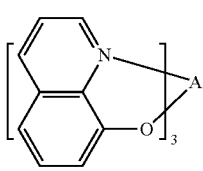 | Nature 395, 151 (1998) |
| | 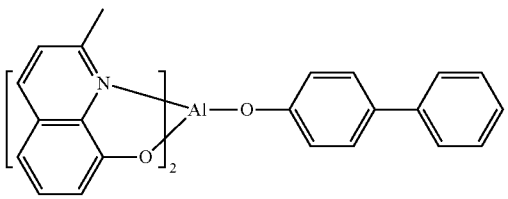 | US20060202194 |
| | 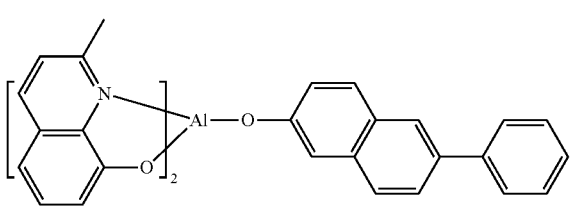 | WO2005014551 |
| | 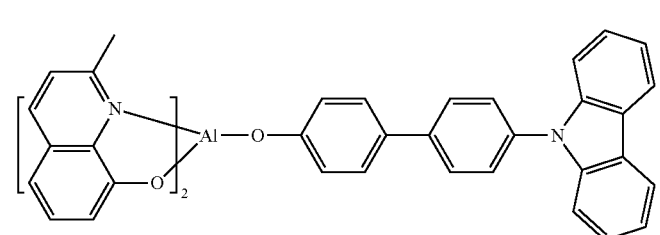 | WO2006072002 |
| Metal phenoxy-benzothiazole compounds | 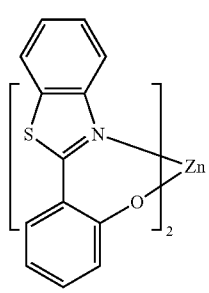 | Appl. Phys. Lett. 90, 123509 (2007) |
| Conjugated oligomers and polymers (e.g., polyfluorene) | 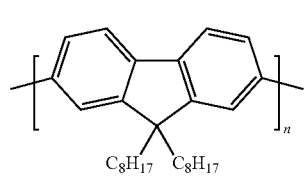 | Org. Electron. 1, 15 (2000) |

TABLE 2-continued
| MATERIAL | EXAMPLES OF MATERIAL | PUBLICATIONS |
|---|---|---|
| Aromatic fused rings | 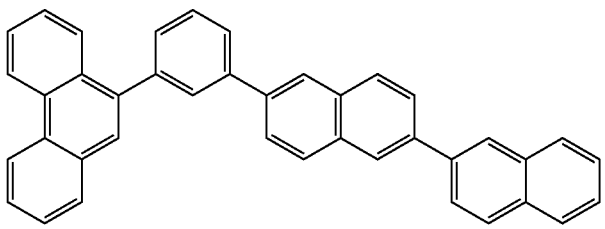 [SMILES: c1cc(-c2ccc3cc(-c4ccc5ccccc5c4)ccc3c2)cc(-c2cc3ccccc3c3ccccc23)c1] | WO2009066779, WO2009066778. WO2009063833, US20090045731, US20090045730. WO2009008311, US20090008605, US20090009065 |
| Zinc complexes | 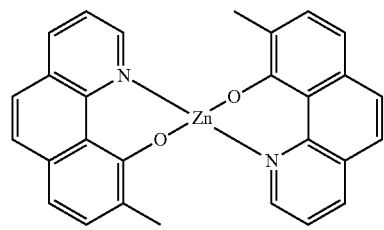 | WO2010056066 |
| Chrysene based compounds | 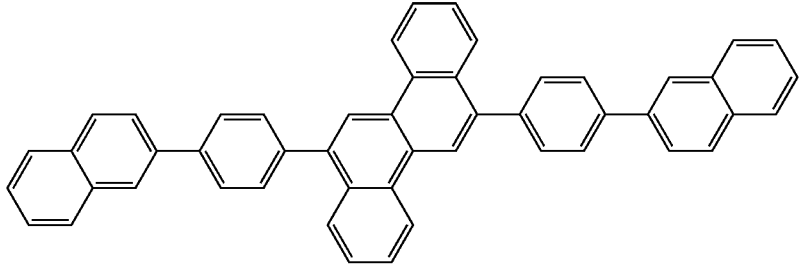 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
Green hosts
| Arylcarbazoles | 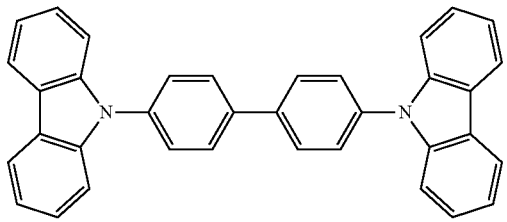 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
|---|---|---|
| | 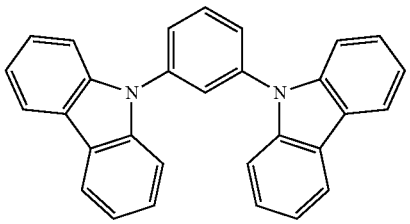 [SMILES: c1cc(-n2c3ccccc3c3ccccc32)cc(-n2c3ccccc3c3ccccc32)c1] | US20030175553 |
| | 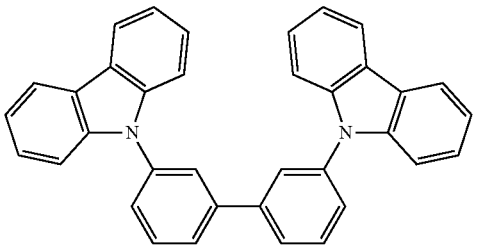 [SMILES: c1cc(-c2cccc(-n3c4ccccc4c4ccccc43)c2)cc(-n2c3ccccc3c3ccccc32)c1] | WO2001039234 |

TABLE 2-continued

| MATERIAL | EXAMPLES OF MATERIAL | PUBLICATIONS |
|---|---|---|
| Aryltriphenylene compounds | | US20060280965 |
| | | US20060280965 |
| | | WO2009021126 |
| Poly-fused heteroaryl compounds | | US20090309488<br>US20090302743<br>US20100012931 |
| Donor acceptor type molecules | | WO2008056746 |

TABLE 2-continued
| MATERIAL | EXAMPLES OF MATERIAL | PUBLICATIONS |
|---|---|---|
| | 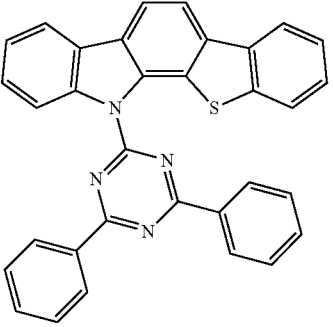 [SMILES: c1ccc(-c2nc(-c3ccccc3)nc(-n3c4ccccc4c4ccc5c6ccccc6sc5c43)n2)cc1] | WO2010107244 |
| Aza-carbazole/<br>DBT/DBF | 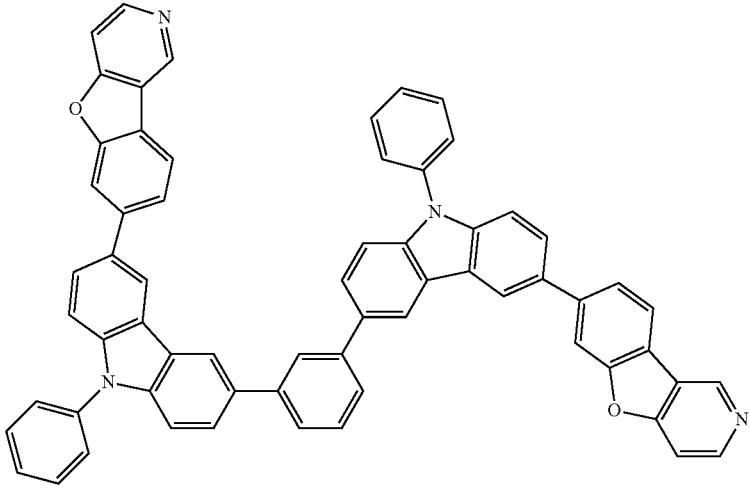 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 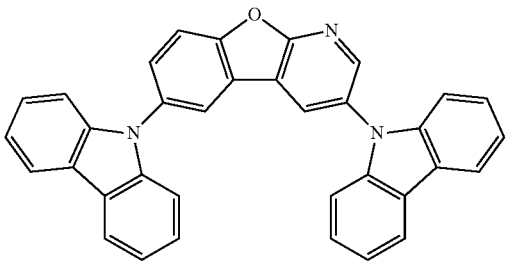 [SMILES: c1ccc2c(c1)c1ccccc1n2-c1ccc2oc3ncc(-n4c5ccccc5c5ccccc54)cc3c2c1] | US20100187984 |
| Polymers<br>(e.g., PVK) | 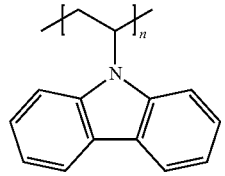 | Appl. Phys. Lett.<br>77, 2280 (2000) |
| Spirofluorene<br>compounds | 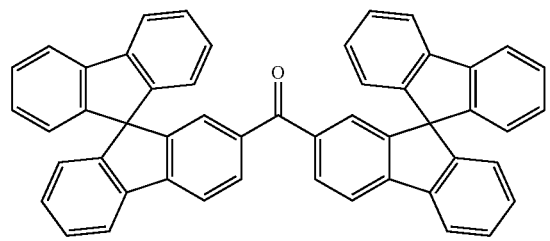 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 2-continued

| MATERIAL | EXAMPLES OF MATERIAL | PUBLICATIONS |
|---|---|---|
| Metal phenoxy-benzooxazole compounds | | WO2005089025 |
| | | WO2006132173 |
| | | JP200511610 |
| Spirofluorene-carbazole compounds | | JP2007254297 |
| | | JP2007254297 |

TABLE 2-continued

| MATERIAL | EXAMPLES OF MATERIAL | PUBLICATIONS |
| --- | --- | --- |
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 2-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |

Blue hosts

| | | |
| --- | --- | --- |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE 2-continued
| MATERIAL | EXAMPLES OF MATERIAL | PUBLICATIONS |
|---|---|---|
| | 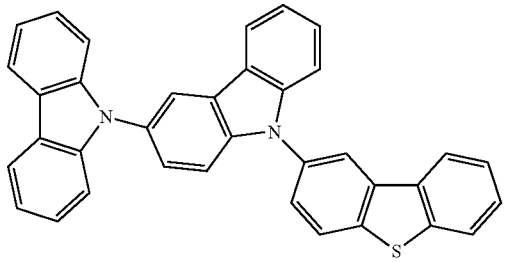 [SMILES: c1ccc2c(c1)sc1ccc(-n3c4ccccc4c4cc(-n5c6ccccc6c6ccccc65)ccc43)cc12] | WO2009086028 |
| | 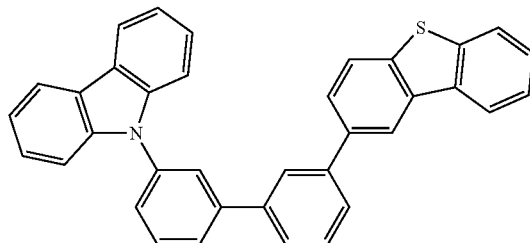 | US20090030202, US20090017330 |
| | 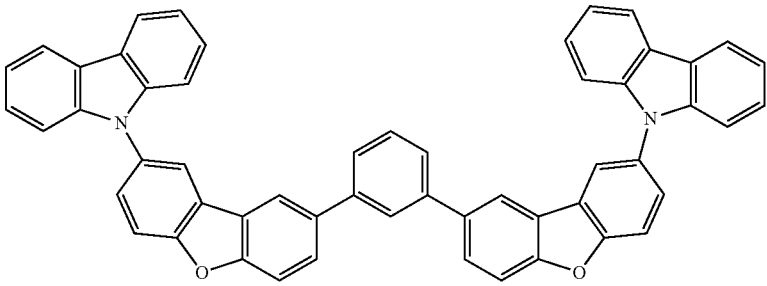 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 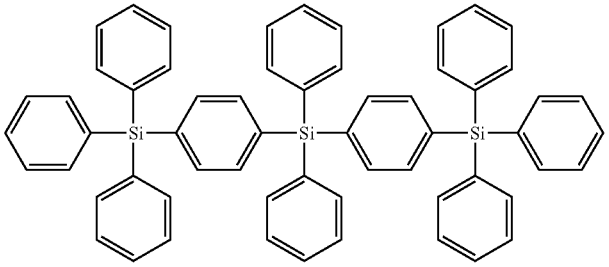 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 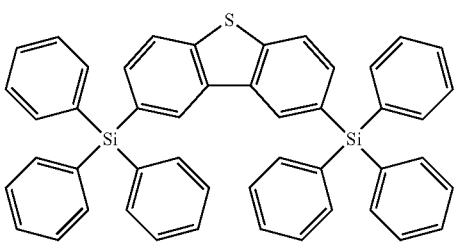 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 2-continued
| MATERIAL | EXAMPLES OF MATERIAL | PUBLICATIONS |
|---|---|---|
| Silicon/Germanium aryl compounds | 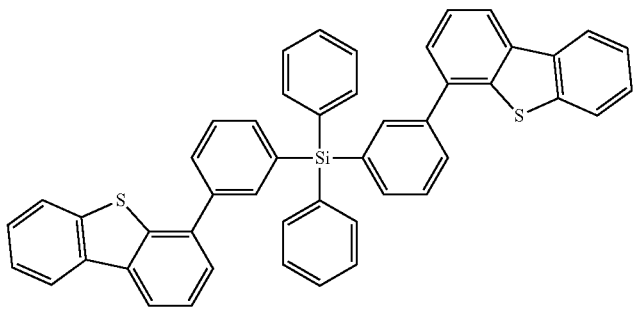 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 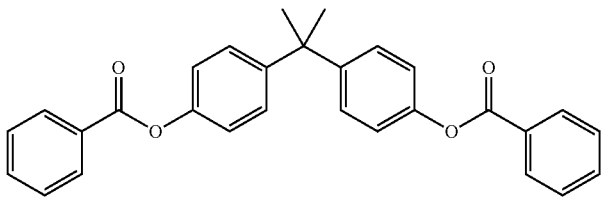 | WO2006100298 |
| Carbazole linked by non-conjugated groups | 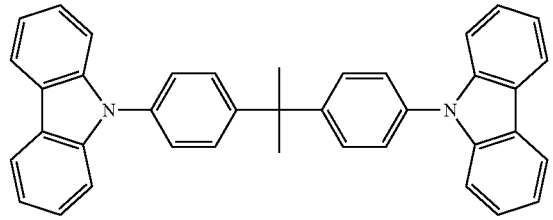 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 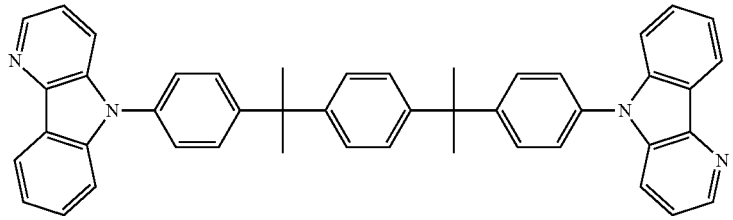 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 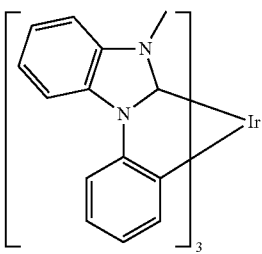 | U.S. Pat. No. 7,154,114 |

TABLE 2-continued

| MATERIAL | EXAMPLES OF MATERIAL | PUBLICATIONS |
| --- | --- | --- |
| *Phosphorescent dopants* | | |
| *Red dopants* | | |
| Heavy metal porphyrins (e.g., PtOEP) | [Pt octaethylporphyrin structure] | Nature 395, 151 (1998) |
| Iridium(III) organometallic complexes | [Ir(benzothienylpyridine)₂(acac) structure] | Appl. Phys. Lett. 78, 1622 (2001) |
| | [Ir(phenylisoquinoline)₂(acac) structure] | US2006835469 |
| | [Ir(methylphenylquinoline)₂(acac) structure] | US2006835469 |
| | [Ir(phenylquinoline)₂(acac) structure] | US20060202194 |

TABLE 2-continued

| MATERIAL | EXAMPLES OF MATERIAL | PUBLICATIONS |
|---|---|---|
| | | US20060202194 |
| | | US20070087321 |
| | | US20080261076<br>US20100090591 |
| | | US20070087321 |
| | | Adv. Mater. 19, 739 (2007) |

TABLE 2-continued

| MATERIAL | EXAMPLES OF MATERIAL | PUBLICATIONS |
|---|---|---|
| | | WO2009100991 |
| | | WO2008101842 |
| | | U.S. Pat. No. 7,232,618 |
| Platinum(II) organometallic complexes | | WO2003040257 |
| | | US20070103060 |

TABLE 2-continued

| MATERIAL | EXAMPLES OF MATERIAL | PUBLICATIONS |
| --- | --- | --- |
| Osmium(III) complexes | [structure: pyrazole with CF$_3$ group, pyridine, Os(PPhMe$_2$)$_2$] | Chem. Mater. 17, 3532 (2005) |
| Ruthenium(II) complexes | [structure: tBu-pyrazole, isoquinoline, Ru(PPhMe$_2$)$_2$] | Adv. Mater. 17, 1059 (2005) |
| Rhenium (I), (II), and (III) complexes | [structure: 8-hydroxyquinoline Re(CO)$_4$] | US20050244673 |

Green dopants

| | | |
| --- | --- | --- |
| Iridium(III) organometallic complexes | [structure: Ir(ppy)$_3$] and its derivatives | Inorg. Chem. 40, 1704 (2001) |
| | [structure: Ir(ppy)$_2$(acac)] | US20020034656 |

TABLE 2-continued
| MATERIAL | EXAMPLES OF MATERIAL | PUBLICATIONS |
|---|---|---|
| | 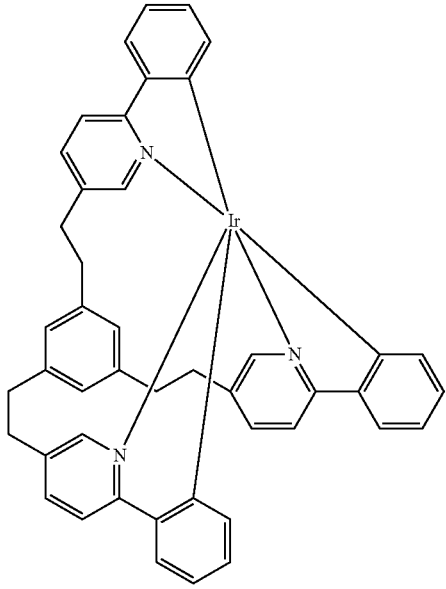 | U.S. Pat. No. 7,332,232 |
| | 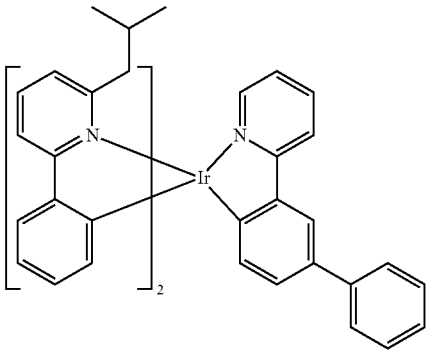 | US20090108737 |
| | 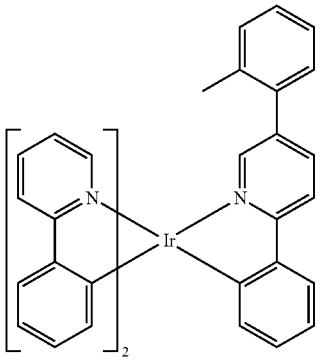 | WO2010028151 |

TABLE 2-continued

| MATERIAL | EXAMPLES OF MATERIAL | PUBLICATIONS |
|---|---|---|
| | | EP1841834B |
| | | US20060127696 |
| | | US20090039776 |
| | | U.S. Pat. No. 6,921,915 |
| | | US20100244004 |

TABLE 2-continued

| MATERIAL | EXAMPLES OF MATERIAL | PUBLICATIONS |
|---|---|---|
|  |  | U.S. Pat. No. 6,687,266 |
|  |  | Chem. Mater. 16, 2480 (2004) |
|  |  | US20076190359 |
|  |  | US 20060008670 JP2007123392 |
|  |  | WO2010086089, WO2011044988 |
|  |  | Adv. Mater. 16, 2003 (2004) |

TABLE 2-continued
| MATERIAL | EXAMPLES OF MATERIAL | PUBLICATIONS |
|---|---|---|
| | 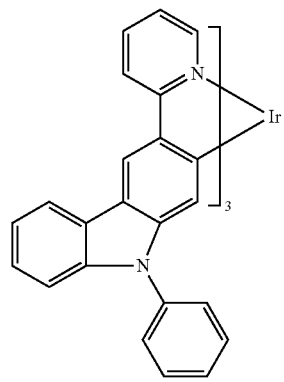 | Angew. Chem. Int. Ed. 2006, 45, 7800 |
| | 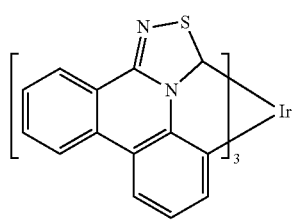 | WO2009050290 |
| | 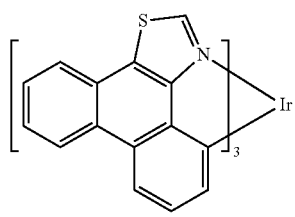 | US20090065846 |
| | 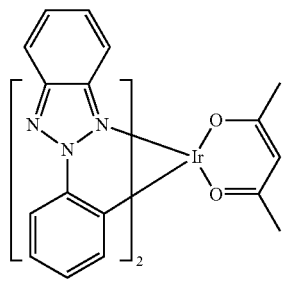 | US20080015355 |
| | 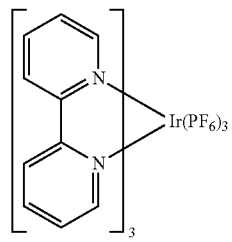 | US20010015432 |
| | 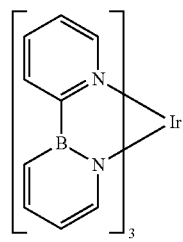 | US20100295032 |

TABLE 2-continued

| MATERIAL | EXAMPLES OF MATERIAL | PUBLICATIONS |
| --- | --- | --- |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 2-continued
| MATERIAL | EXAMPLES OF MATERIAL | PUBLICATIONS |
|---|---|---|
| | 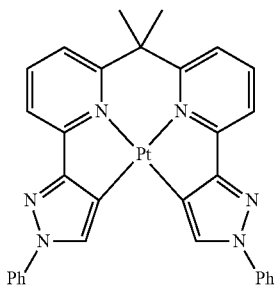 | US20060263635 |
| | 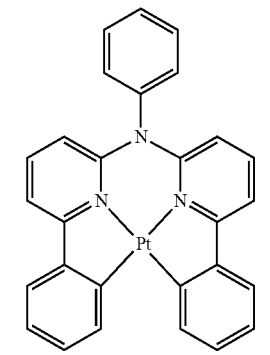 | US20060182992<br>US20070103060 |
| Cu complexes | 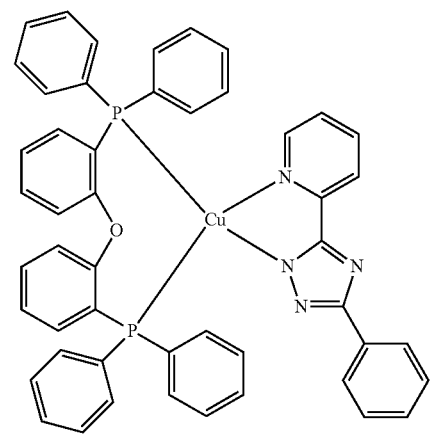 | WO2009000673 |
| | 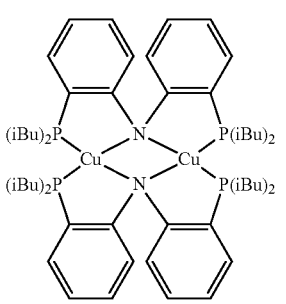 | US20070111026 |

TABLE 2-continued

| MATERIAL | EXAMPLES OF MATERIAL | PUBLICATIONS |
| --- | --- | --- |
| Gold complexes | | Chem. Commun. 2906 (2005) |
| Rhenium(III) complexes | | Inorg. Chem. 42, 1248 (2003) |
| Osmium(II) complexes | | U.S. Pat. No. 7,279,704 |
| Deuterated organometallic complexes | | US20030138657 |

| MATERIAL | EXAMPLES OF MATERIAL | PUBLICATIONS |
|---|---|---|
| Organometallic complexes with two or more metal centers | 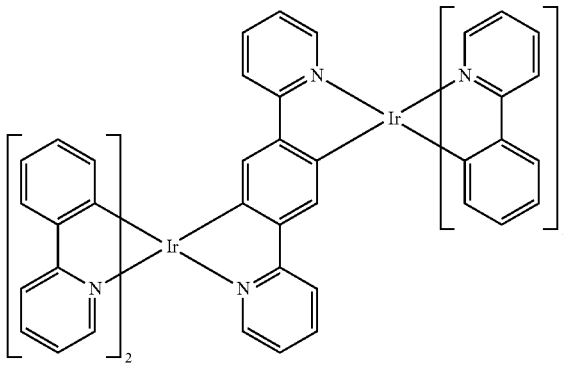 | US20030152802 |
| | 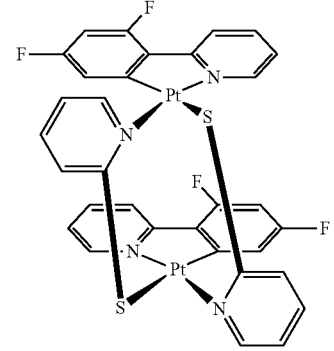 | U.S. Pat. No. 7,090,928 |
| Blue dopants | | |
| Iridium(III) organometallic complexes | 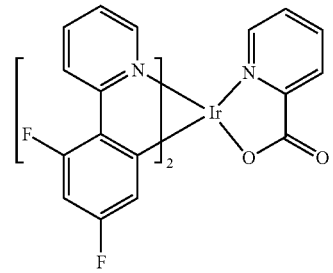 | WO2002002714 |
| | 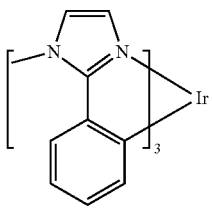 | WO2006009024 |
| | 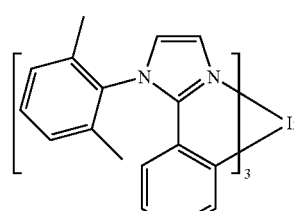 | US20060251923<br>US20110057559<br>US20110204333 |

TABLE 2-continued
| MATERIAL | EXAMPLES OF MATERIAL | PUBLICATIONS |
|---|---|---|
| | 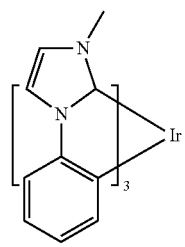 | U.S. Pat. No. 7,393,599, WO2006056418, US20050260441, WO2005019373 |
| | 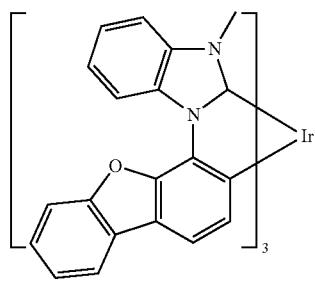 | U.S. Pat. No. 7,534,505 |
| | 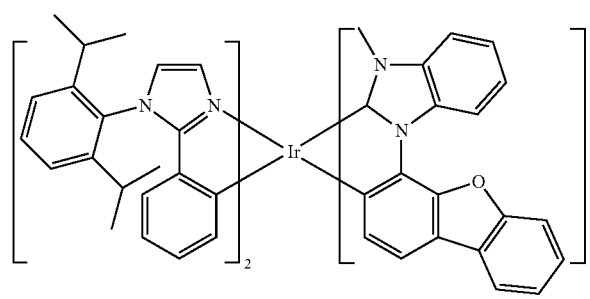 | WO2011051404 |
| | 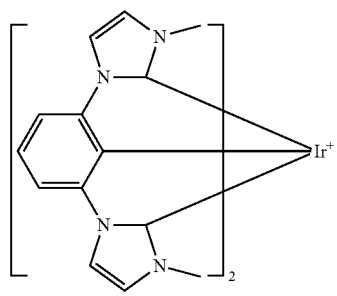 | U.S. Pat. No. 7,445,855 |
| | 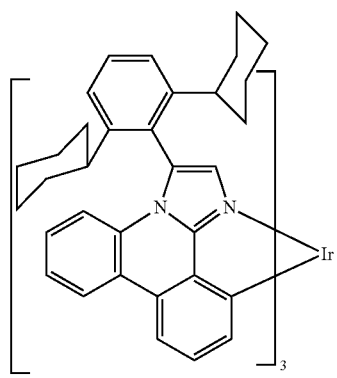 | US20070190359, US20080297033 US20100148663 |

TABLE 2-continued
| MATERIAL | EXAMPLES OF MATERIAL | PUBLICATIONS |
|---|---|---|
| | 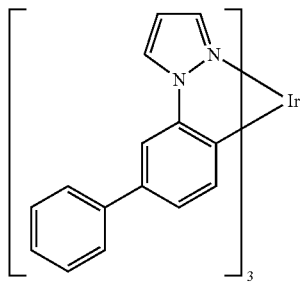 | U.S. Pat. No. 7,338,722 |
| | 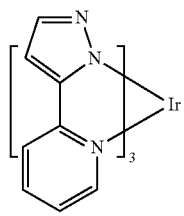 | US20020134984 |
| | 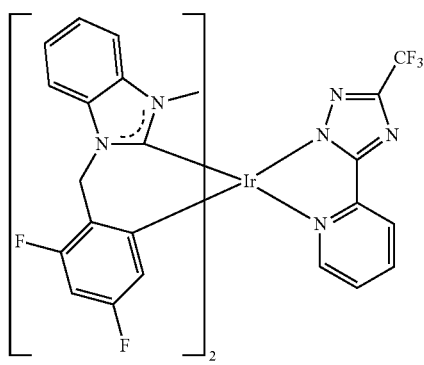 | Angew. Chem. Int. Ed. 47, 4542 (2008) |
| | 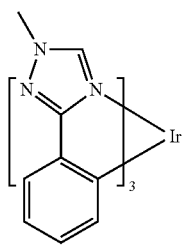 | Chem. Mater. 18, 5119 (2006) |
| | 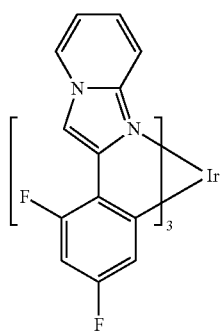 | Inorg. Chem. 46, 4308 (2007) |

TABLE 2-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium(II) complexes | | U.S. Pat. No. 7,279,704 |

TABLE 2-continued

| MATERIAL | EXAMPLES OF MATERIAL | PUBLICATIONS |
| --- | --- | --- |
| | | Organometallics 23, 3745 (2004) |
| Gold complexes | | Appl. Phys. Lett. 74, 1361 (1999) |
| Platinum(II) complexes | | WO2006098120, WO2006103874 |
| Pt tetradentate complexes with at least one metal-carbene bond | | U.S. Pat. No. 7,655,323 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |

TABLE 2-continued

| MATERIAL | EXAMPLES OF MATERIAL | PUBLICATIONS |
| --- | --- | --- |
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE 2-continued

| MATERIAL | EXAMPLES OF MATERIAL | PUBLICATIONS |
|---|---|---|
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |
| Electron transporting materials | | |
| Anthracene-benzoimidazole compounds | | WO2003060956 |
| | | US20090179554 |

TABLE 2-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 2-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 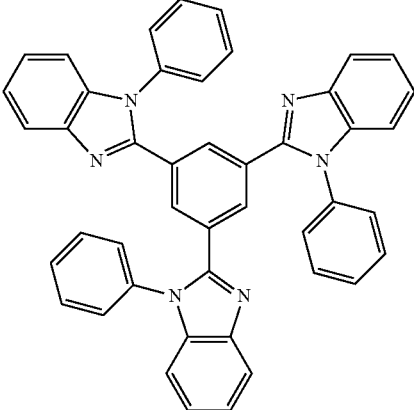 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
|  | 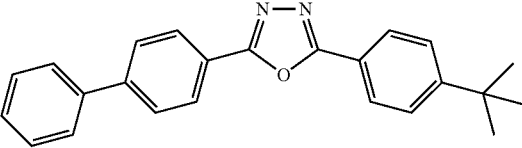 [SMILES: CC(C)(C)c1ccc(-c2nnc(-c3ccc(-c4ccccc4)cc3)o2)cc1] | Appl. Phys. Lett. 55, 1489 (1989) |
|  | 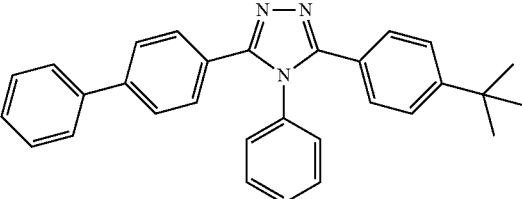 | Jpn. J. Apply. Phys. 32, L917 (1993) |
| Silole compounds | 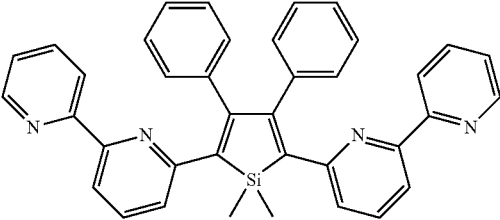 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 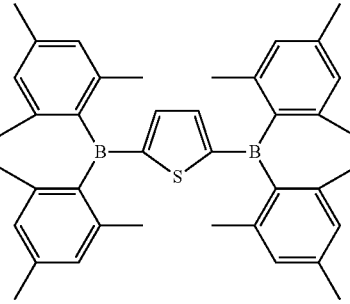 | J. Am. Chem. Soc. 120, 9714 (1998) |
| Fluorinated aromatic compounds | 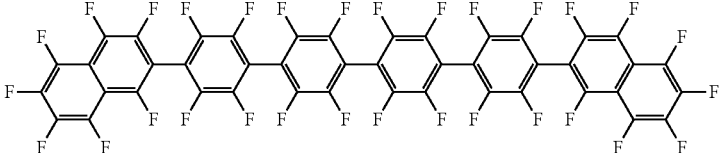 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE 2-continued

| MATERIAL | EXAMPLES OF MATERIAL | PUBLICATIONS |
|---|---|---|
| Fullerene (e.g. C60) | 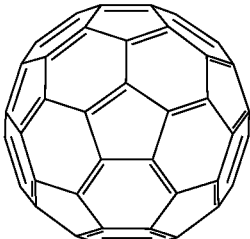 | US20090101870 |
| Triazine complexes | 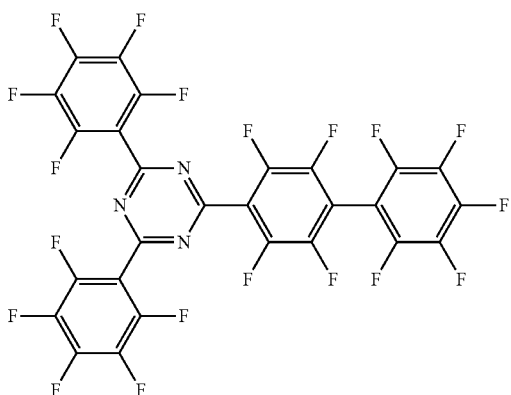 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 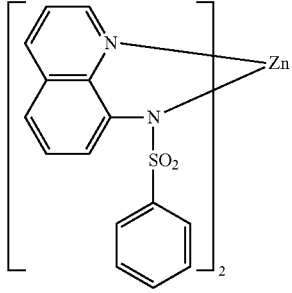 | U.S. Pat. No. 6,528,187 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having a formula:
$G^1$—L—$G^2$, Formula I;
wherein $G^1$ has the structure:

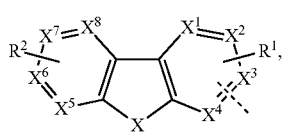

and
$G^2$ has the structure:

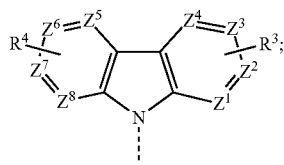

wherein L is selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein X is selected from the group consisting of O, S, and Se;

wherein each of $X^1$, $X^2$, $X^3$, $X^4$, $X^5$, $X^6$, $X^7$, $X^8$, $Z^1$, $Z^2$, $Z^3$, $Z^4$, $Z^5$, $Z^6$, $Z^7$, and $Z^8$ is carbon or nitrogen;

wherein at least two of $X^1$, $X^2$, $X^3$, $X^4$, $X^5$, $X^6$, $X^7$, and $X^8$ are nitrogen;

wherein at least one of $X^1$, $X^2$, $X^3$, and $X^4$ is carbon and bonded to L;

wherein the dashed lines represent the bonds between $G^1$ and L and $G^2$ and L;

wherein each $R^2$, $R^3$, and $R^4$ represent mono, di, tri, tetra substitutions or no substitution;

wherein $R^1$ represents mono, di, tri substitutions or no substitution;

wherein $R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein the substitution is optionally fused to $G^1$ or $G^2$; and wherein when $R^3$ or $R^4$ is carbazole or substituted carbazole, the carbazole or substituted carbazole is connected to $G^2$ by N.

2. The compound of claim 1, wherein when $R^1$ or $R^2$ is carbazole or substituted carbazole, the carbazole or substituted carbazole is connected to $G^1$ by N.

3. The compound of claim 1, wherein X is O or S.

4. The compound of claim 1, wherein only two of $X^1$, $X^2$, $X^3$, $X^4$, $X^5$, $X^6$, $X^7$, and $X^8$ are nitrogen.

5. The compound of claim 1, wherein only two of $X^1$, $X^2$, $X^3$, $X^4$, $X^5$, $X^6$, $X^7$, and $X^8$ are nitrogen and on the same ring.

6. The compound of claim 1, wherein only two of $X^1$, $X^2$, $X^3$, $X^4$, $X^5$, $X^6$, $X^7$, and $X^8$ are nitrogen and on the same ring that is bonded to L.

7. The compound of claim 1, wherein each $Z^1$, $Z^2$, $Z^3$, $Z^4$, $Z^5$, $Z^6$, $Z^7$, and $Z^8$ is carbon.

8. The compound of claim 1, wherein $R^1$, and $R^2$ are each independently selected from the group consisting of hydrogen, deuterium, halide, alkyl, phenyl, pyridyl, carbazolyl, and combinations thereof.

9. The compound of claim 1, wherein $R^3$, and $R^4$ are each independently selected from the group consisting of hydrogen, deuterium, phenyl, pyridyl, 9-carbazolyl, and combinations thereof.

10. The compound of claim 1, wherein $G^1$ is selected from the group consisting of:

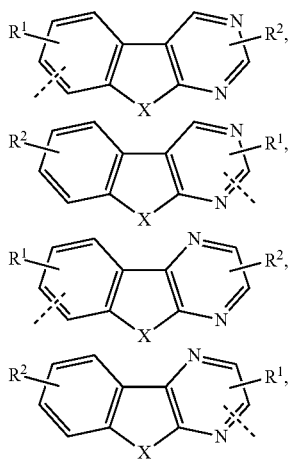

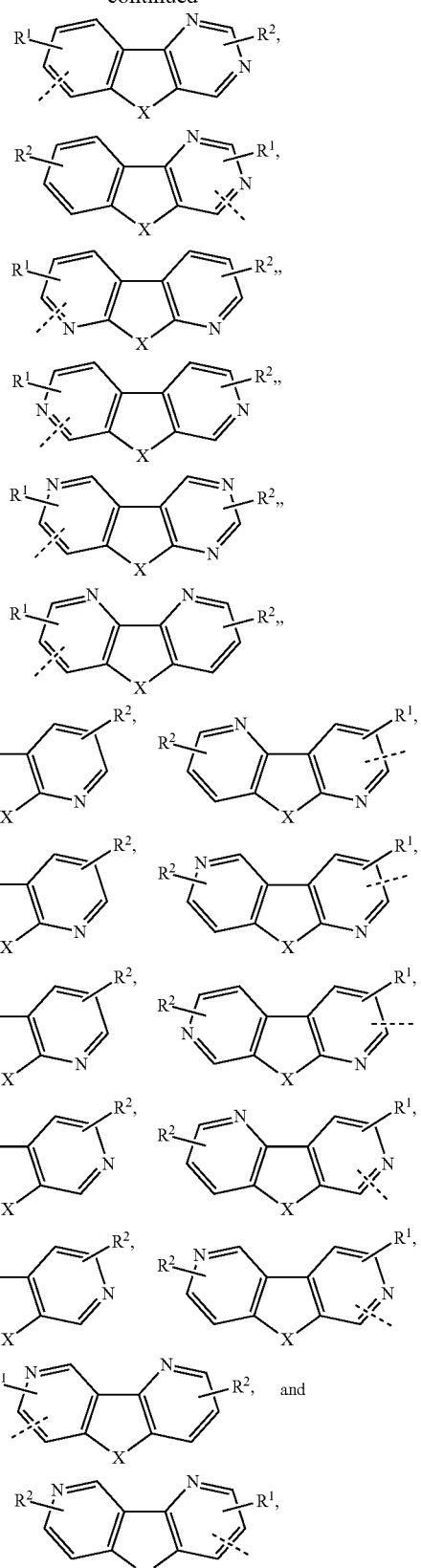

wherein X is selected from the group consisting of O, S, and Se.

11. The compound of claim 1, wherein L is selected from the group consisting of:
a direct bond,
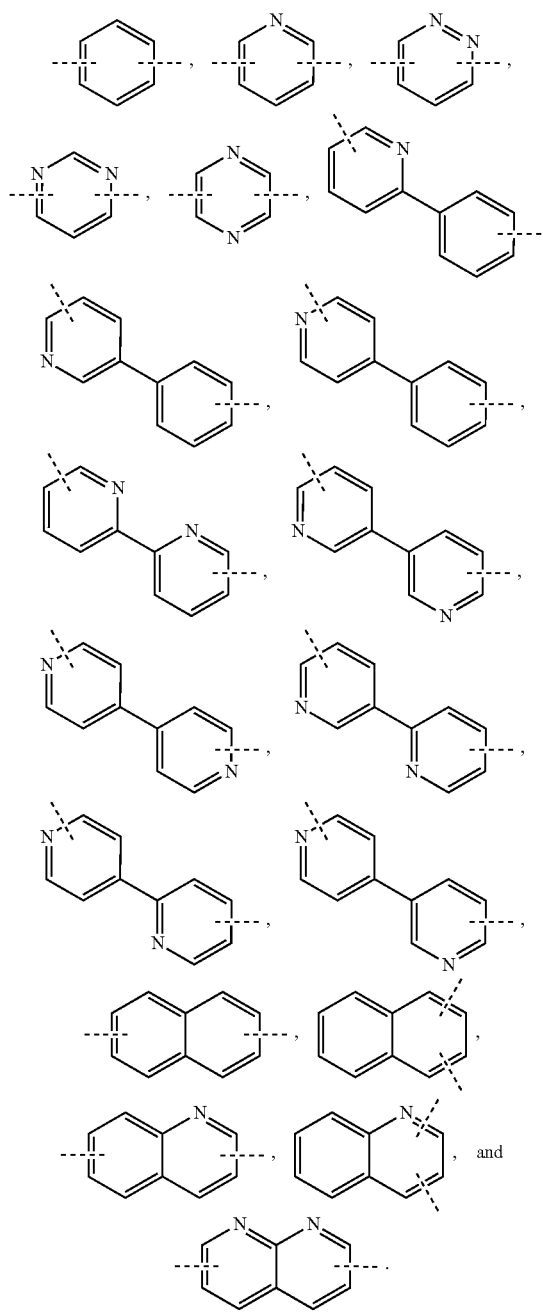
and
12. The compound of claim 1, wherein $G^1$ is selected from the group consisting of:
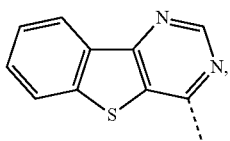
D1
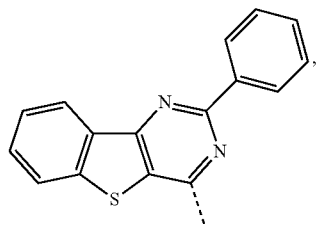
D2
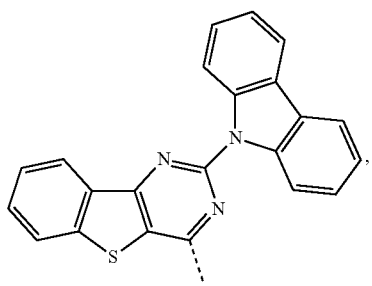
D3
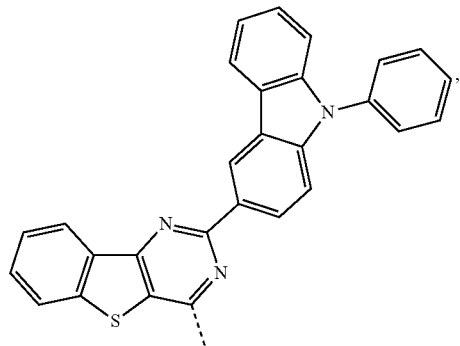
D4
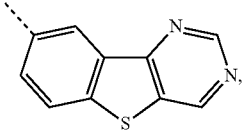
D5
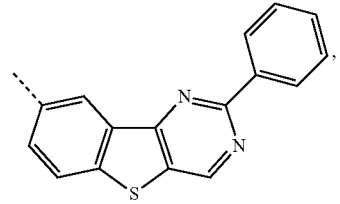
D6
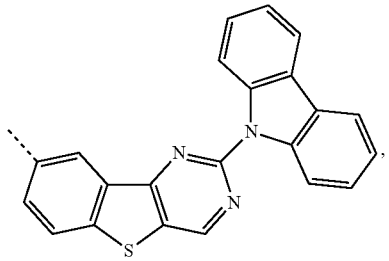
D7

D8
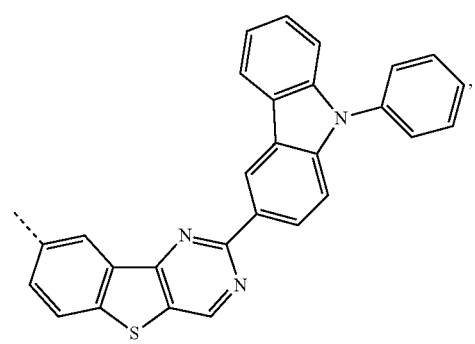
D9
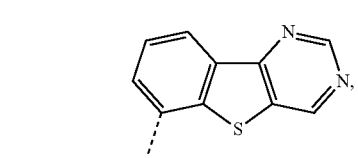
D10
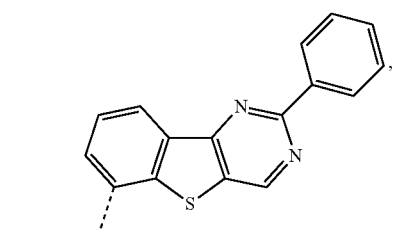
D11
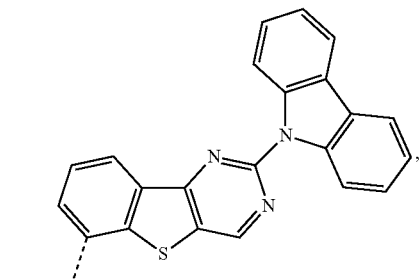
D12
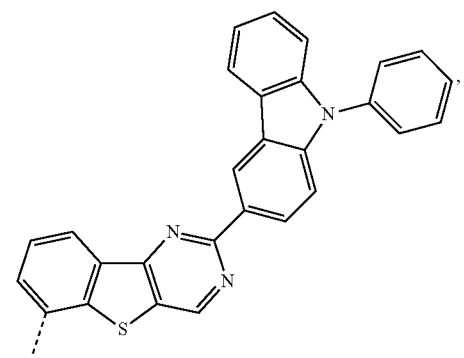
D13
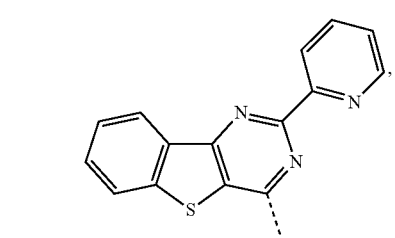
D14
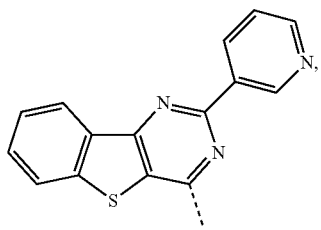
D15
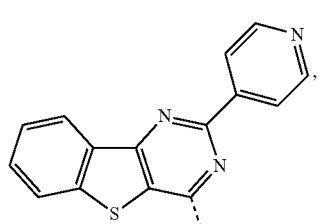
D16
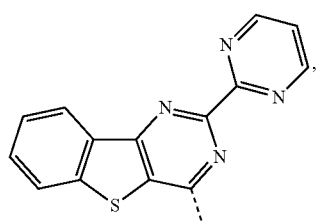
D17
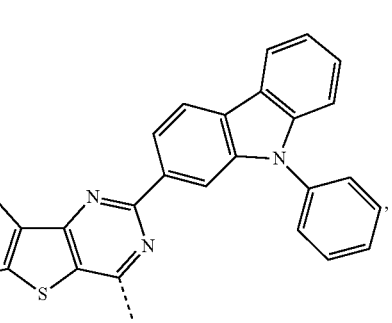
D18
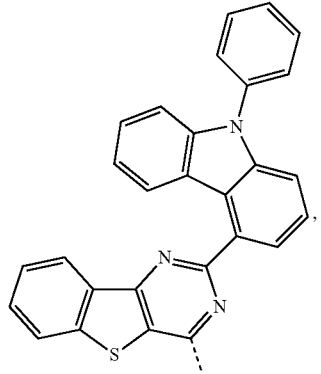
D19
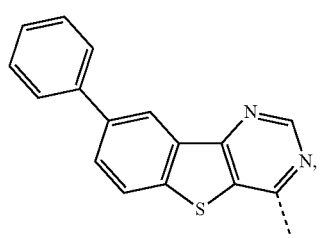

-continued
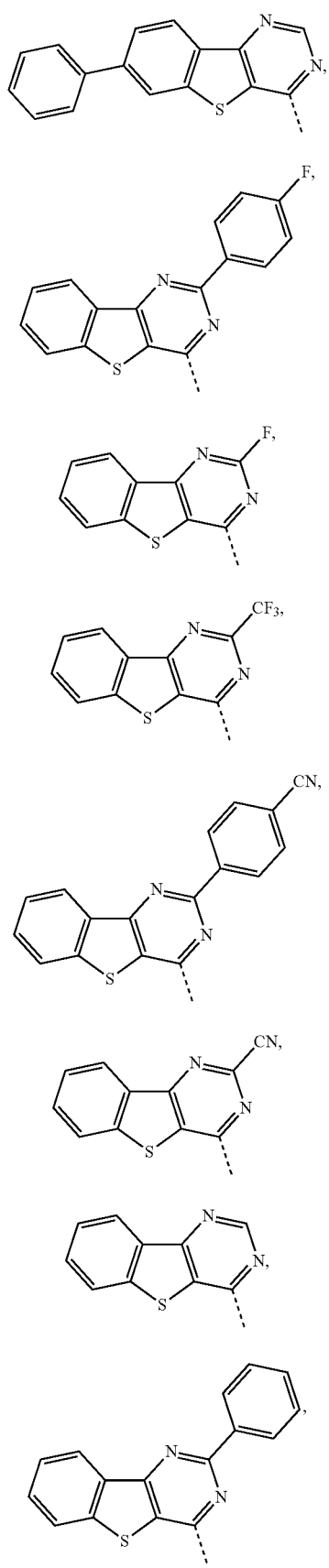
D20
D21
D22
D23
D24
D25
D26
D27
-continued
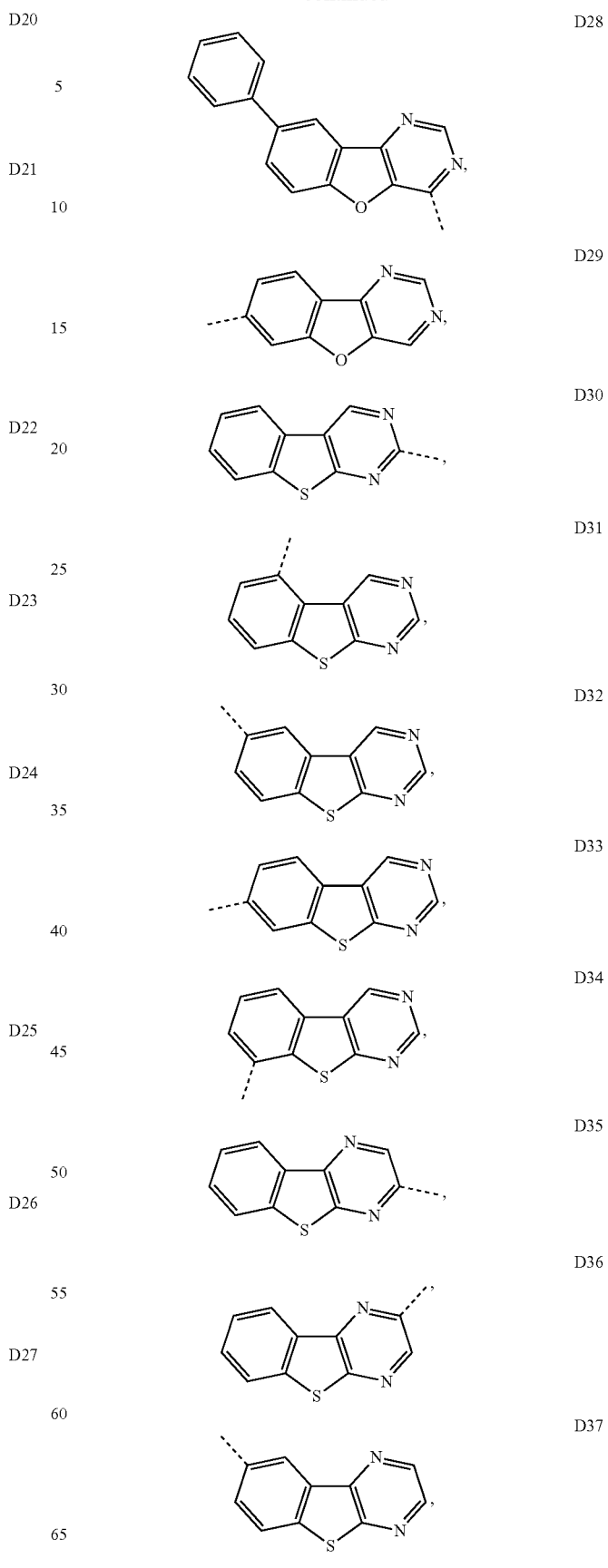
D28
D29
D30
D31
D32
D33
D34
D35
D36
D37

-continued
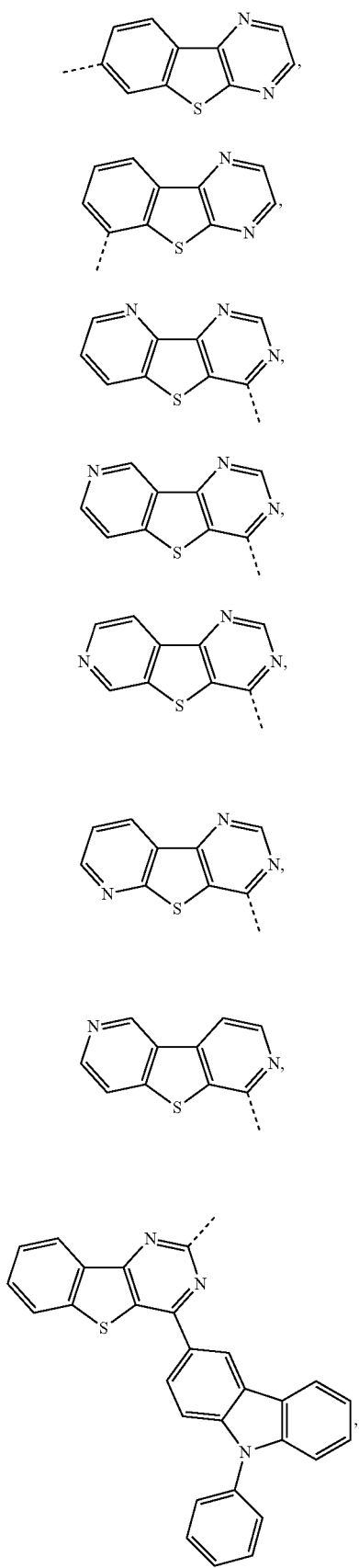
D38
D39
D40
D41
D42
D43
D44
D45
-continued
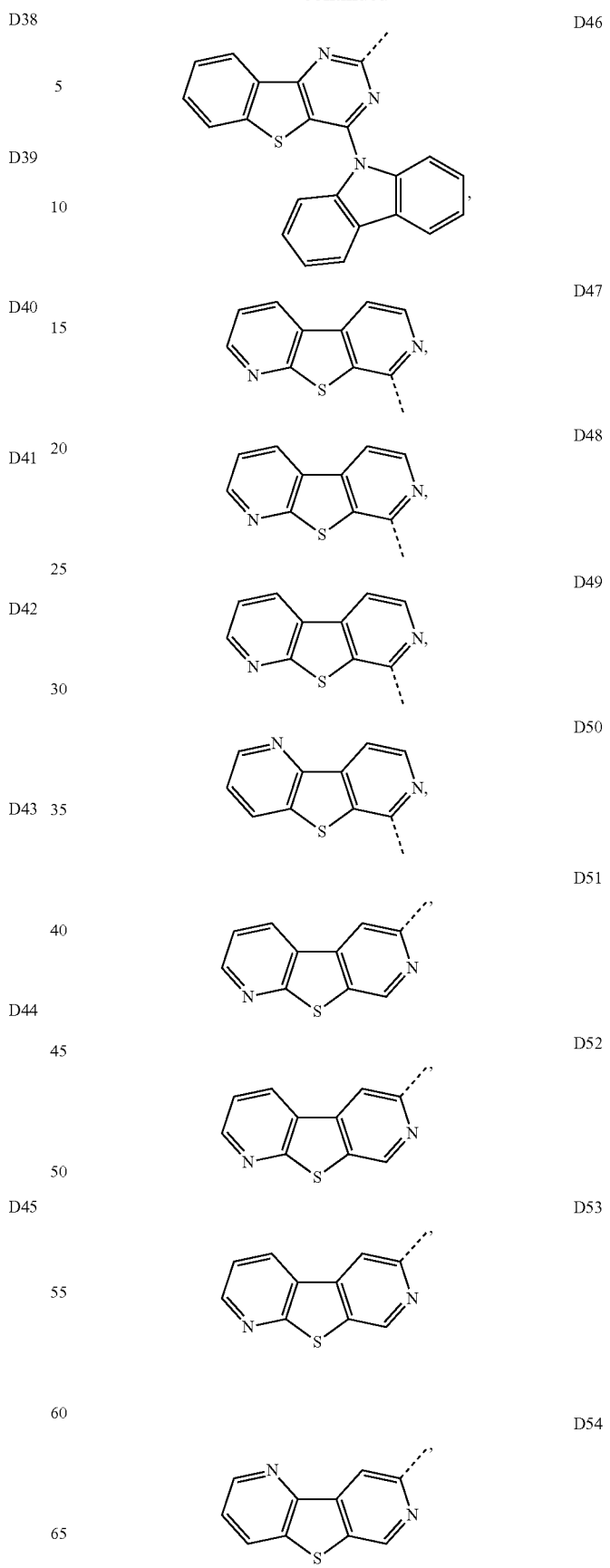
D46
D47
D48
D49
D50
D51
D52
D53
D54

-continued
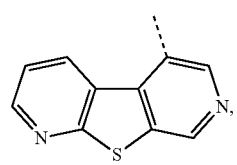 D55
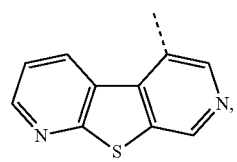 D56
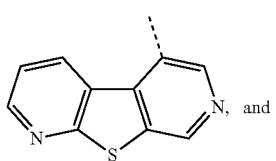 D57, and
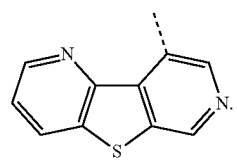 D58
13. The compound of claim 1, wherein L is selected from the group consisting of:
a direct bond (L1),
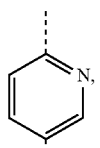 L2
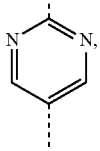 L3
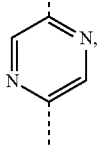 L4
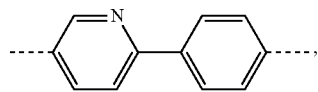 L5
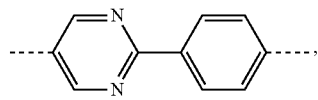 L6
-continued
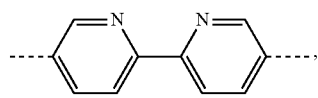 L7
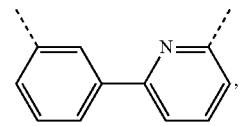 L8
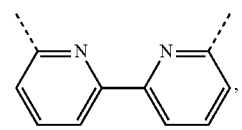 L9
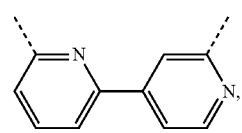 L10
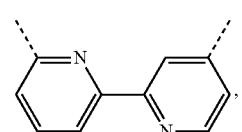 L11
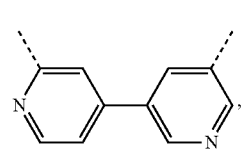 L12
L13
L14
L15
L16
L17

14. The compound of claim 1, wherein $G^2$ is selected from the group consisting of:

-continued
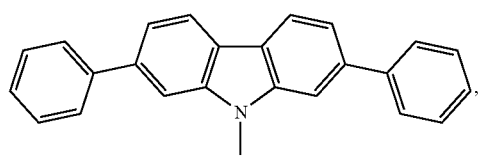
C6
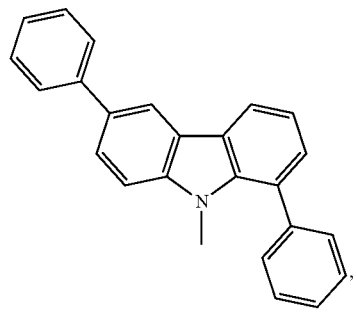
C7
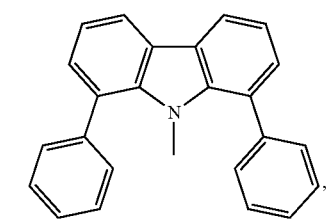
C8
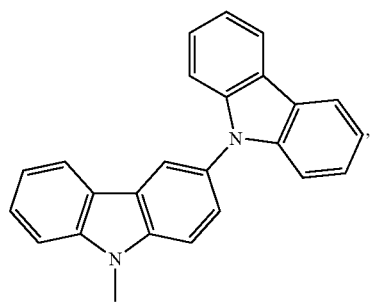
C9
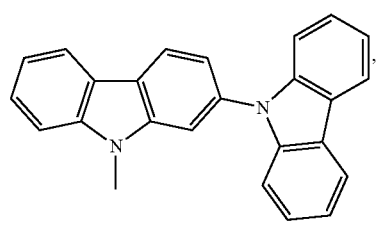
C10
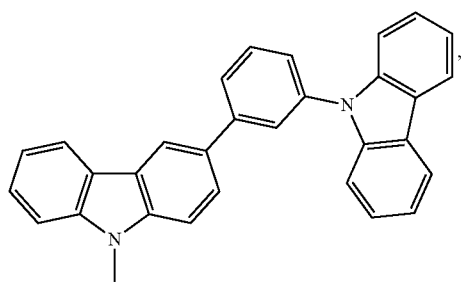
C11
-continued
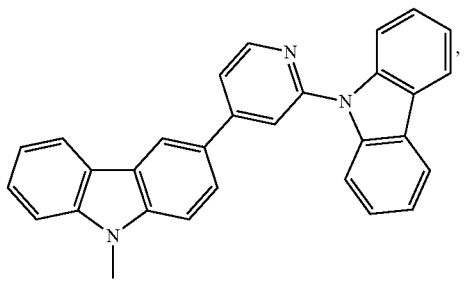
C12
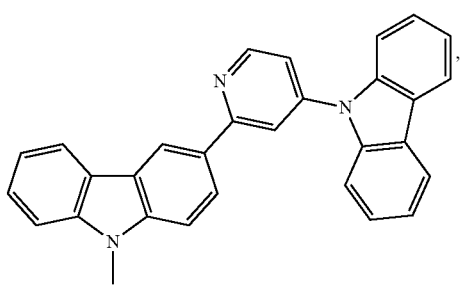
C13
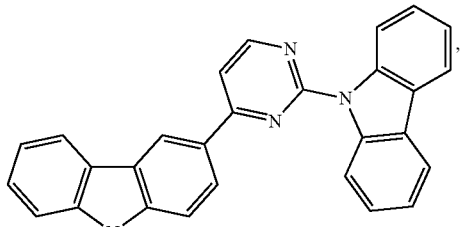
C14
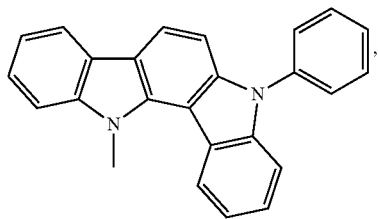
C15
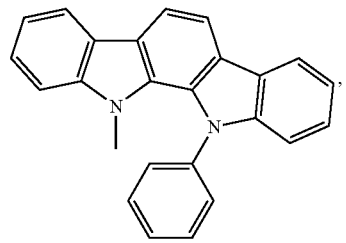
C16
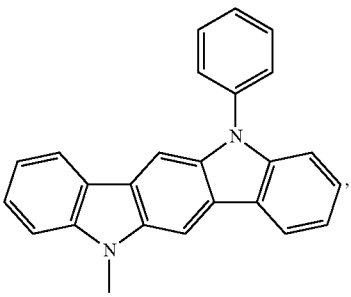
C17

-continued
C18
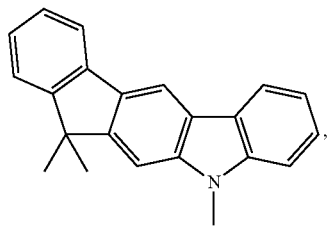
C19
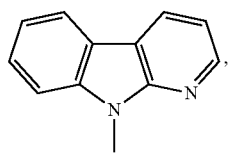
C20
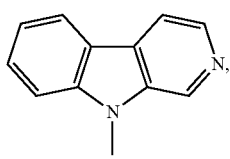
C21
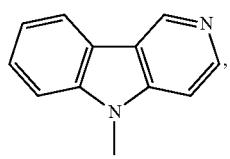
C22
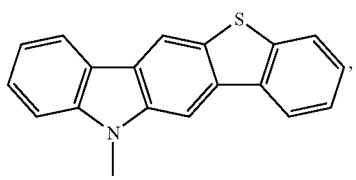
C23
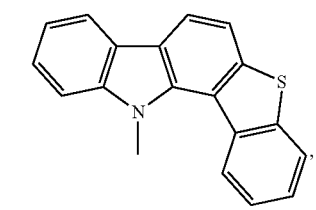
C24
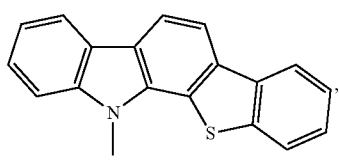
C25
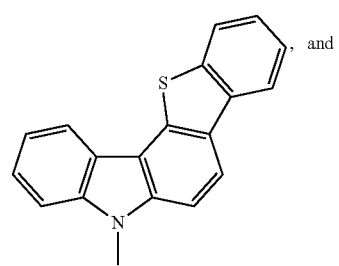
, and
-continued
C26
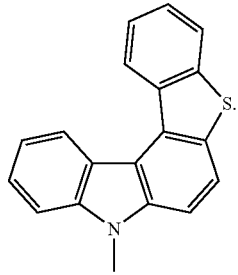
15. The compound of claim 1, wherein the compound is Compound x having the formula Di-Lj-Ck;
wherein x=1740k+58j+i−1798, i is an integer from 1 to 58, j is an integer from 1 to 30, and k is an integer from 1 to 26; and
wherein D1 to D58 have the following structures:
D1
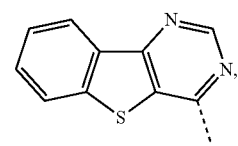
D2
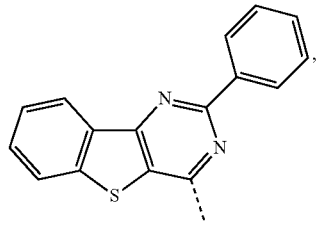
D3
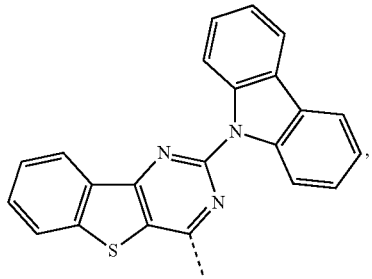
D4
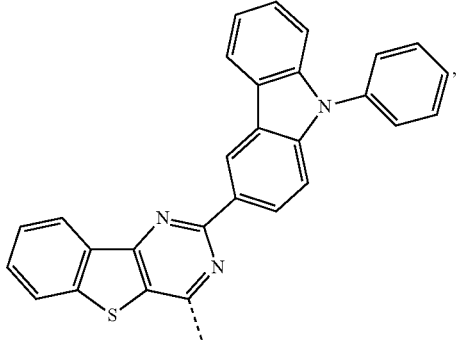

161
-continued
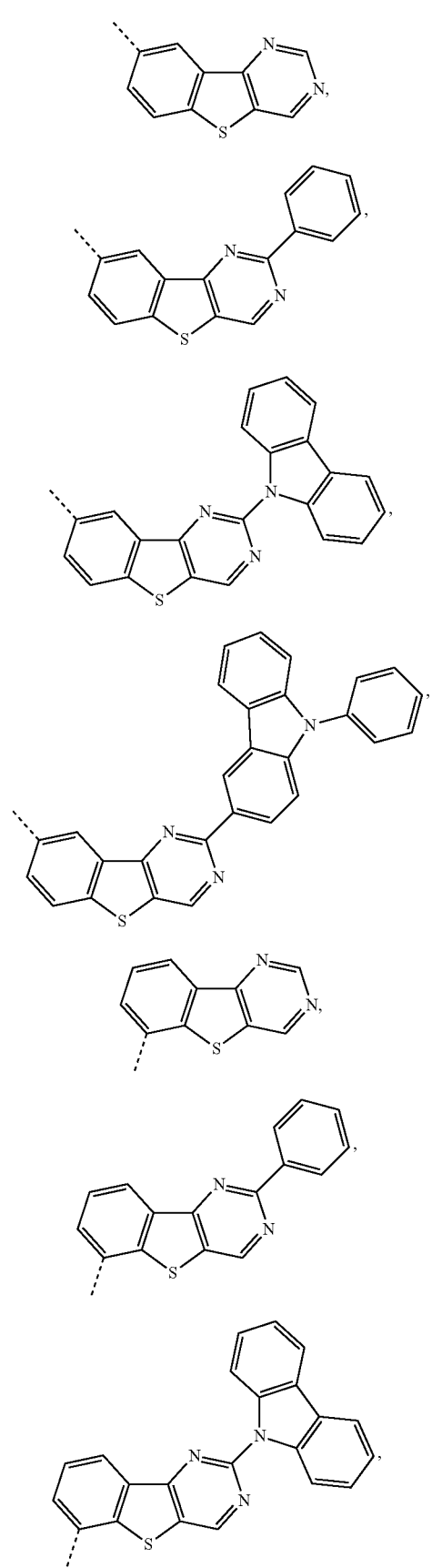
162
-continued
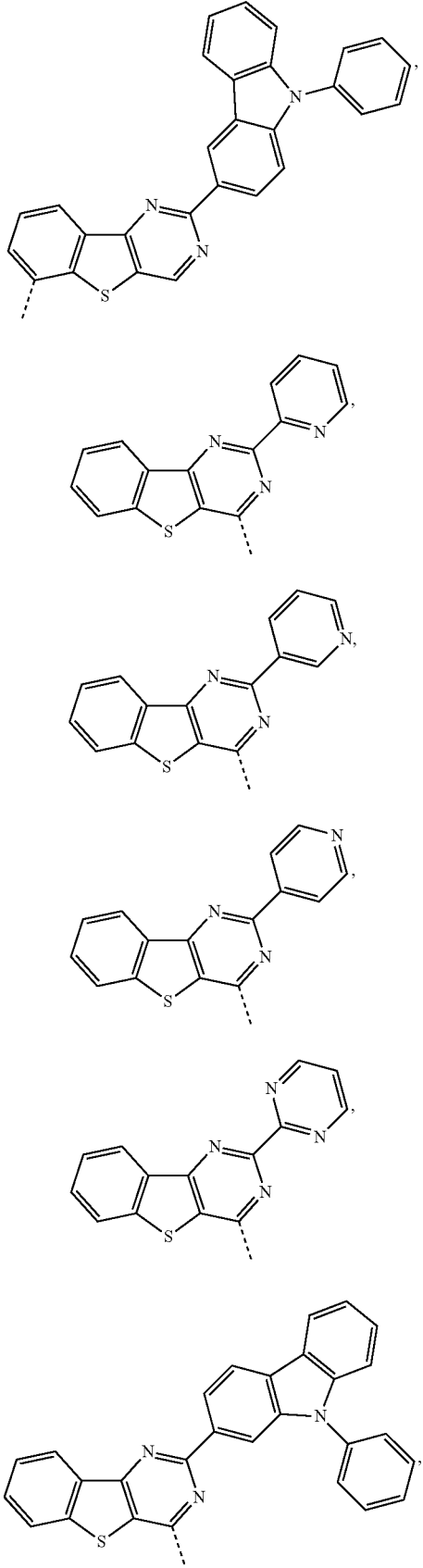

-continued
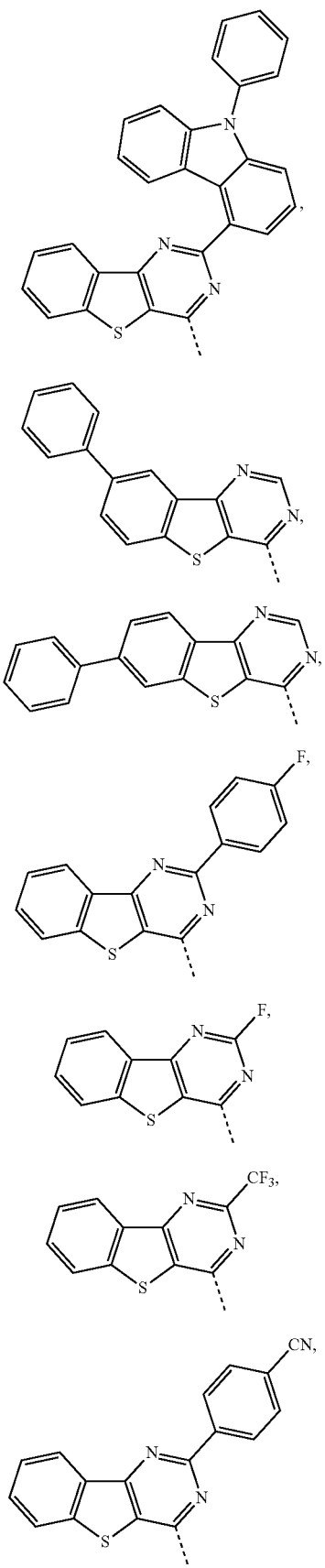
D18
D19
D20
D21
D22
D23
D24
-continued
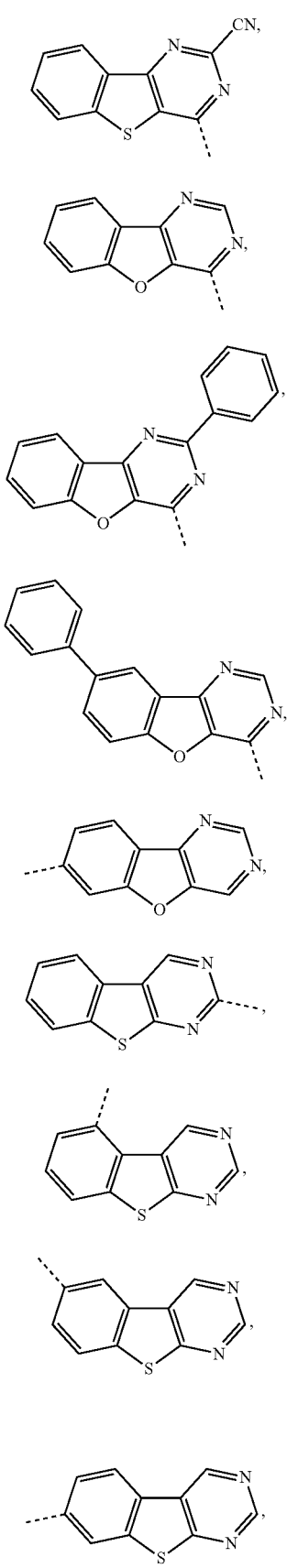
D25
D26
D27
D28
D29
D30
D31
D32
D33

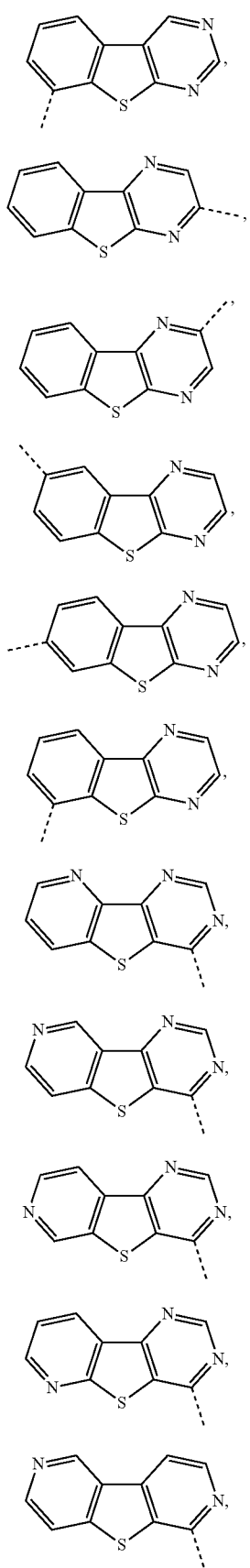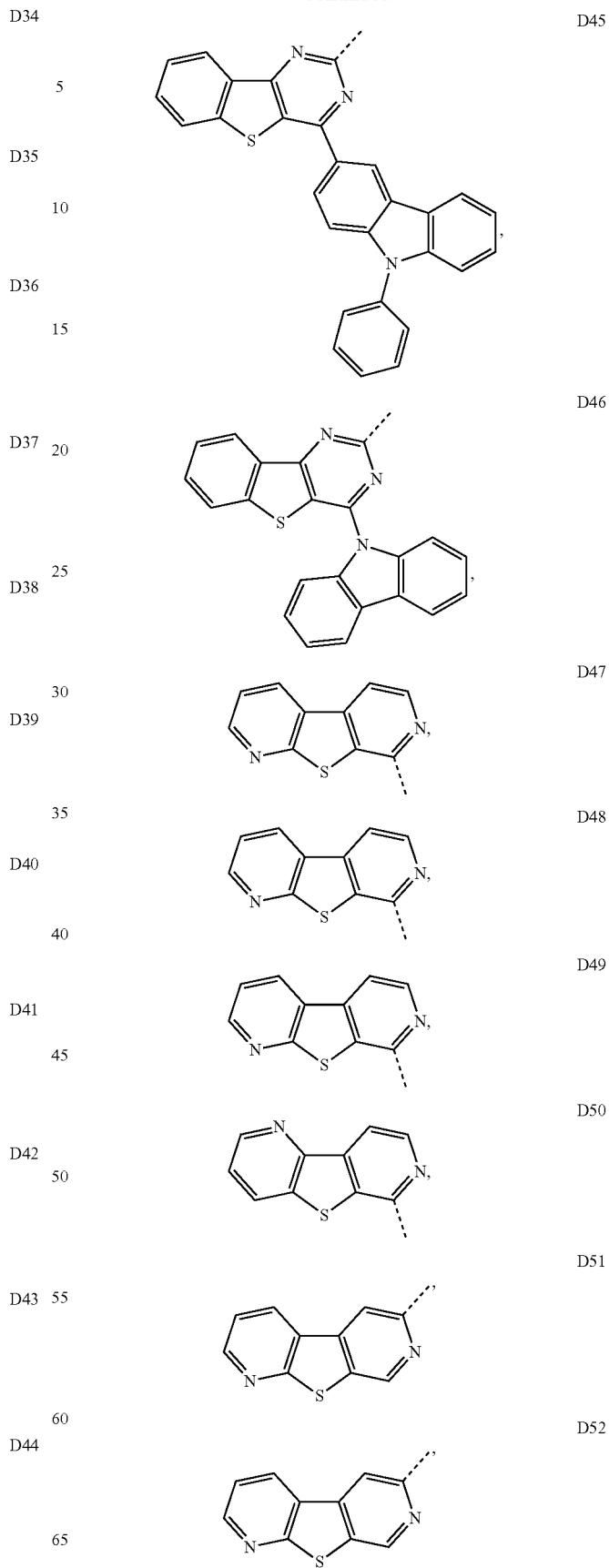

wherein L1 to L30 have the following structures:
L1 is a direct bond,

-continued
L16
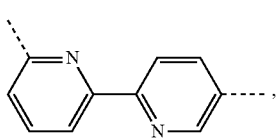
L17
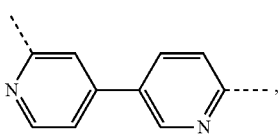
L18
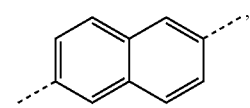
L19
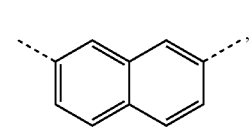
L20
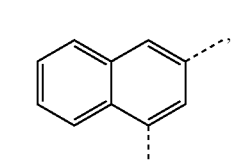
L21
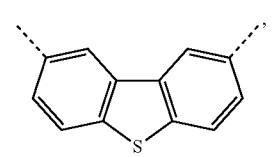
L22
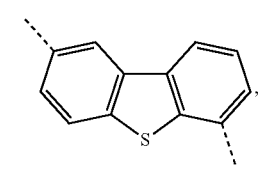
L23
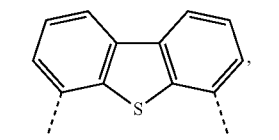
L24
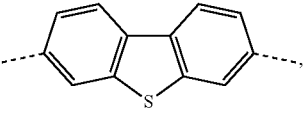
L25
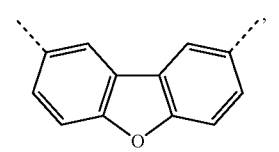
L26
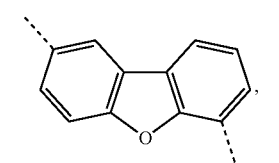
-continued
L27
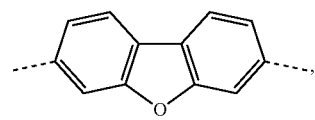
L28
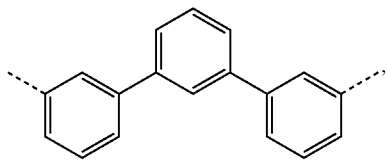
L29
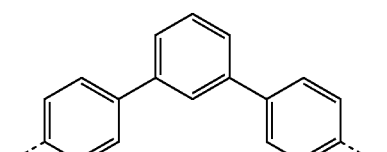
L30
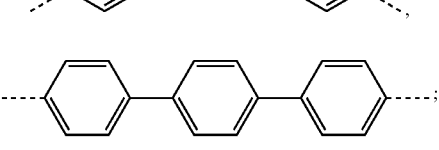
and
wherein C1 to C26 have the following structures:
C1
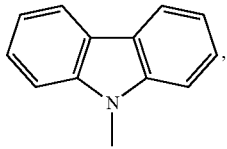
C2
C3
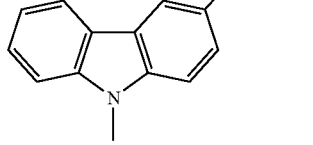
C4
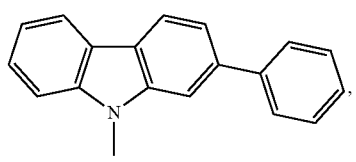

171
-continued
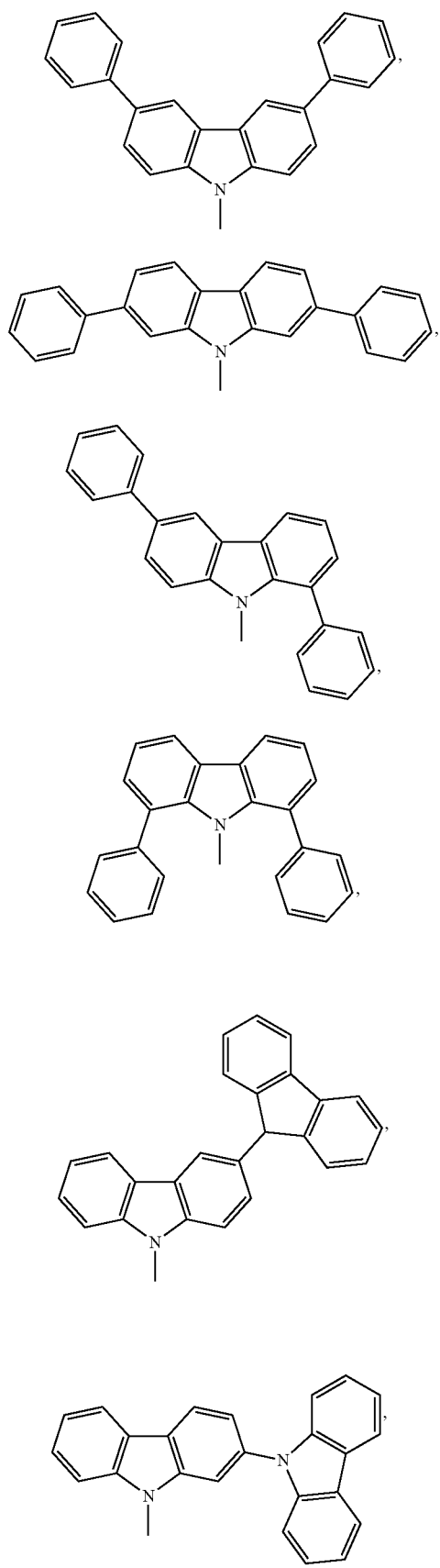
172
-continued
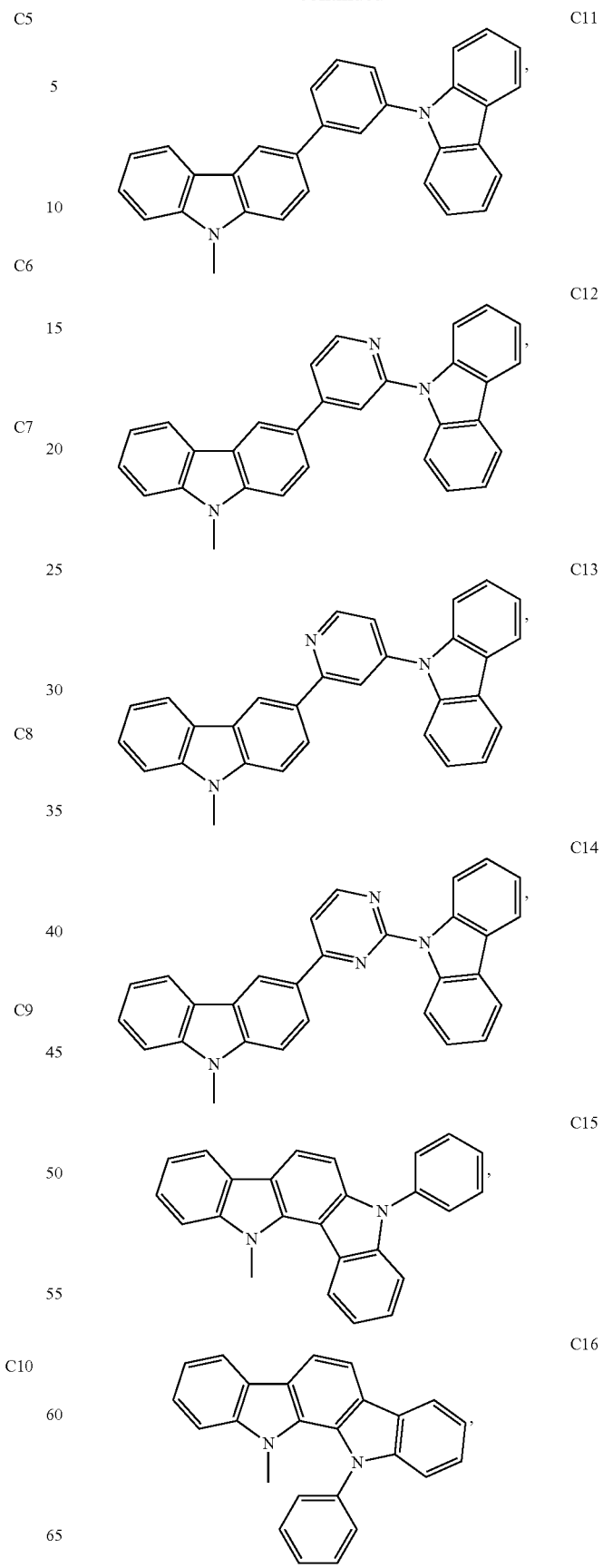

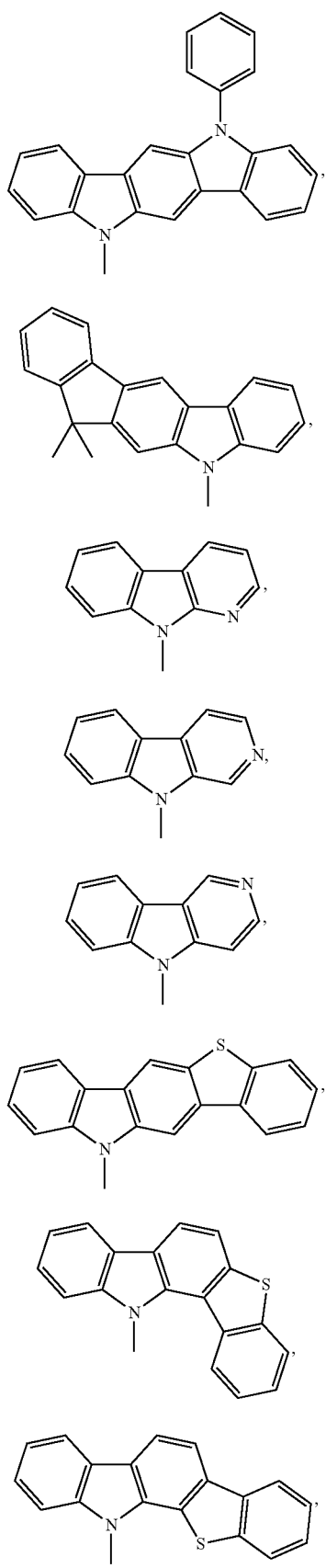
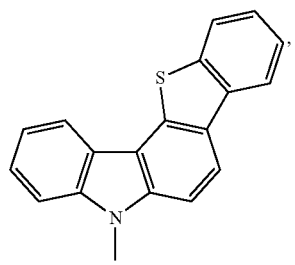
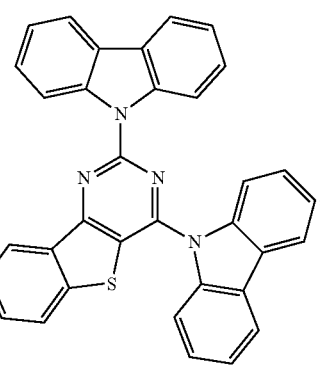
16. The compound of claim 1, wherein the compound is selected from the group consisting of:
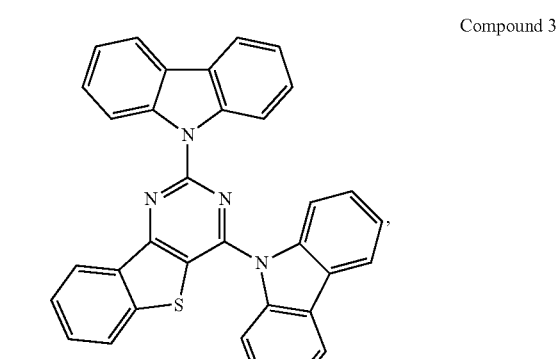

Compound 61
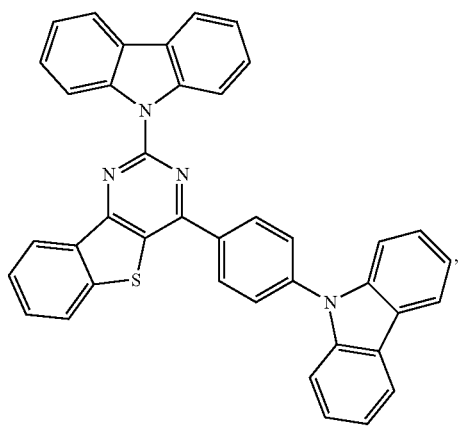
Compound 121
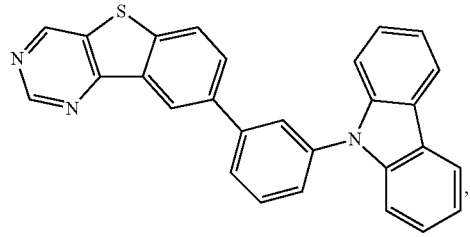
Compound 161
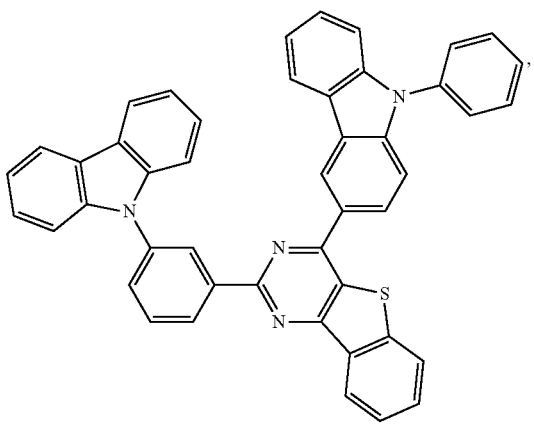
Compound 62
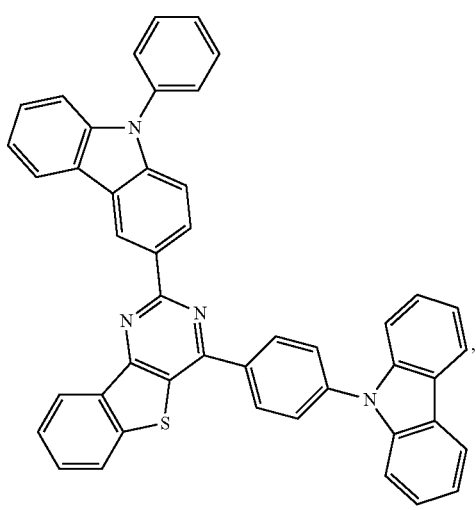
Compound 236
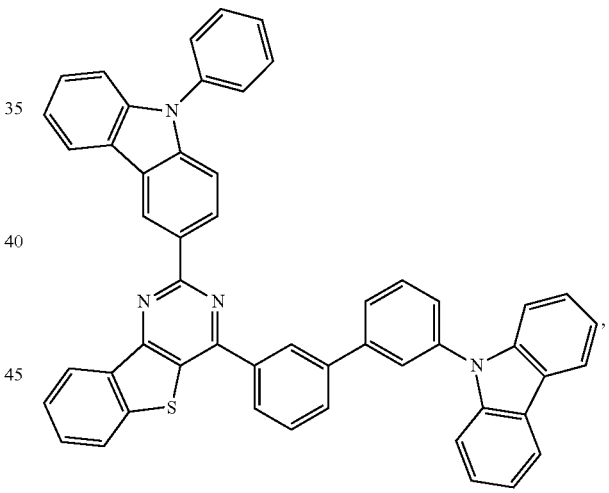
Compound 103
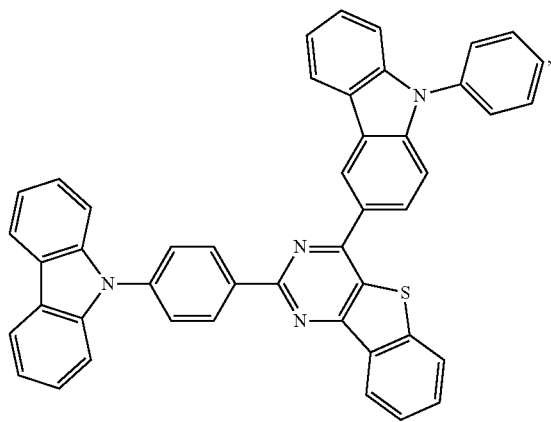
Compound 1742
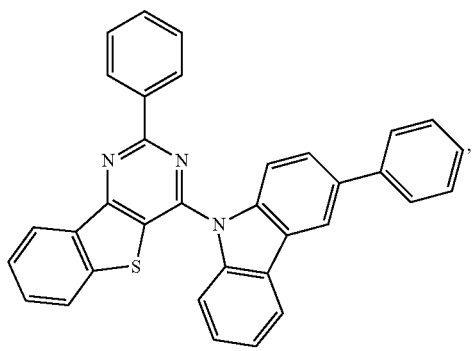

Compound 3481
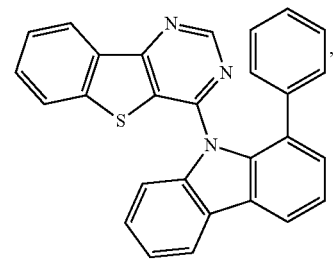
Compound 3484
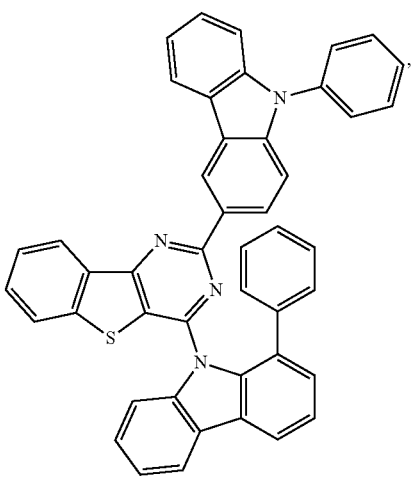
Compound 3539
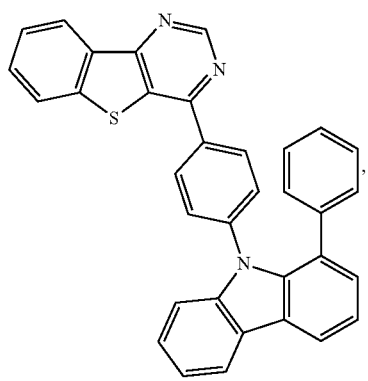
Compound 6961
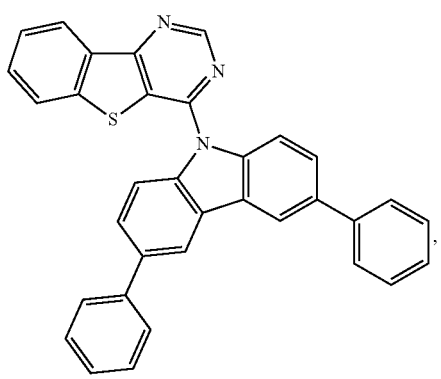
Compound 6962
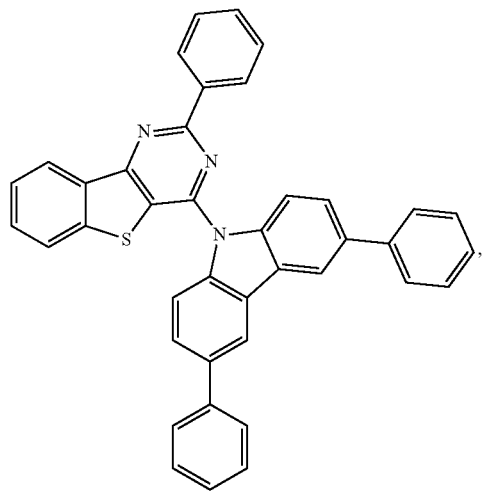
Compound 6987
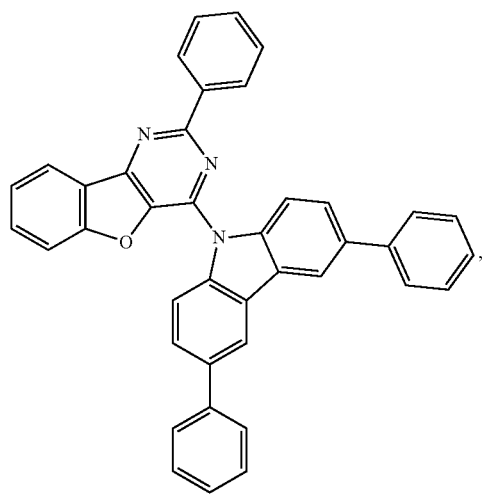
Compound 7063
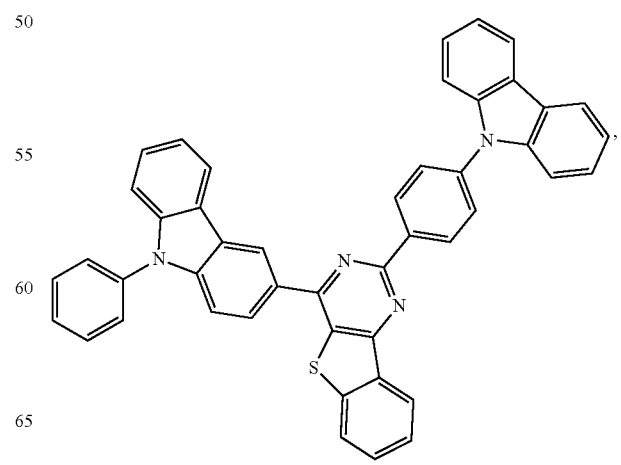

-continued
Compound 7121
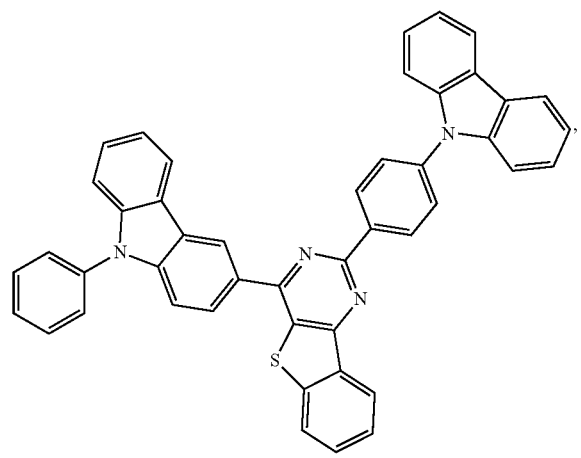
Compound 13921
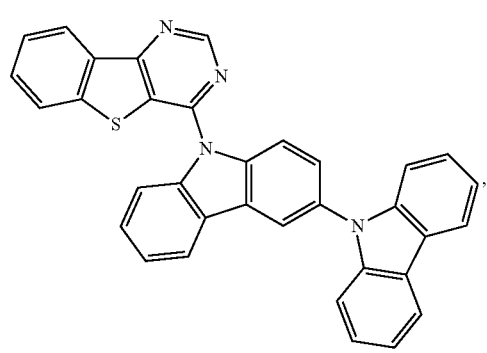
Clompound 13922
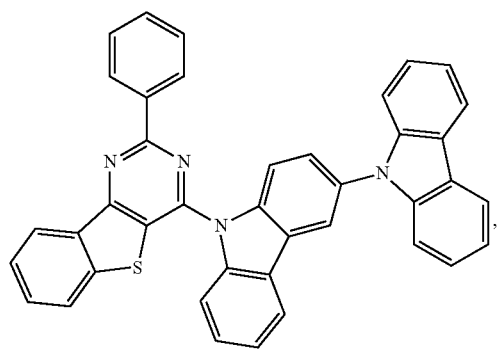
Compound 13923
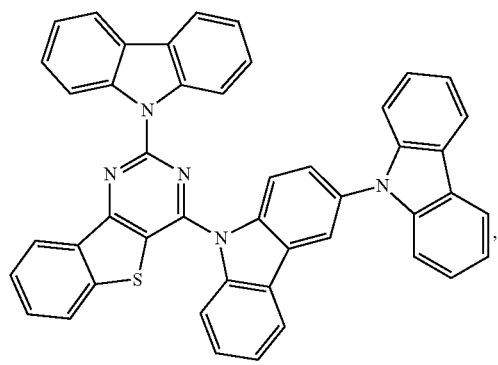
-continued
Compound 13924
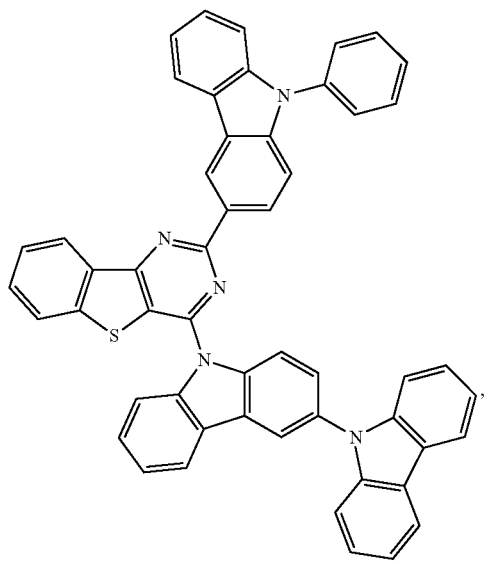
Cp,[pimd 13929
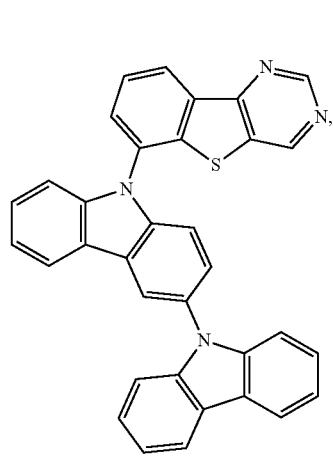
Compound 13935
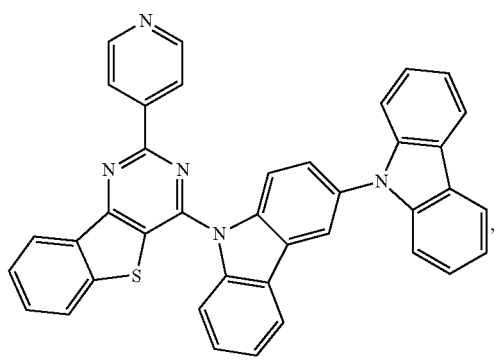

-continued
Compound 13936
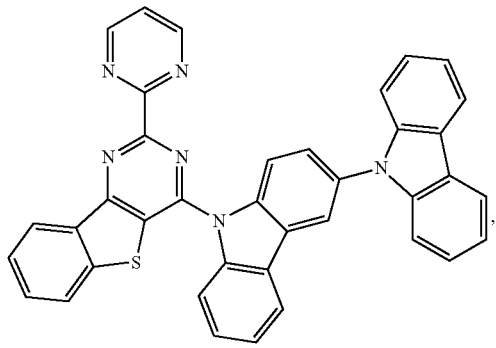
Compound 13979
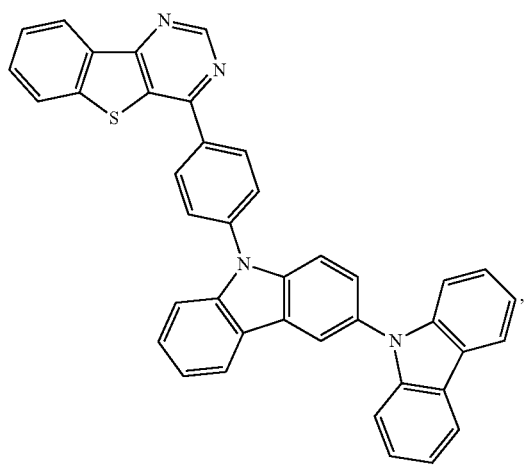
Compound 13981
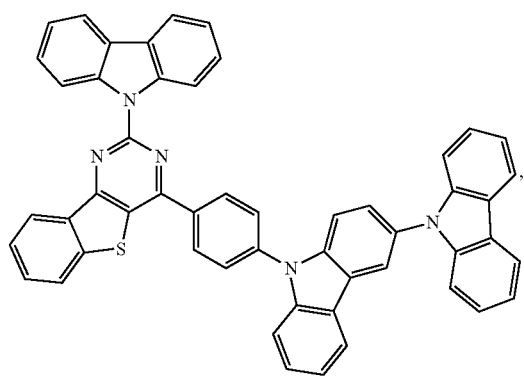
Compound 14037
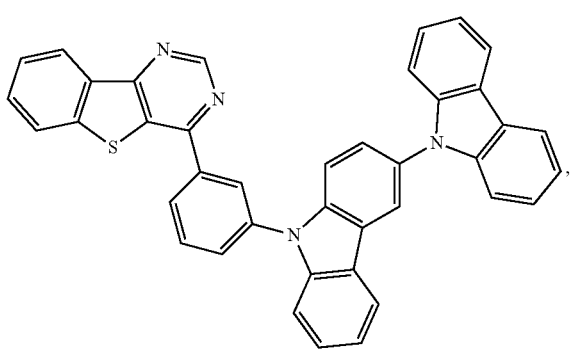
-continued
Compound 14038
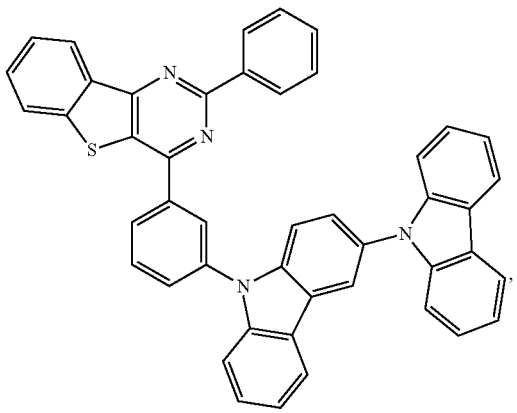
Compound 15661
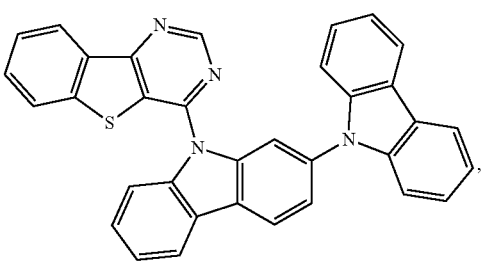
Compound 15662
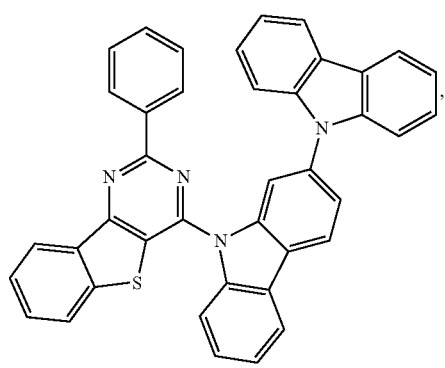
Compound 15663
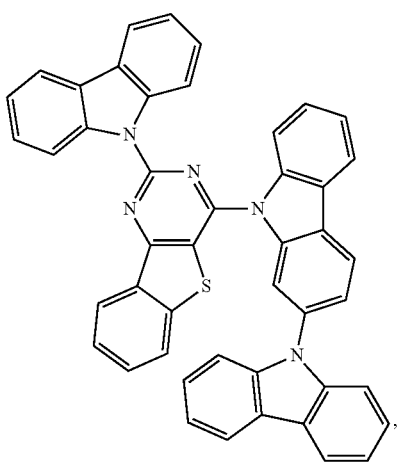

Compound 15665
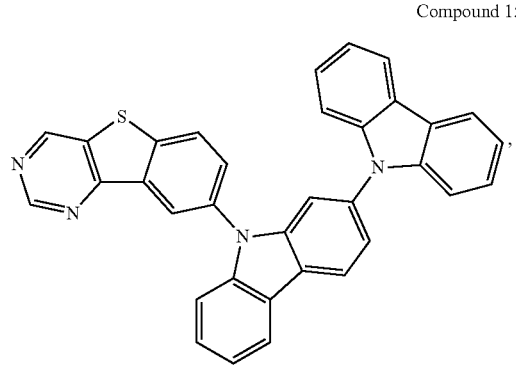
Compound 15669
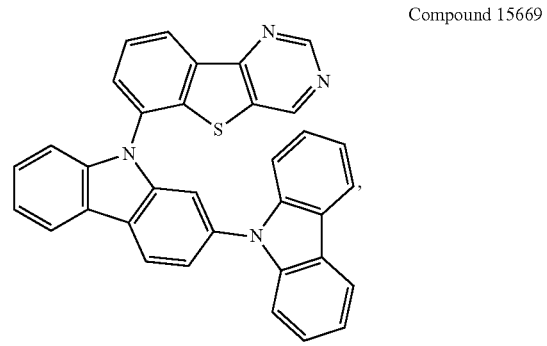
Compound 15719
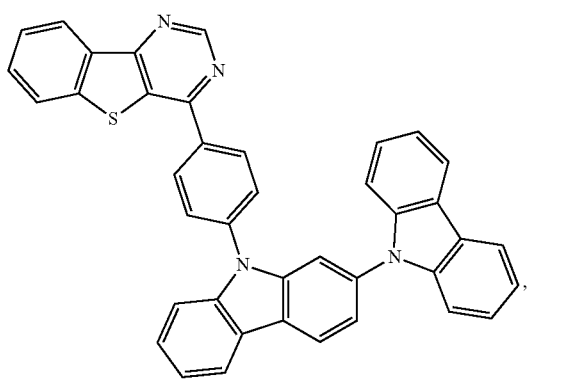
Compound 15777
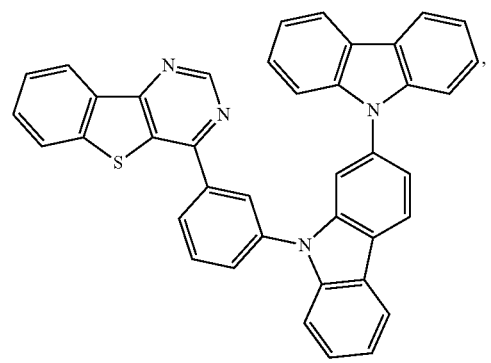
Compound 17401
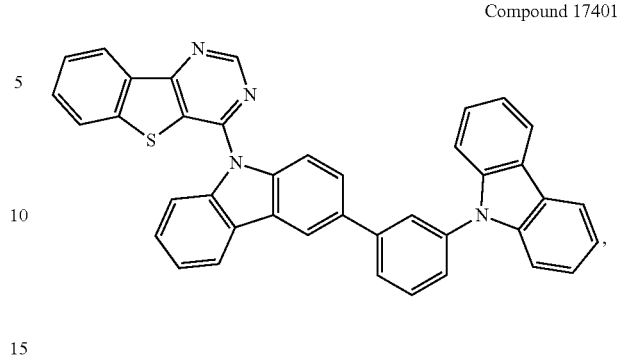
Compound 17459
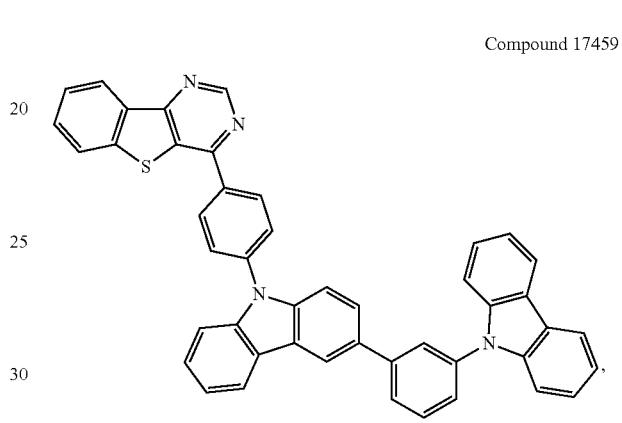
Compound 17517
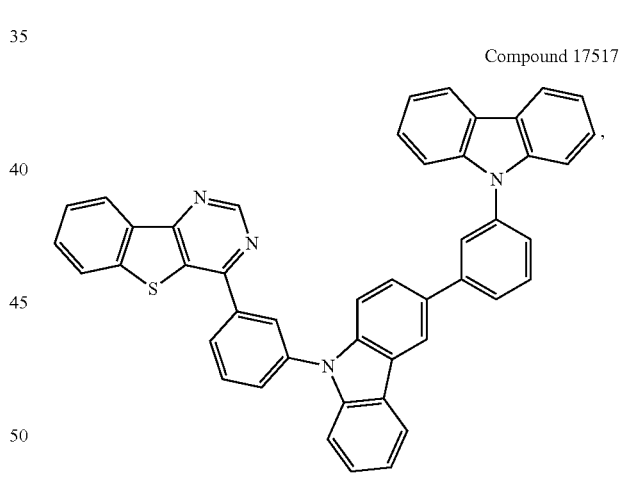
Compound 19141
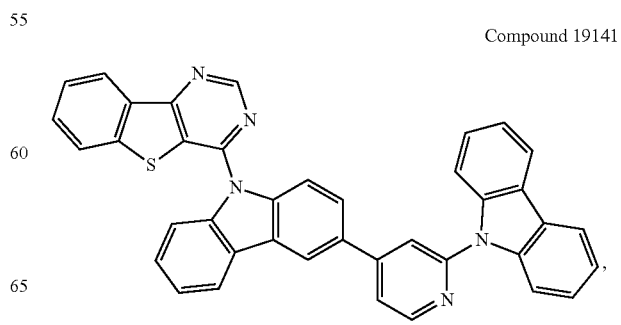

-continued

Compound 20881

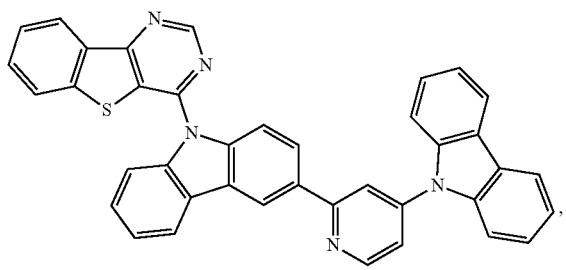

Compound 22621

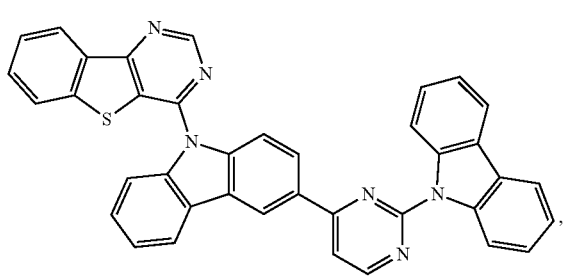

Compound 24361

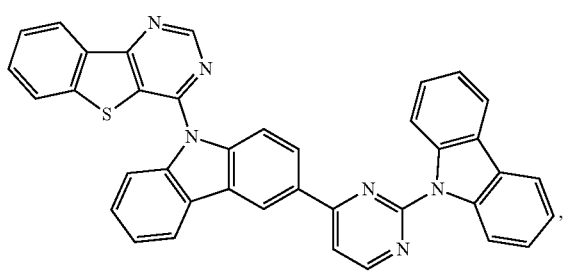

Compound 24362

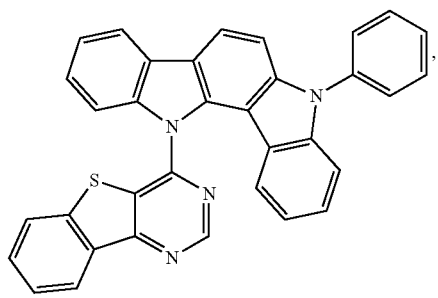

, and

-continued

Compound 24477

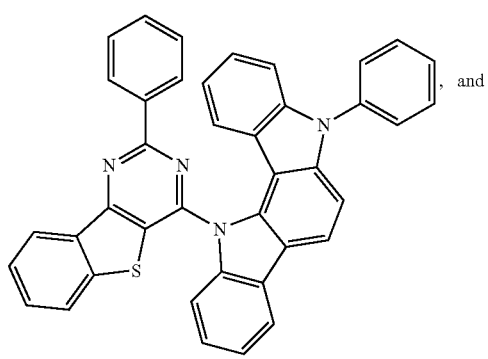

17. A first device comprising a first phosphorescent organic light-emitting device, the phosphorescent organic light-emitting device comprising:
    an anode;
    a cathode; and
    an organic layer, disposed between the anode and the cathode, comprising a compound having a formula $G^1$—L—$G^2$, Formula I;
    wherein $G^1$ has the structure:

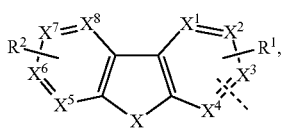

and
    $G^2$ has the structure:

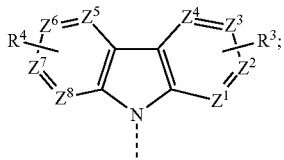

wherein L is selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
    wherein X is selected from the group consisting of O, S, and Se;
    wherein each of $X^1$, $X^2$, $X^3$, $X^4$, $X^5$, $X^6$, $X^7$, $X^8$, $Z^1$, $Z^2$, $Z^3$, $Z^4$, $Z^5$, $Z^6$, $Z^7$, and $Z^8$ is carbon or nitrogen;
    wherein at least two of $X^1$, $X^2$, $X^3$, $X^4$, $X^5$, $X^6$, $X^7$, and $X^8$ are nitrogen;

wherein at least one of $X^1$, $X^2$, $X^3$, and $X^4$ is carbon and bonded to L;

wherein the dashed lines represent the bonds between $G^1$ and L and $G^2$ and L;

wherein each $R^2$, $R^3$, and $R^4$ represent mono, di, tri, tetra substitutions or no substitution;

wherein $R^1$ represents mono, di, tri substitutions or no substitution;

wherein $R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein the substitution is optionally fused to $G^1$ or $G^2$; and wherein when $R^3$ or $R^4$ is carbazole or substituted carbazole, the carbazole or substituted carbazole is connected to $G^2$ by N.

18. The first device of claim 17, wherein the organic layer is an emissive layer and the compound of Formula I is a host.

19. The first device of claim 17, wherein the organic layer further comprising a phosphorescent emissive dopant.

20. The first device of claim 19, wherein the phosphorescent emissive dopant is a transition metal complex having at least one ligand selected from the group consisting of:

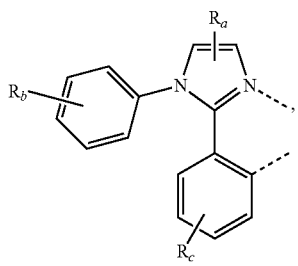

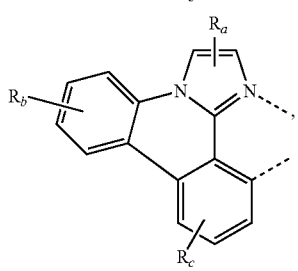

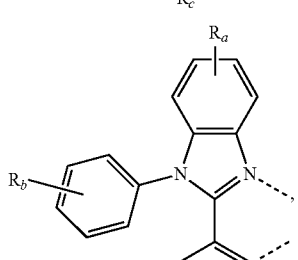

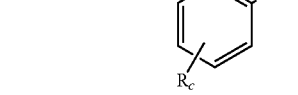

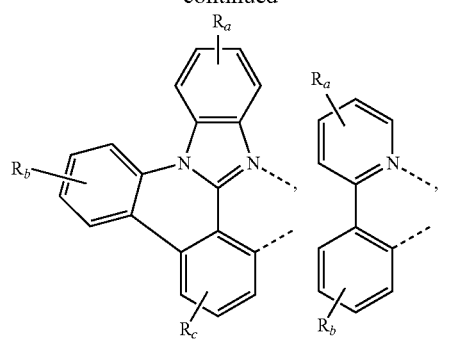

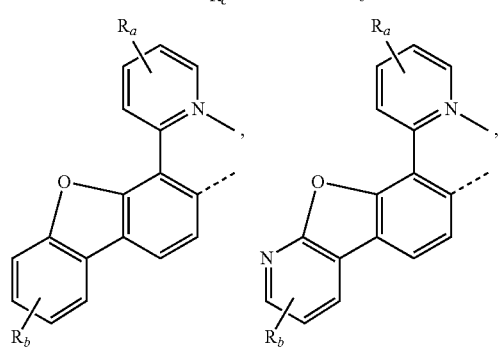

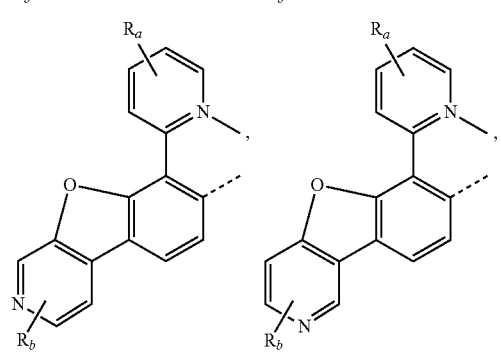

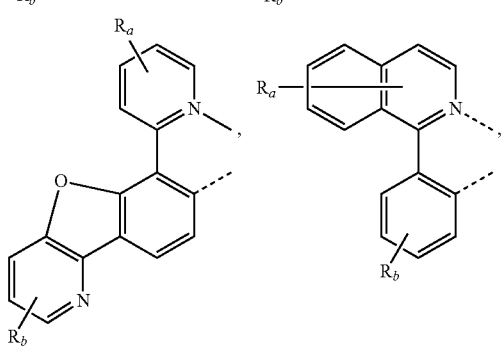

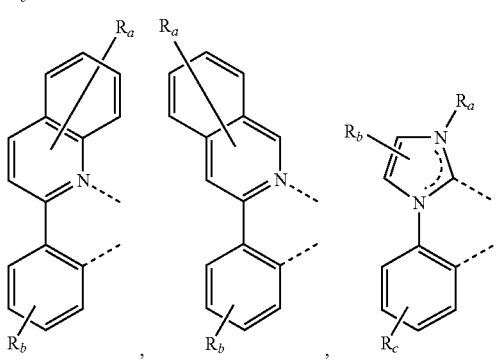

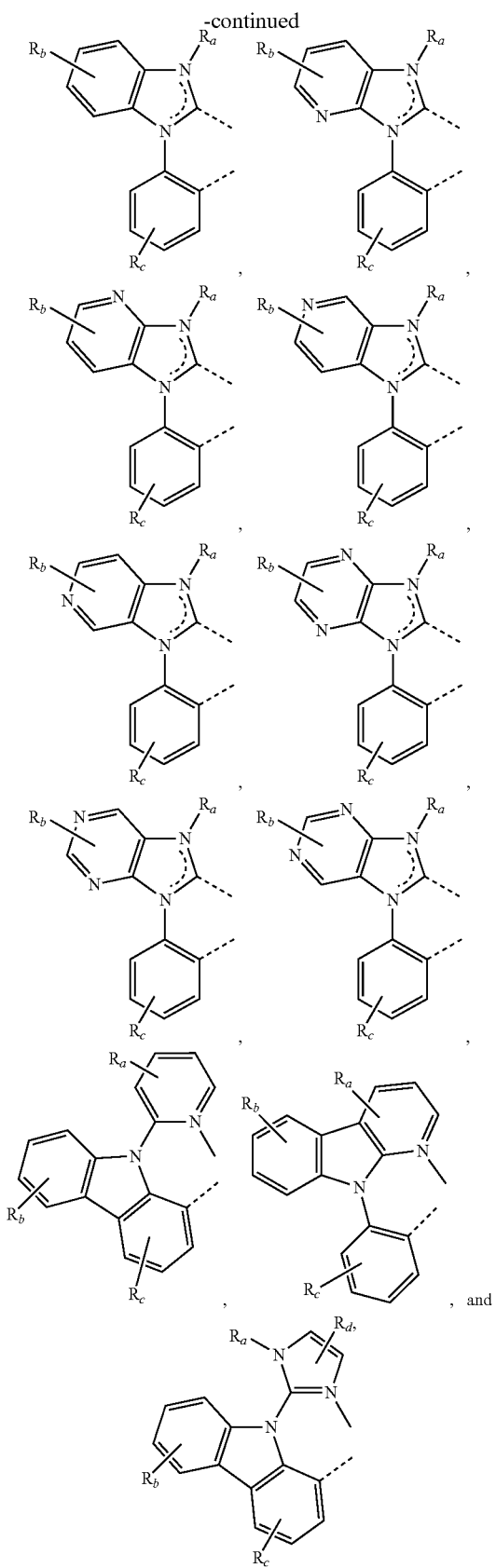

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

21. A formulation comprising a compound having a formula $G^1$—L—$G^2$, Formula I;

wherein $G^1$ has the structure:

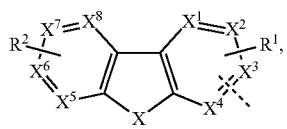

and $G^2$ has the structure:

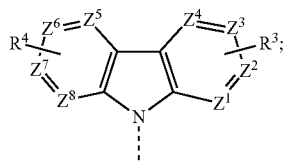

wherein L is selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein X is selected from the group consisting of O, S, and Se;

wherein each of $X^1$, $X^2$, $X^3$, $X^4$, $X^5$, $X^6$, $X^7$, $X^8$, $Z^1$, $Z^2$, $Z^3$, $Z^4$, $Z^5$, $Z^6$, $Z^7$, and $Z^8$ is carbon or nitrogen;

wherein at least two of $X^1$, $X^2$, $X^3$, $X^4$, $X^5$, $X^6$, $X^7$, and $X^8$ are nitrogen;

wherein at least one of $X^1$, $X^2$, $X^3$, and $X^4$ is carbon and bonded to L;

wherein the dashed lines represent the bonds between $G^1$ and L and $G^2$ and L;

wherein each $R^2$, $R^3$, and $R^4$ represent mono, di, tri, tetra substitutions or no substitution;

wherein $R^1$ represents mono, di, tri substitutions or no substitution;

wherein $R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein the substitution is optionally fused to $G^1$ or $G^2$; and wherein when $R^3$ or $R^4$ is carbazole or substituted carbazole, the carbazole or substituted carbazole is connected to $G^2$ by N.

* * * * *

UNITED STATES PATENT AND TRADEMARK OFFICE
CERTIFICATE OF CORRECTION

PATENT NO. : 9,502,656 B2
APPLICATION NO. : 14/188025
DATED : November 22, 2016
INVENTOR(S) : Scott Joseph et al.

Page 1 of 20

It is certified that error appears in the above-identified patent and that said Letters Patent is hereby corrected as shown below:

In the Specification

Column 22, Lines 50-66, please delete

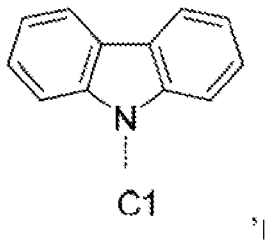

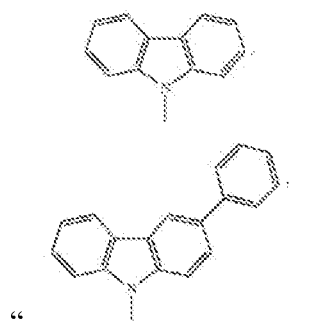

" and insert --

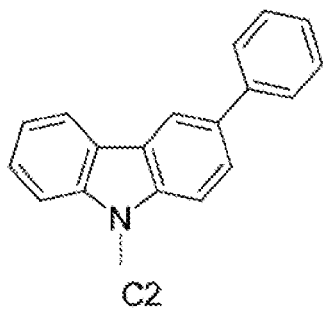

--

Signed and Sealed this
Twenty-fifth Day of July, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,502,656 B2

Column 23, Lines 1-27, please delete "

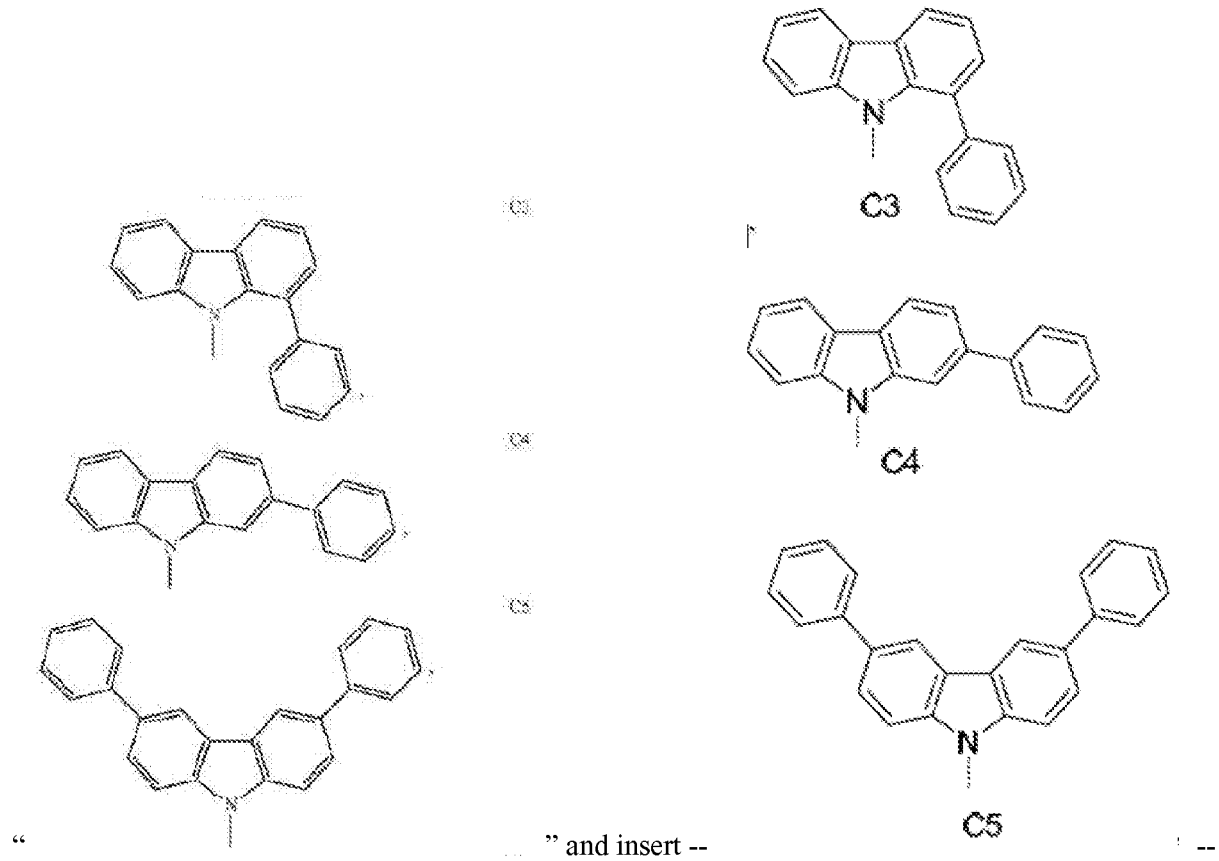

" and insert --

Column 23, Lines 28-45, please delete "

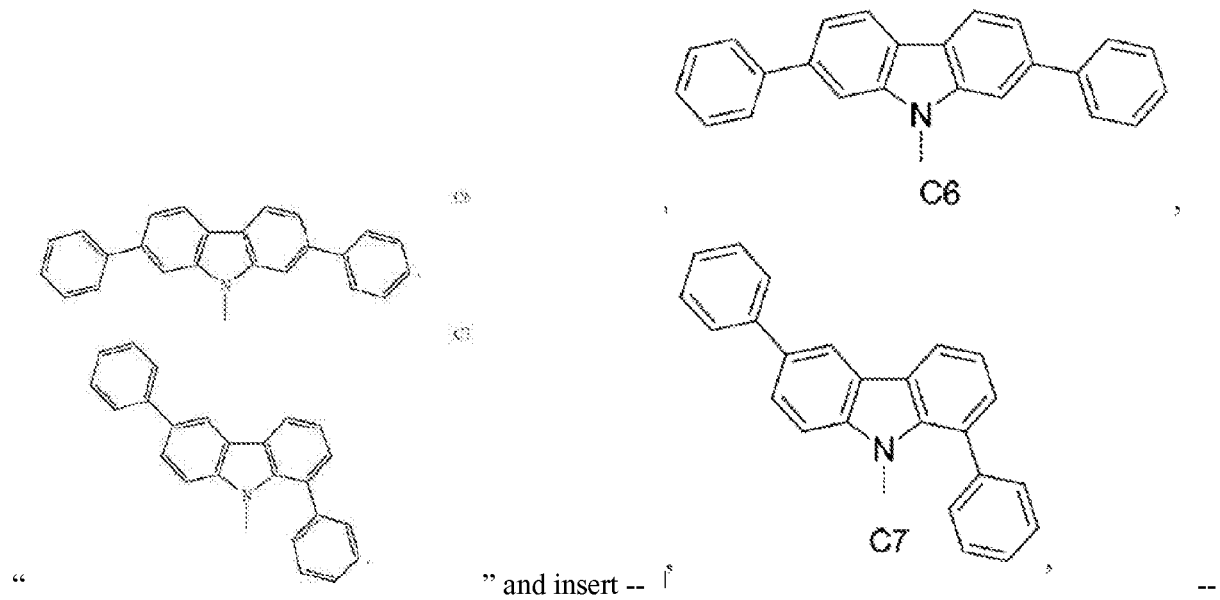

" and insert -- --

CERTIFICATE OF CORRECTION (continued)
U.S. Pat. No. 9,502,656 B2

Column 23, Lines 46-66, please delete

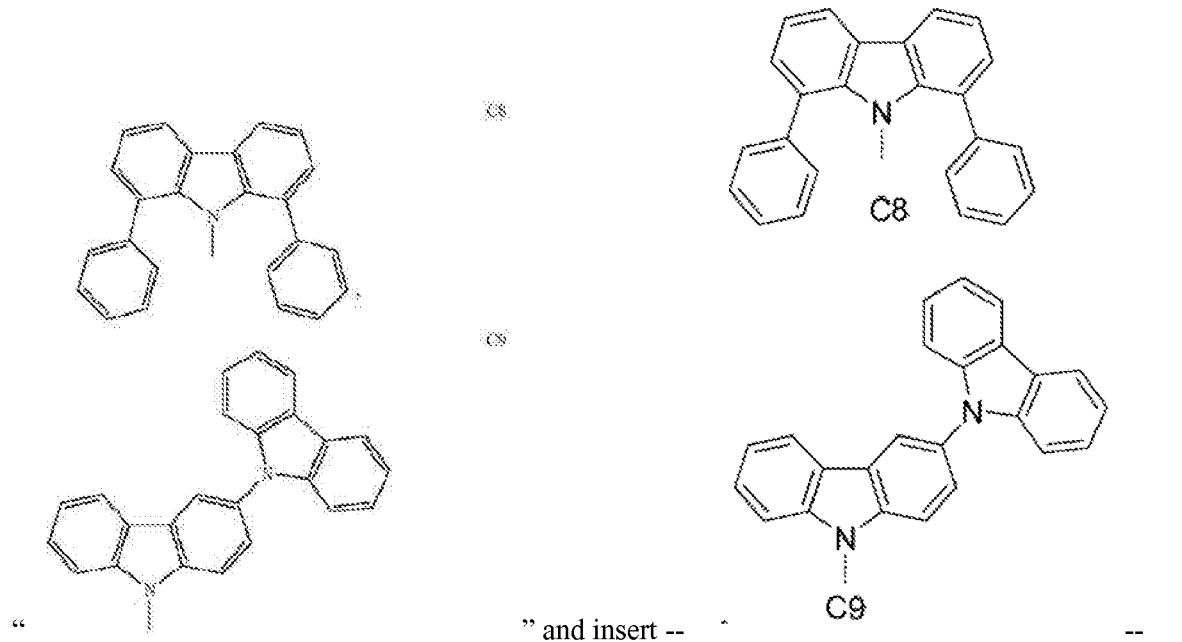

" and insert --

Column 24, Lines 1-24, please delete

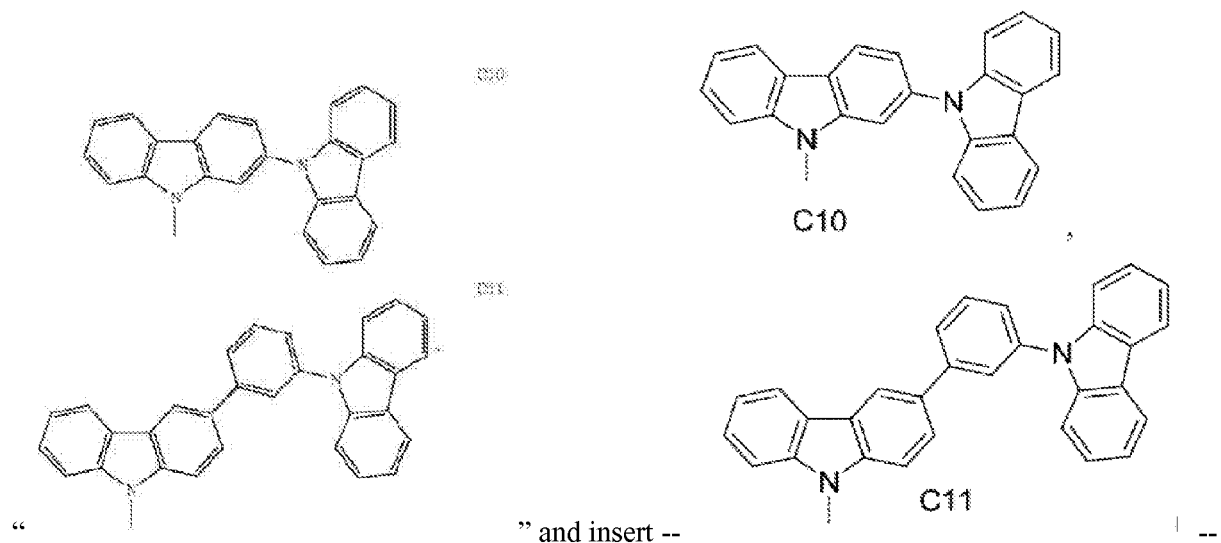

" and insert -- --

CERTIFICATE OF CORRECTION (continued)
U.S. Pat. No. 9,502,656 B2

Column 24, Lines 25-45, please delete

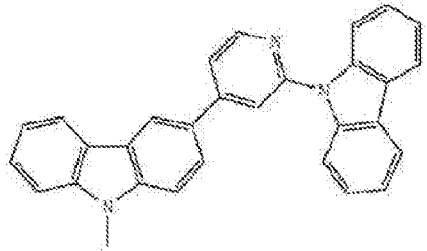

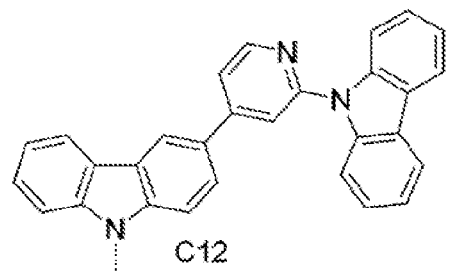

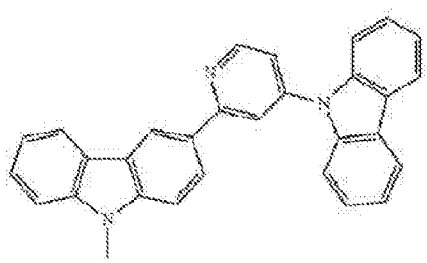

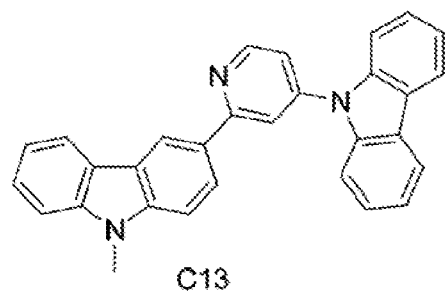

" and insert --

Column 24, Lines 46-66, please delete

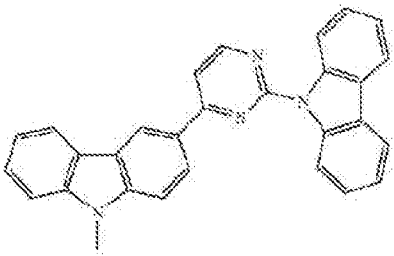

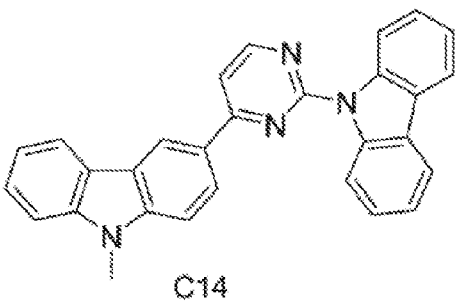

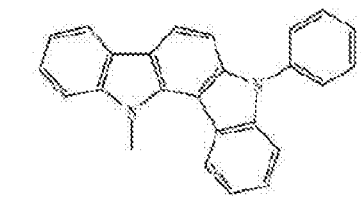

" and insert --

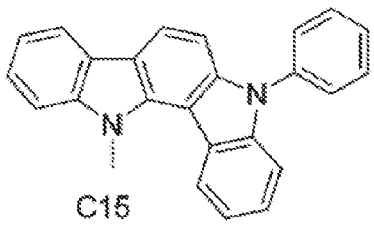

--

CERTIFICATE OF CORRECTION (continued)
U.S. Pat. No. 9,502,656 B2

Column 25, Lines 1-24, please delete

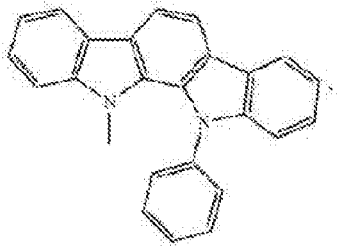
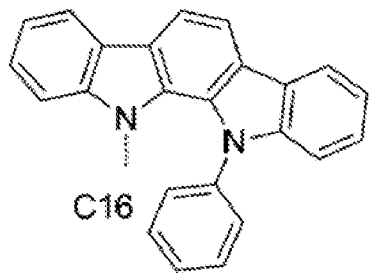
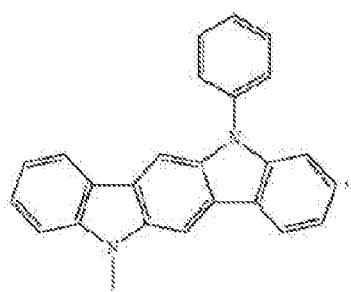
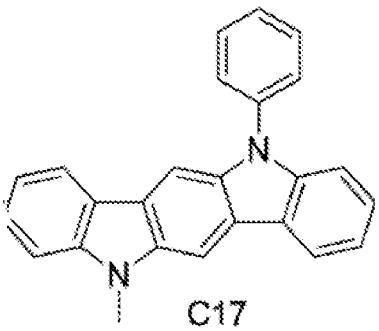

" and insert --   --

Column 25, Lines 25-49, please delete

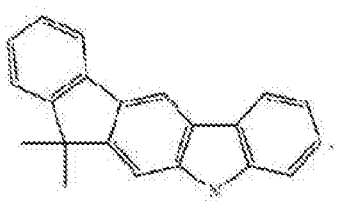
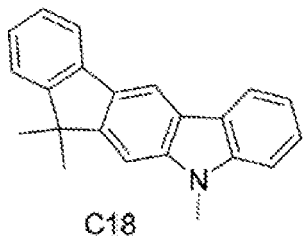
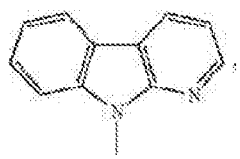
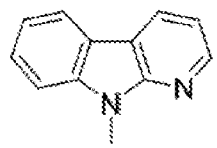
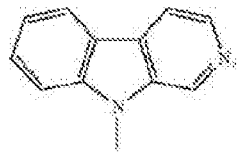
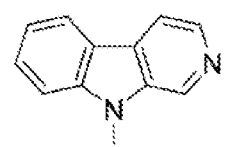

" and insert --   --

Column 25, Lines 50-66, please delete

Column 26, Lines 1-16, please delete
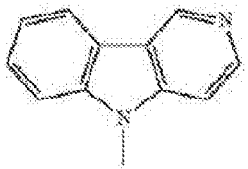
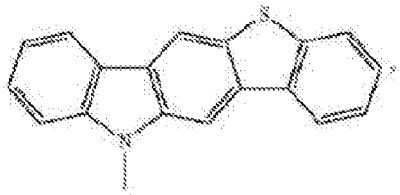
" and insert --
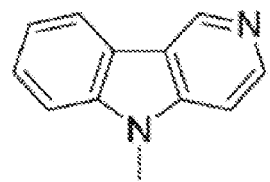
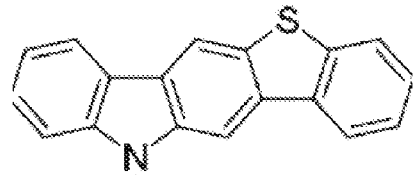
--
Column 26, Lines 17-38, please delete
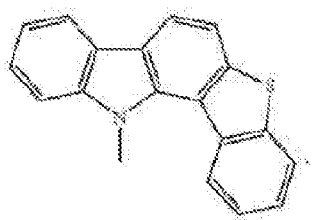
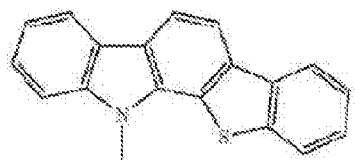
" and insert --
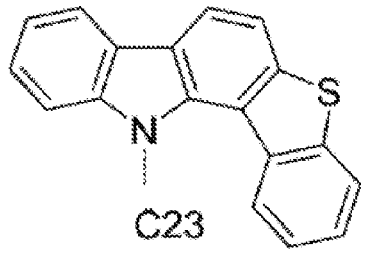
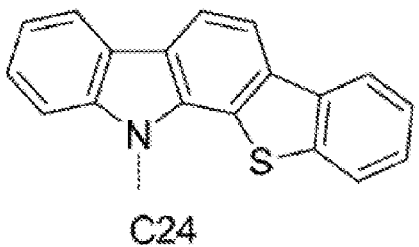
--

CERTIFICATE OF CORRECTION (continued)
U.S. Pat. No. 9,502,656 B2

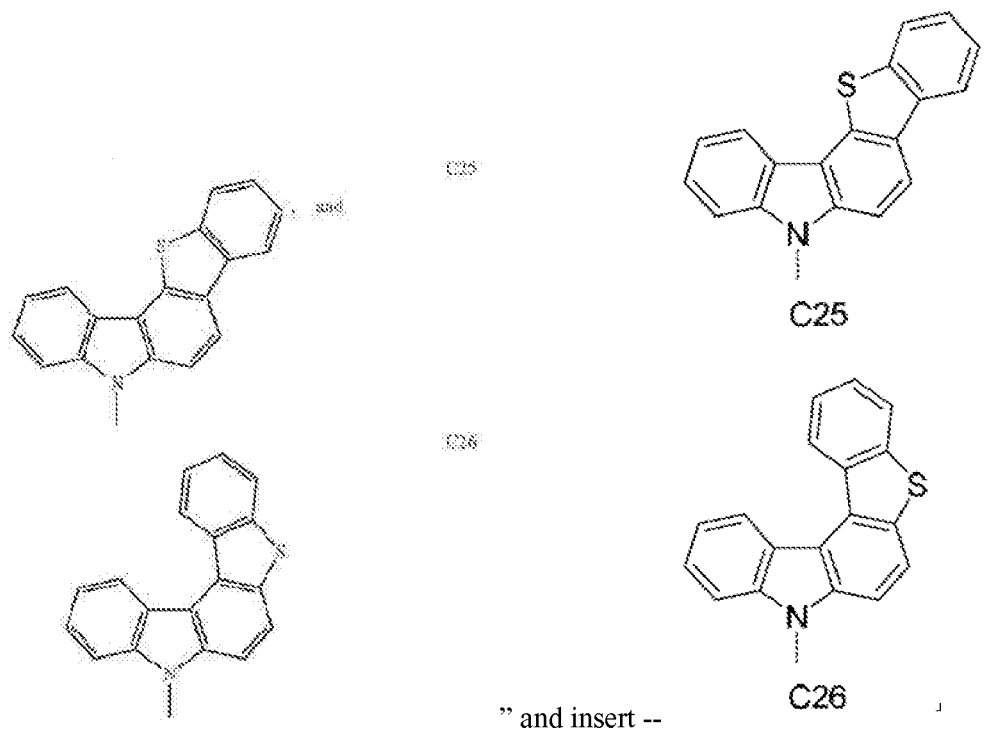

" and insert --  --

Column 42, Lines 42-64, please delete

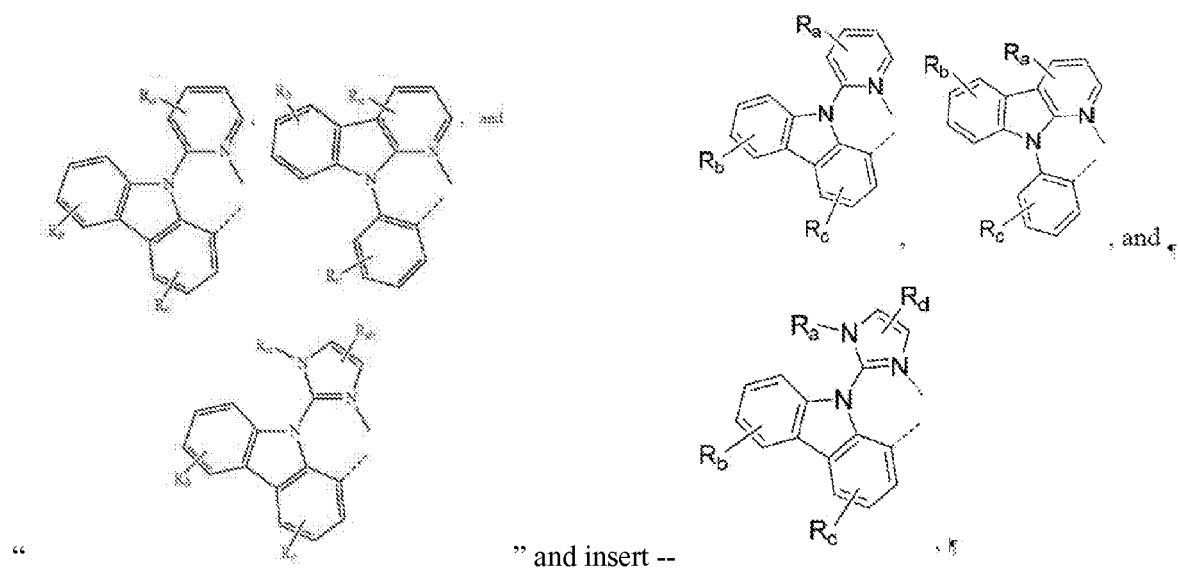

" and insert --  --

Column 58, Line 2, please delete "sold" and insert -- solid --

Column 149, Lines 51-66, please delete

CERTIFICATE OF CORRECTION (continued)
U.S. Pat. No. 9,502,656 B2

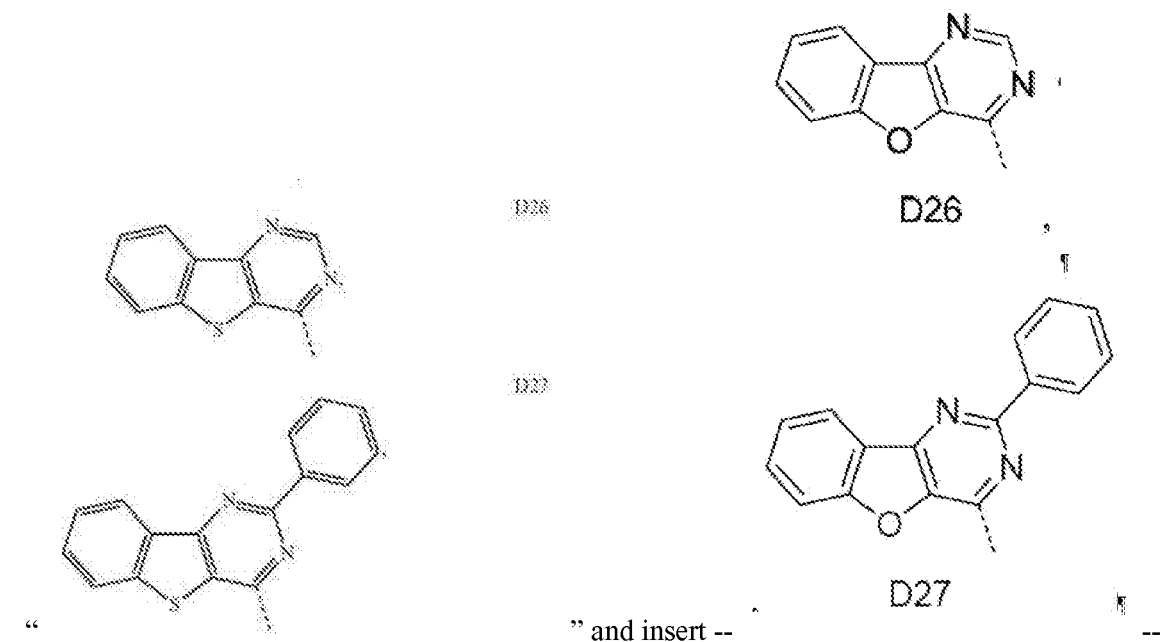

In the Claims

Column 156, Lines 26-42, please delete

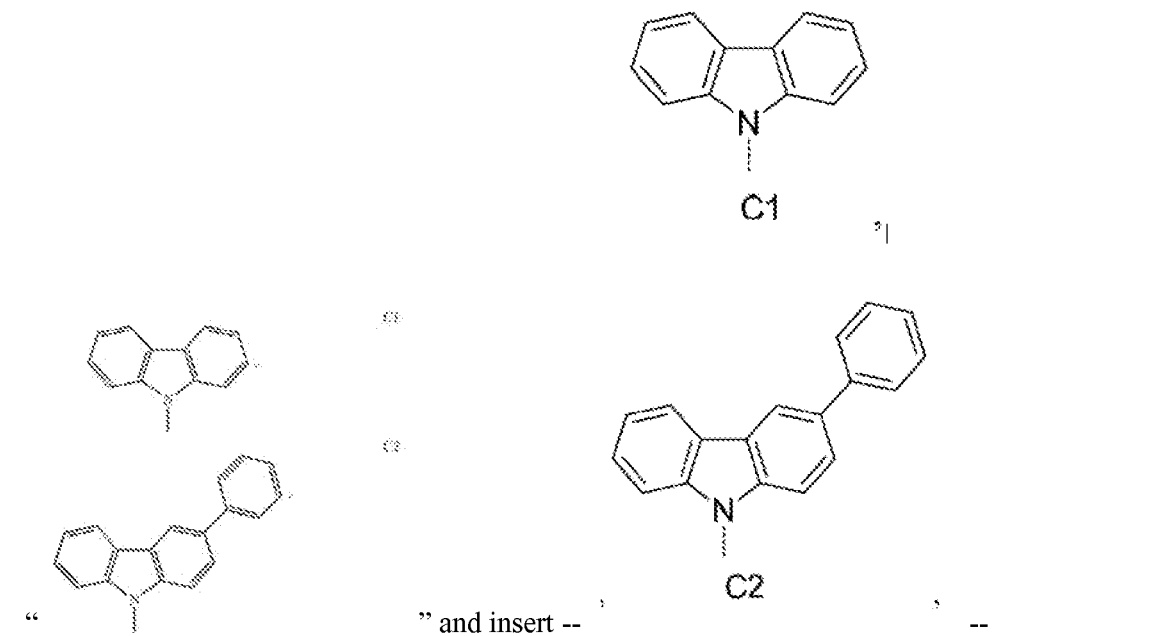

Column 156, Lines 43-66, please delete

CERTIFICATE OF CORRECTION (continued)
U.S. Pat. No. 9,502,656 B2

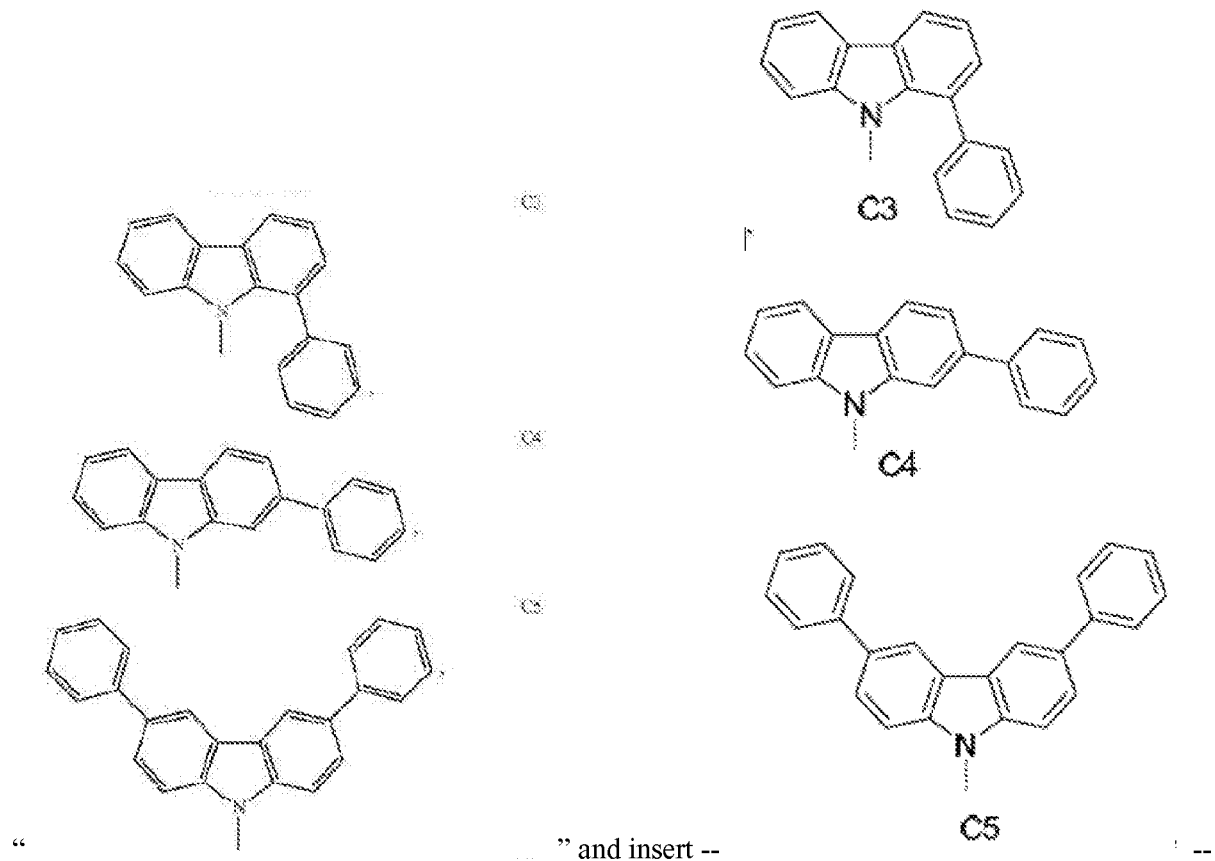

Column 157, Lines 1-22, please delete

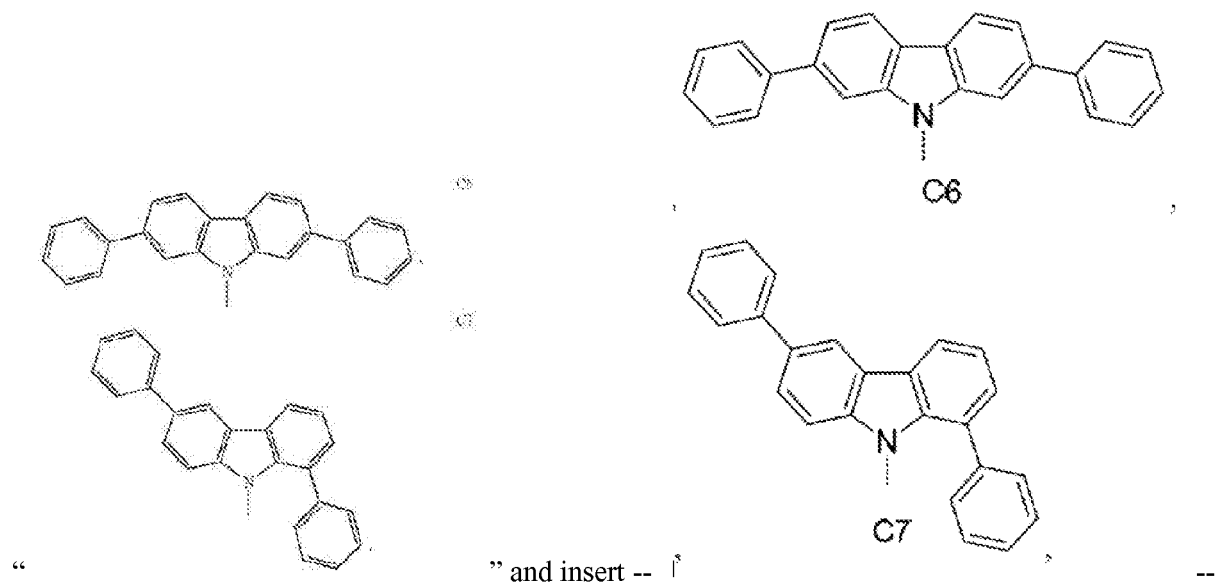

Column 157, Lines 23-44, please delete

CERTIFICATE OF CORRECTION (continued)
U.S. Pat. No. 9,502,656 B2

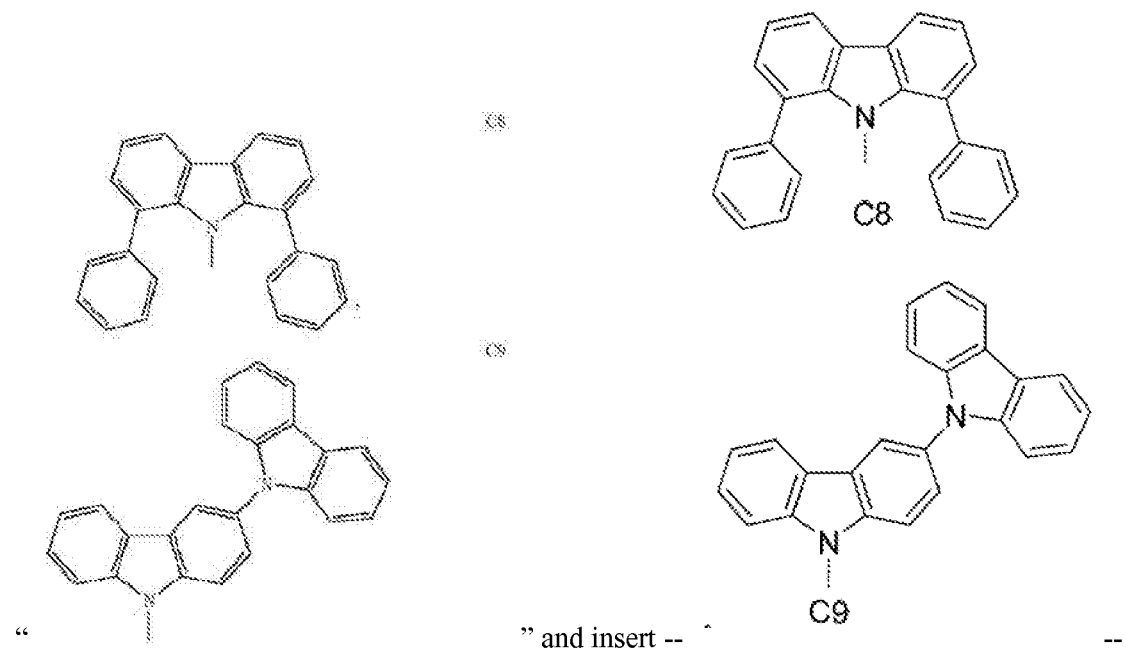

" and insert --

Column 157, Lines 45-66, please delete

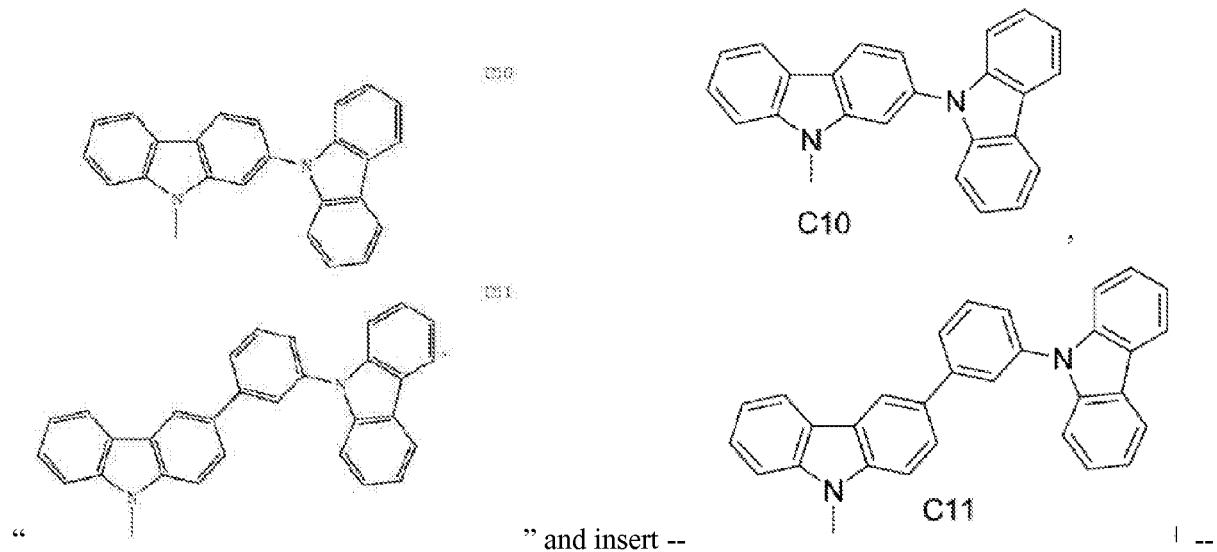

" and insert --

Column 158, Lines 1-24, please delete

CERTIFICATE OF CORRECTION (continued)
U.S. Pat. No. 9,502,656 B2

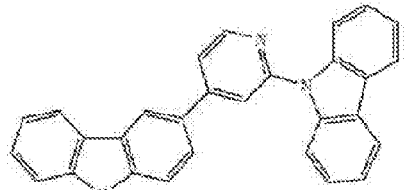 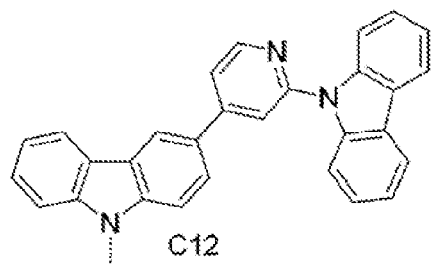

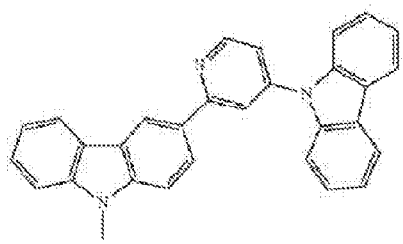 " and insert -- 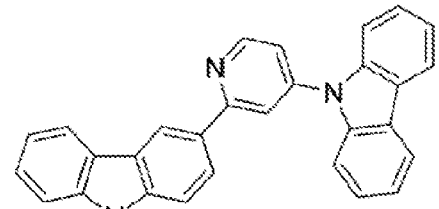 --

Column 158, Lines 25-44, please delete

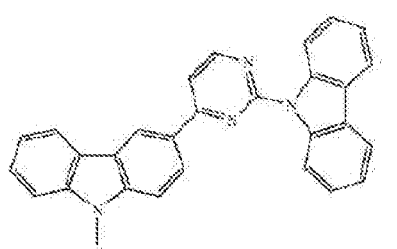 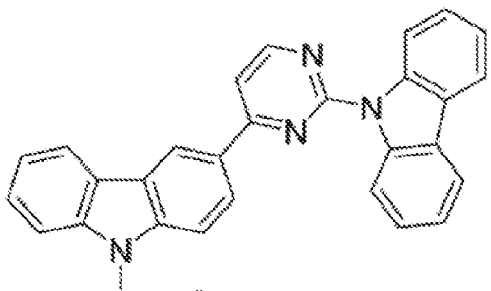

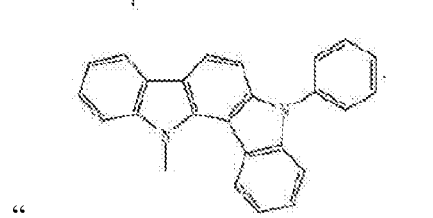 " and insert -- 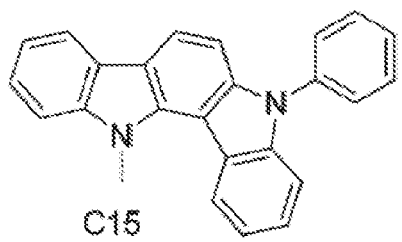 --

Column 158, Lines 45-66, please delete "

CERTIFICATE OF CORRECTION (continued)
U.S. Pat. No. 9,502,656 B2

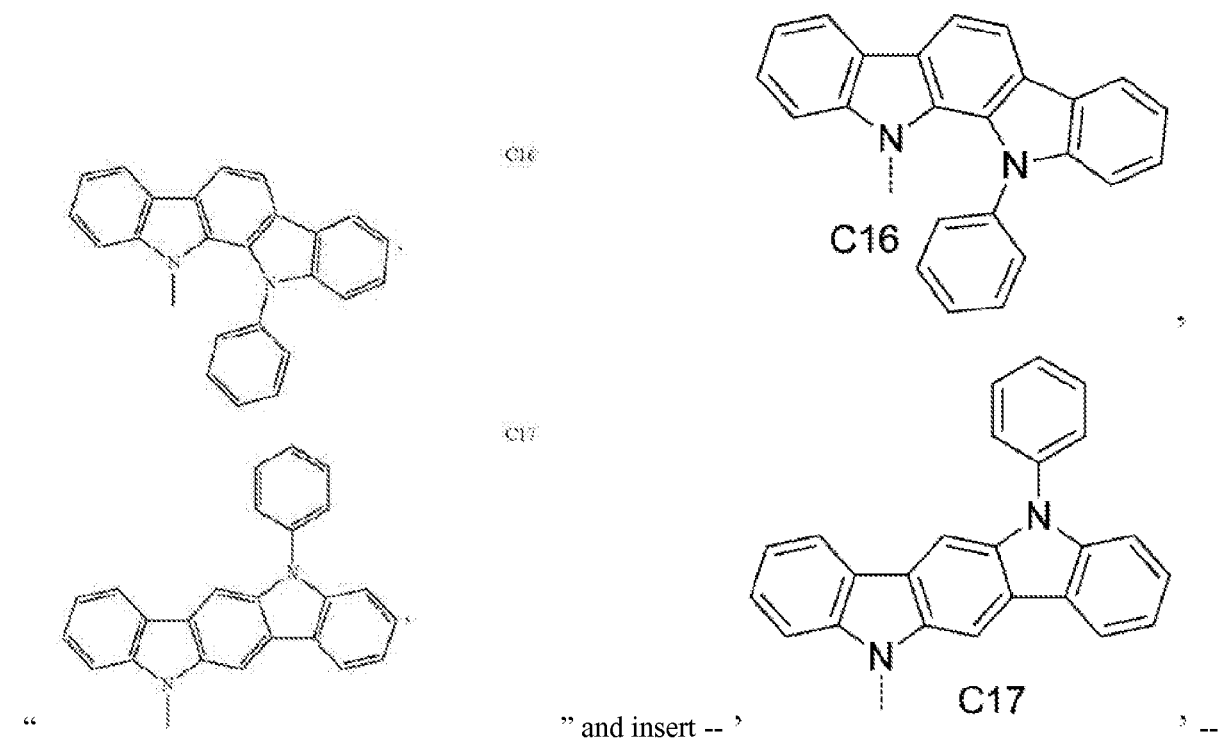

" and insert -- '

Column 159, Lines 1-24, please delete

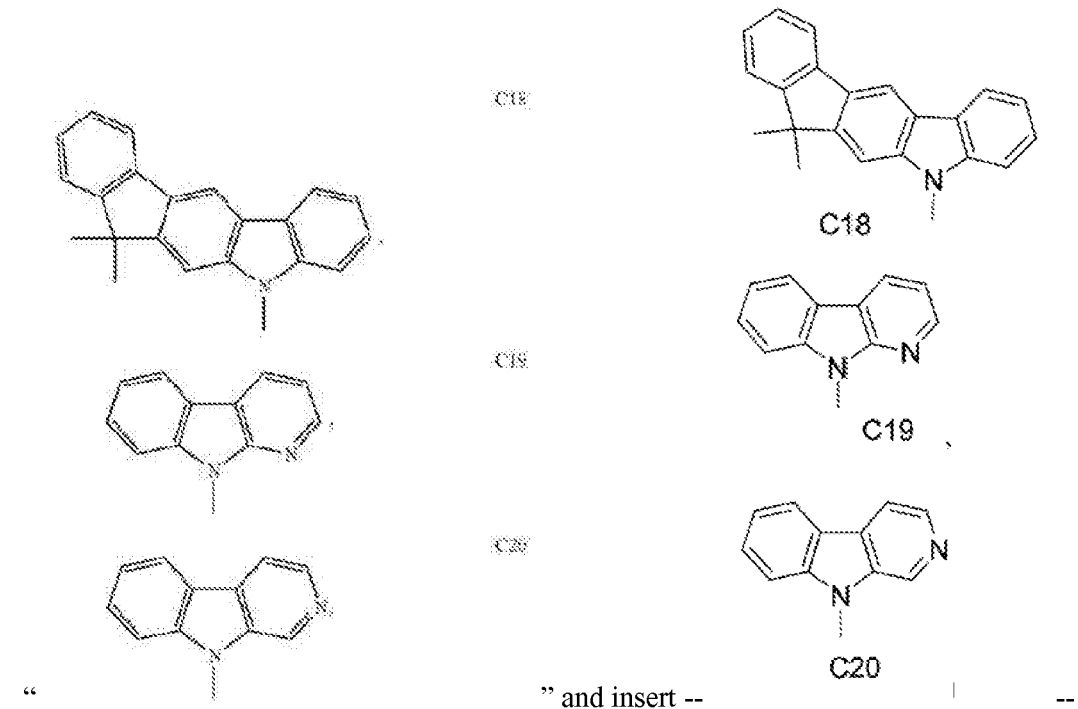

" and insert --

Column 159, Lines 25-41, please delete

Column 159, Lines 42-55, please delete
" 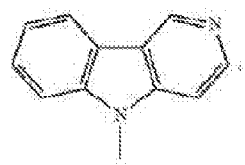 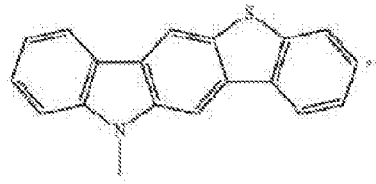 " and insert -- 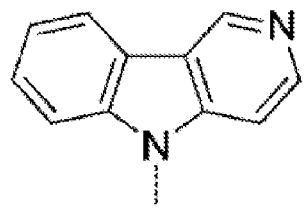 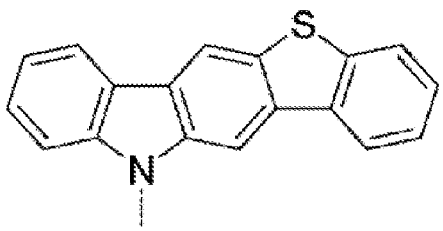 --
Column 159, Lines 56-66, please delete
" 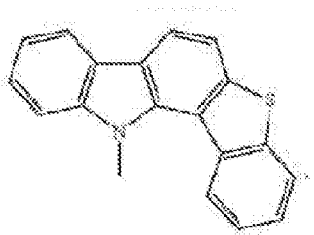 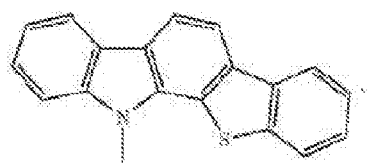 " and insert -- 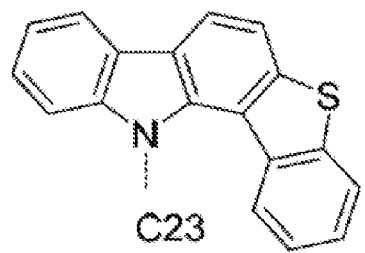 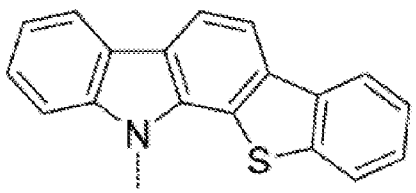 --

CERTIFICATE OF CORRECTION (continued)
U.S. Pat. No. 9,502,656 B2

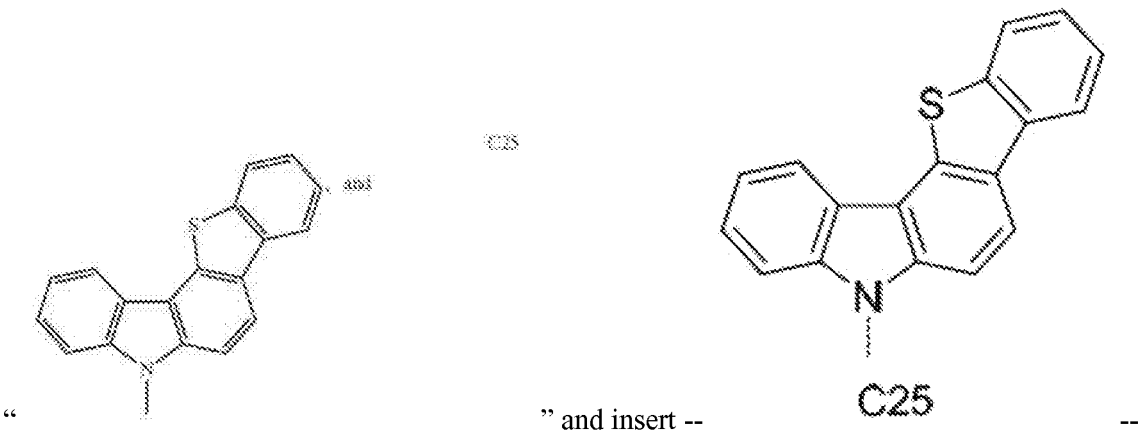

Column 160, Lines 1-14, please delete

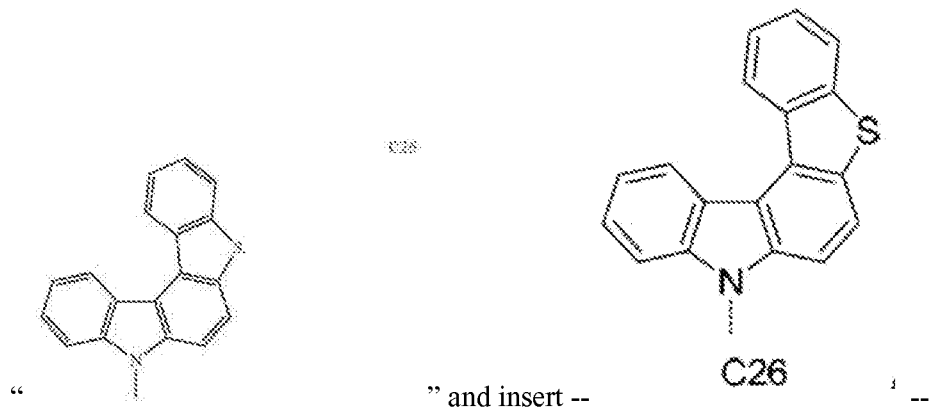

Column 170, Lines 33-66, please delete

CERTIFICATE OF CORRECTION (continued)
U.S. Pat. No. 9,502,656 B2

Column 171, Lines 1-31, please delete " 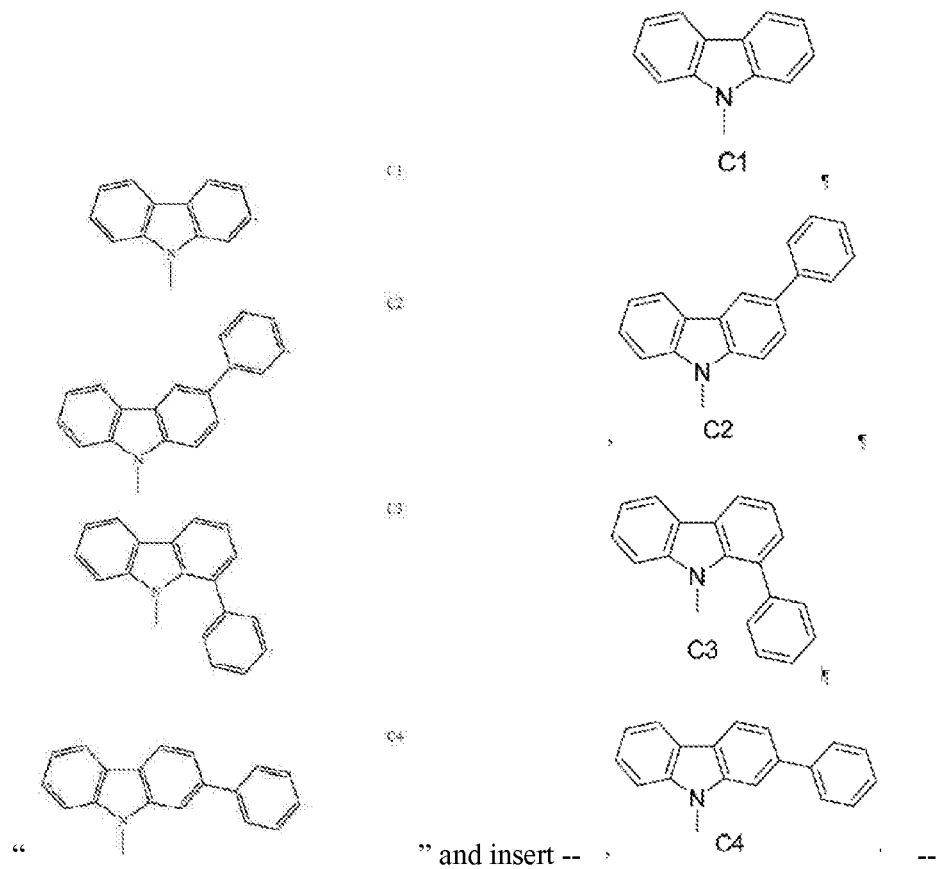 " and insert -- --

Column 171, Lines 32-66, please delete " 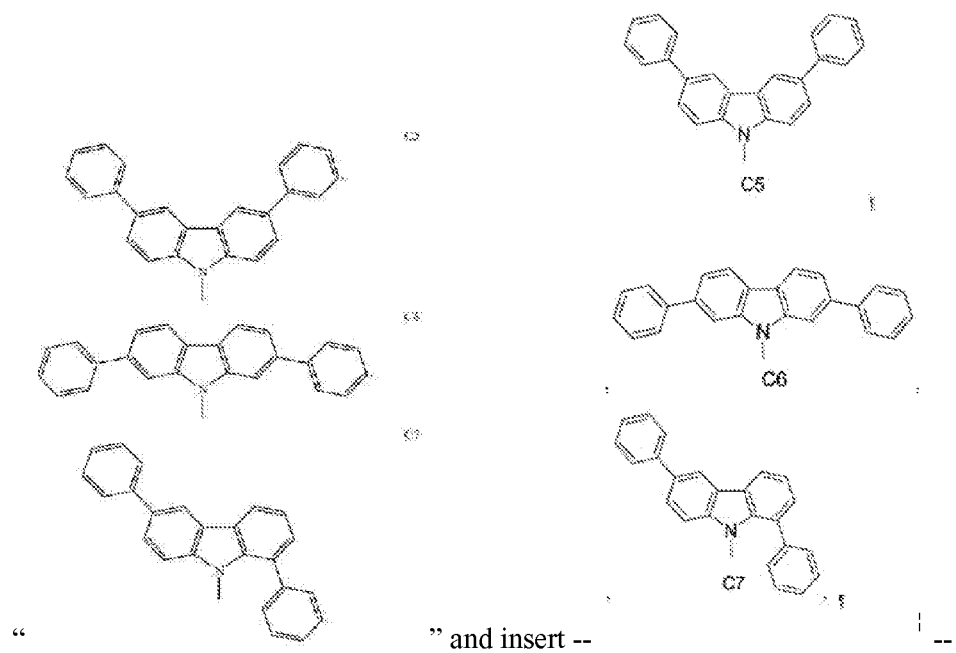 " and insert -- --

CERTIFICATE OF CORRECTION (continued)
U.S. Pat. No. 9,502,656 B2

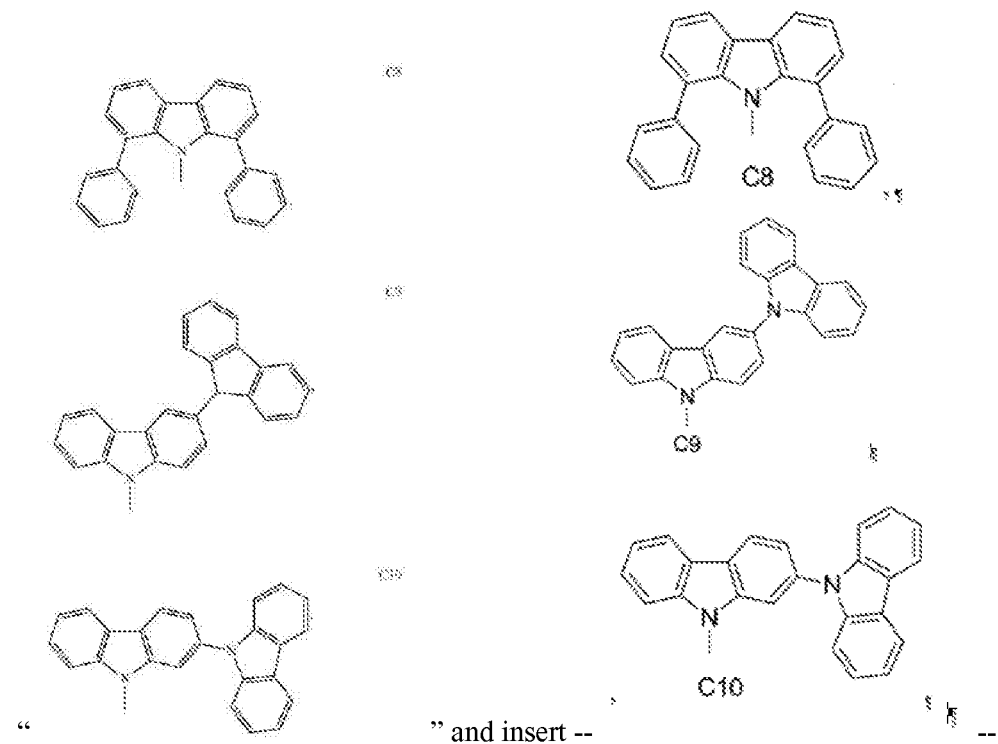

" and insert --

Column 172, Lines 1-35, please delete

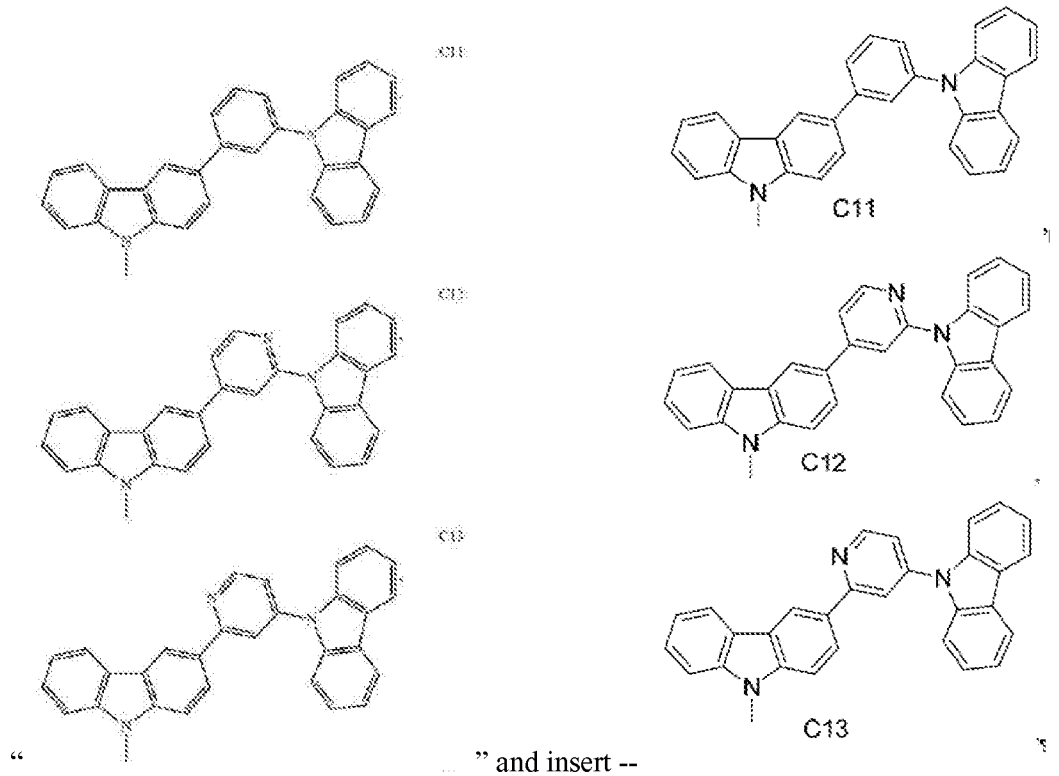

" and insert --  --

Column 172, Lines 36-66, please delete

CERTIFICATE OF CORRECTION (continued)
U.S. Pat. No. 9,502,656 B2

Column 173, Lines 1-30, please delete " 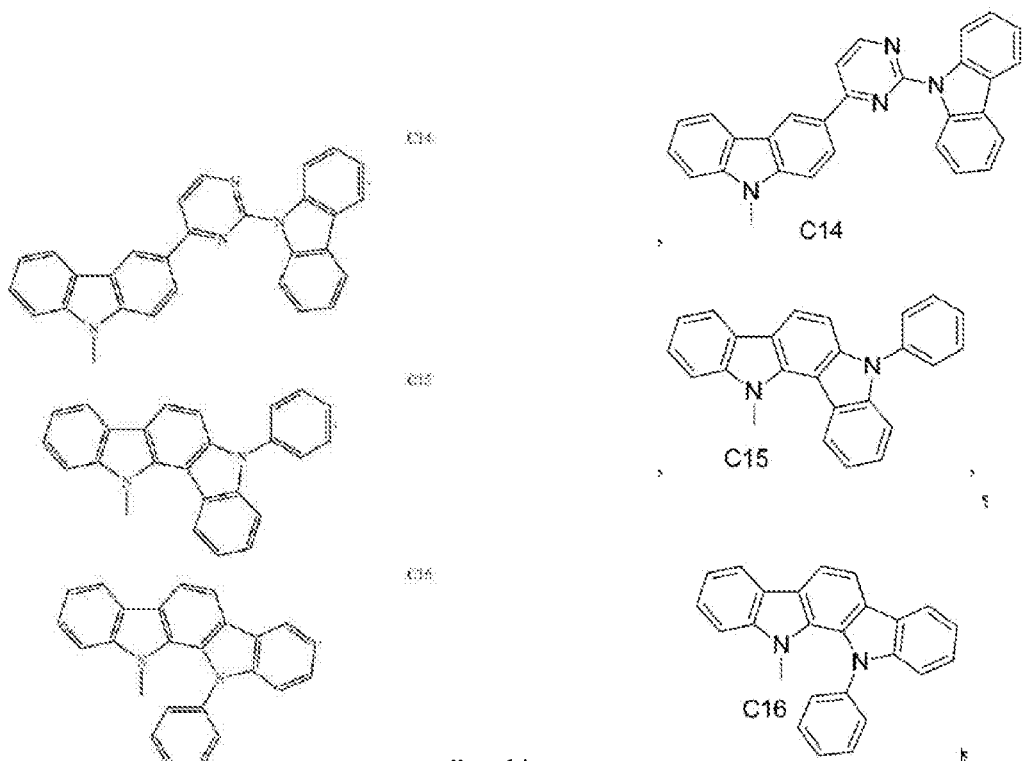 " and insert -- --

Column 173, Lines 31-51, please delete " 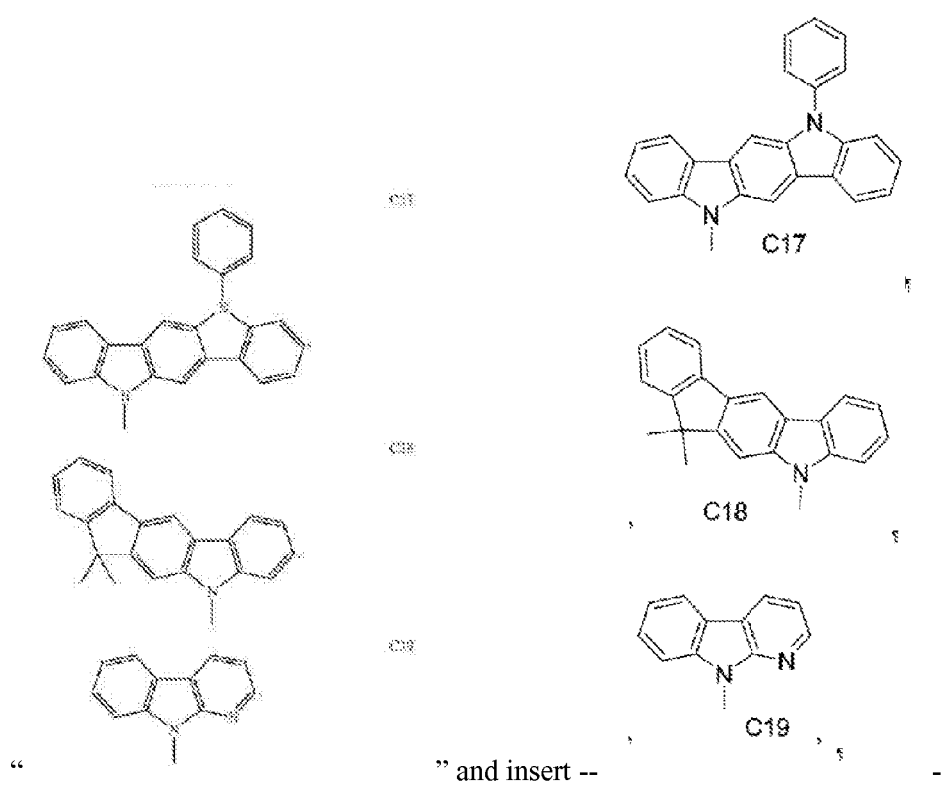 " and insert -- --

CERTIFICATE OF CORRECTION (continued)
U.S. Pat. No. 9,502,656 B2

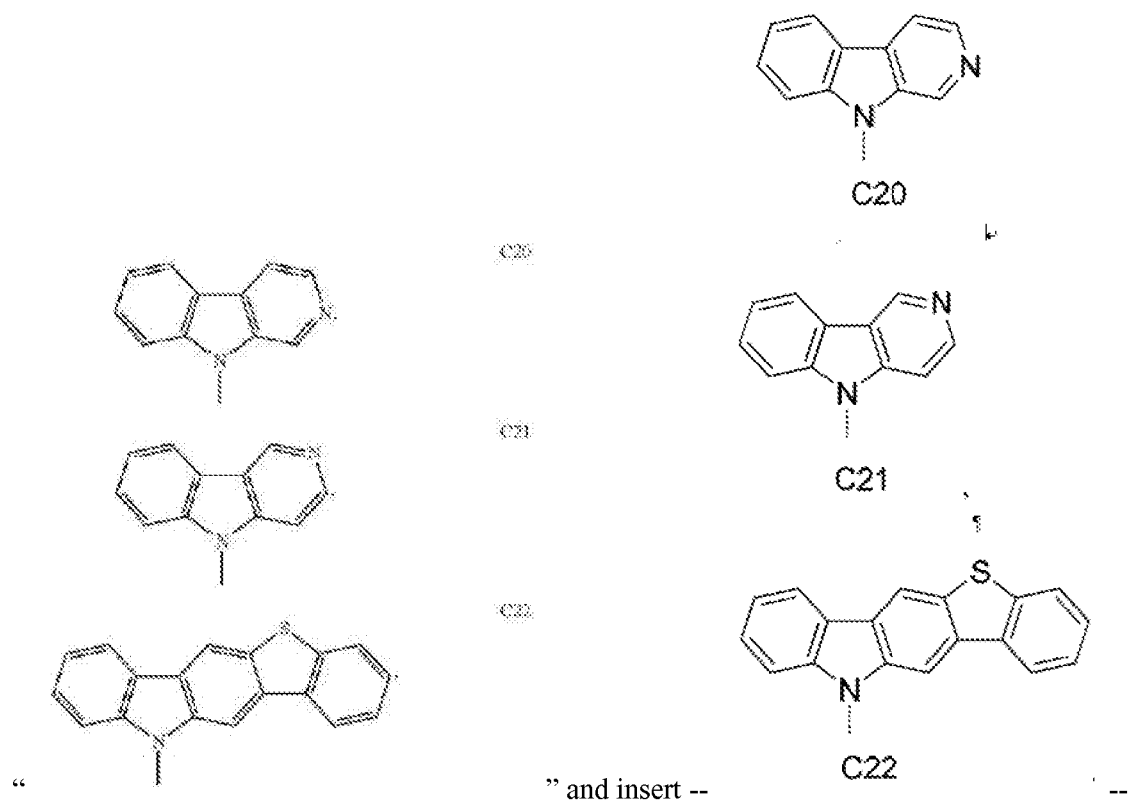

" and insert --                                                                                                     --

Column 173, Lines 52-66, please delete

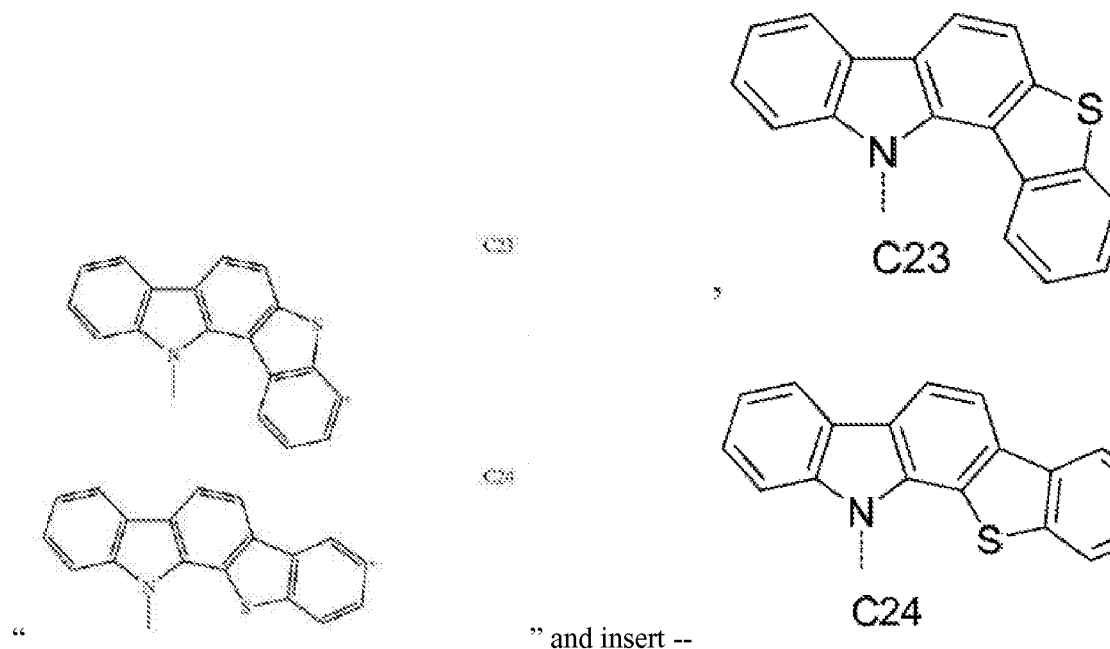

" and insert --                                                                                                     --

Column 174, Lines 1-29, please delete

CERTIFICATE OF CORRECTION (continued)
U.S. Pat. No. 9,502,656 B2

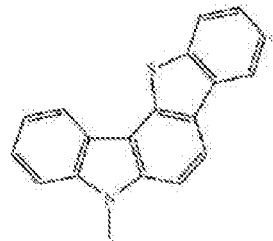 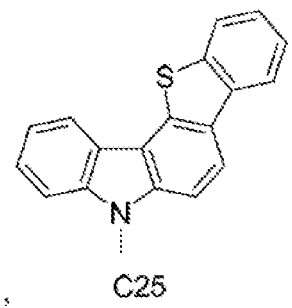

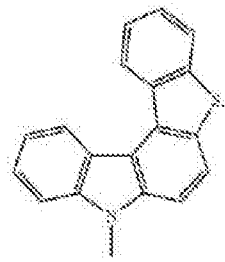 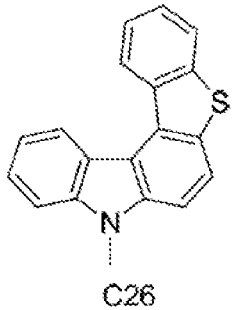

" and insert -- --

Column 188, Lines 15-27, please delete

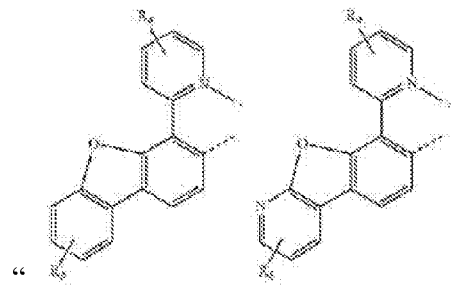 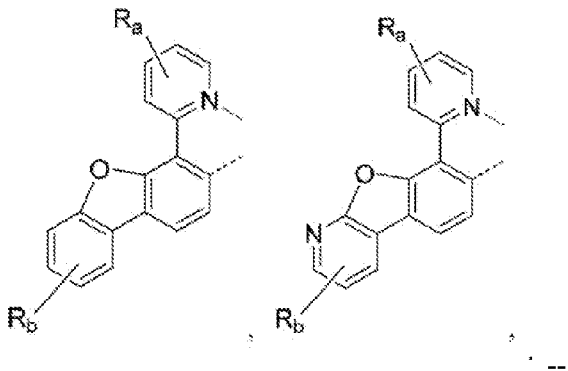

" and insert -- --

Column 188, Lines 28-52, please delete

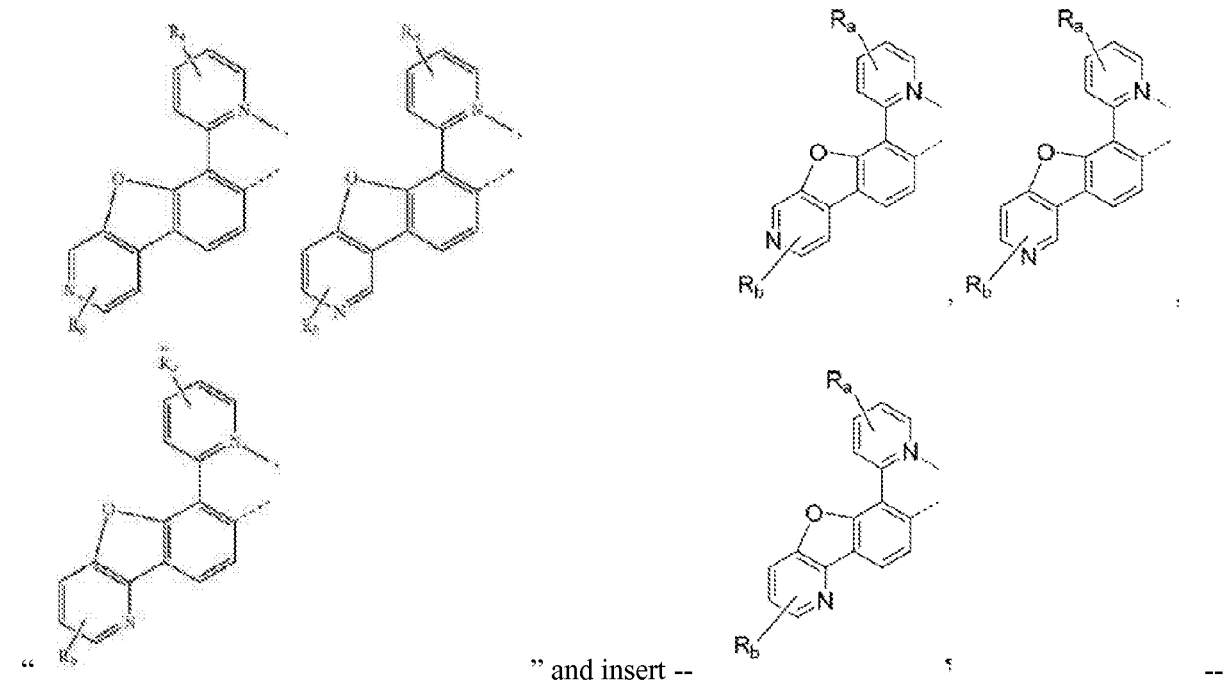
" and insert --                                              --
Column 189, Lines 42-63, please delete
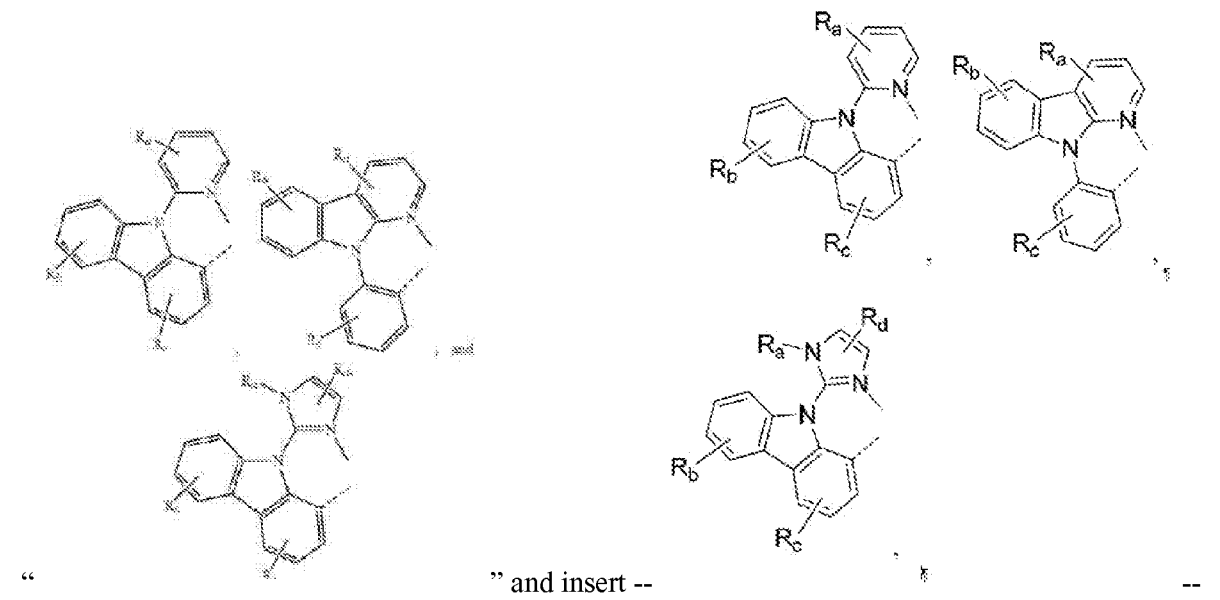
" and insert --                                              --